US008163291B2

(12) United States Patent
Chang et al.

(10) Patent No.: US 8,163,291 B2
(45) Date of Patent: Apr. 24, 2012

(54) METHODS FOR GENERATING STABLY LINKED COMPLEXES COMPOSED OF HOMODIMERS, HOMOTETRAMERS OR DIMERS OF DIMERS AND USES

(75) Inventors: Chien-Hsing Chang, Downingtown, PA (US); David M. Goldenberg, Mendham, NJ (US); William J. McBride, Boonton, NJ (US); Edmund A. Rossi, Woodland Park, NJ (US)

(73) Assignee: IBC Pharmaceuticals, Inc., Morris Plains, NJ (US)

( * ) Notice: Subject to any disclaimer, the term of this patent is extended or adjusted under 35 U.S.C. 154(b) by 156 days.

(21) Appl. No.: 12/468,589

(22) Filed: May 19, 2009

(65) Prior Publication Data

US 2011/0008251 A1    Jan. 13, 2011

Related U.S. Application Data

(62) Division of application No. 11/389,358, filed on Mar. 24, 2006, now Pat. No. 7,550,143.

(60) Provisional application No. 60/668,603, filed on Apr. 6, 2005, provisional application No. 60/728,292, filed on Oct. 19, 2005, provisional application No. 60/751,196, filed on Dec. 16, 2005.

(51) Int. Cl.
*A61K 39/385* (2006.01)
*A61K 39/44* (2006.01)
*A61K 39/00* (2006.01)
*A61K 39/395* (2006.01)

(52) U.S. Cl. ............ 424/193.1; 424/192.1; 424/133.1; 424/134.1; 424/135.1; 424/144.1; 424/178.1; 424/180.1

(58) Field of Classification Search .................. None
See application file for complete search history.

(56) References Cited

U.S. PATENT DOCUMENTS

| | | | |
|---|---|---|---|
| 4,046,722 A | 9/1977 | Rowland | |
| 4,699,784 A | 10/1987 | Shih et al. | |
| 4,868,109 A | 9/1989 | Lansdorp et al. | |
| 5,677,425 A * | 10/1997 | Bodmer et al. | 530/387.1 |
| 5,770,198 A | 6/1998 | Coller et al. | |
| 6,045,793 A * | 4/2000 | Rybak et al. | 424/94.6 |
| 6,261,537 B1 | 7/2001 | Klaveness et al. | |
| 6,306,393 B1 | 10/2001 | Goldenberg | |
| 6,524,854 B1 | 2/2003 | Monia et al. | |
| 6,617,135 B1 | 9/2003 | Gillies et al. | |
| 6,955,717 B2 * | 10/2005 | Johnson et al. | 117/2 |
| 6,991,790 B1 * | 1/2006 | Lam et al. | 424/130.1 |
| 7,060,506 B2 | 6/2006 | Craig | |
| 7,151,164 B2 | 12/2006 | Hansen et al. | |
| 7,282,567 B2 * | 10/2007 | Goldenberg et al. | 530/387.3 |
| 7,521,056 B2 * | 4/2009 | Chang et al. | 424/192.1 |
| 7,527,787 B2 * | 5/2009 | Chang et al. | 424/133.1 |
| 7,534,866 B2 * | 5/2009 | Chang et al. | 530/350 |
| 7,541,440 B2 | 6/2009 | Goldenberg et al. | |
| 7,550,143 B2 * | 6/2009 | Chang et al. | 424/134.1 |
| 7,591,994 B2 * | 9/2009 | Govindan et al. | 424/1.49 |
| 7,858,070 B2 * | 12/2010 | Chang et al. | 424/1.41 |
| 7,871,622 B2 * | 1/2011 | Chang et al. | 424/178.1 |
| 7,901,680 B2 * | 3/2011 | Chang et al. | 424/134.1 |
| 7,906,118 B2 * | 3/2011 | Chang et al. | 424/134.1 |
| 7,906,121 B2 * | 3/2011 | Chang et al. | 424/178.1 |
| 7,981,398 B2 * | 7/2011 | Chang et al. | 424/1.41 |
| 2003/0198956 A1 * | 10/2003 | Makowski et al. | 435/6 |
| 2003/0232420 A1 | 12/2003 | Braun et al. | |
| 2004/0018587 A1 | 1/2004 | Makowski et al. | |
| 2005/0003403 A1 | 1/2005 | Rossi et al. | |
| 2006/0210475 A1 | 9/2006 | Goldenberg et al. | |
| 2007/0264265 A1 | 11/2007 | Goldenberg et al. | |
| 2009/0060862 A1 | 3/2009 | Chang et al. | |
| 2009/0111143 A1 | 4/2009 | Goldenberg et al. | |
| 2009/0191225 A1 * | 7/2009 | Chang et al. | 424/181.1 |
| 2009/0202433 A1 * | 8/2009 | Chang et al. | 424/1.49 |
| 2009/0202487 A1 * | 8/2009 | Chang et al. | 424/85.7 |
| 2009/0269277 A1 * | 10/2009 | Chang et al. | 424/1.49 |
| 2009/0304580 A1 * | 12/2009 | Goldenberg et al. | 424/1.49 |
| 2010/0068137 A1 * | 3/2010 | Chang et al. | 424/1.49 |
| 2010/0261885 A1 * | 10/2010 | Chang et al. | 530/351 |
| 2011/0008251 A1 * | 1/2011 | Chang et al. | 424/1.69 |

(Continued)

FOREIGN PATENT DOCUMENTS

WO        00/68248        11/2000

(Continued)

OTHER PUBLICATIONS

Riemer et al, Mol. Immunol. 42: 1121-1124, 2005.*

(Continued)

*Primary Examiner* — Phuong Huynh
(74) *Attorney, Agent, or Firm* — Richard A. Nakashima

(57) ABSTRACT

The present invention concerns methods and compositions for stably tethered structures of defined compositions, which may have multiple functionalities and/or binding specificities. Particular embodiments concern homodimers comprising monomers that contain a dimerization and docking domain attached to a precursor. The precursors may be virtually any molecule or structure, such as antibodies, antibody fragments, antibody analogs or mimetics, aptamers, binding peptides, fragments of binding proteins, known ligands for proteins or other molecules, enzymes, detectable labels or tags, therapeutic agents, toxins, pharmaceuticals, cytokines, interleukins, interferons, radioisotopes, proteins, peptides, peptide mimetics, polynucleotides, RNAi, oligosaccharides, natural or synthetic polymeric substances, nanoparticles, quantum dots, organic or inorganic compounds, etc. Other embodiments concern tetramers comprising a first and second homodimer, which may be identical or different. The disclosed methods and compositions provide a facile and general way to obtain homodimers, homotetramers and heterotetramers of virtually any functionality and/or binding specificity.

28 Claims, 27 Drawing Sheets

U.S. PATENT DOCUMENTS

| | | | |
|---|---|---|---|
| 2011/0020273 A1* | 1/2011 | Chang et al. | 424/85.2 |
| 2011/0143417 A1* | 6/2011 | Chang et al. | 435/188 |
| 2011/0158905 A1* | 6/2011 | Goldenberg et al. | 424/1.49 |
| 2011/0165072 A1* | 7/2011 | Gold et al. | 424/1.49 |
| 2011/0195020 A1* | 8/2011 | Chang et al. | 424/1.49 |

FOREIGN PATENT DOCUMENTS

| | | |
|---|---|---|
| WO | 2007/075270 | 7/2007 |

OTHER PUBLICATIONS

Tancovski et al, Proceedings of the National Academy of Science USA 88: 8691-8695, 1991.*

Alto et al. "Bioinformatic design of A-kinase anchoring protein-in silico: a potent and selective peptide antagonist of type II protein kinase A anchoring" Proc. Natl. Acad. Sci USA Apr. 15, 2003; 100(8):4445-50.

Banky et al. "Dimerization/Docking Domain of the Type Iα Regulatory Subunit of cAMP-dependent Protein Kinase", J. Biol. Chem. 273:35048-55, 1998.

Carr et al. "Interaction of the Regulatory Subunit (RII) of cAMP-dependent Protein Kinase with RII-anchoring Proteins Occurs through an Amphipathic Helix Binding Motif", J. Biol. Chem. 266:14188-92 (1991).

Chang et al. "The Dock and Lock Method: A Novel Platform Technology for Building Multivalent, Multifunctional Structures of Defined Composition with Retained Bioactivity" Clin. Cancer Res. Sep. 15, 2007;13(18 Suppl), pp. 5586s-5591s.

Colledge et al. "AKAPs: from structure to function", Trends Cell Biol. 6:216-21 (1999).

Corbin et al. "Regulation of Adenosine 3',5'-Monophosphate-dependent Protein Kinase", J. Biol. Chem. 248:1813-21 (1973).

Gillies et al. "High-level expression of chimeric antibodies using adapted cDNA variable region cassettes", J. Immunol. Methods 125 (1989) 191-202.

Gold et al. "A Novel Bispecific, Trivalent Antibody Construct for Targeting Pancreatic Carcinoma", Cancer Res. 68:4819-26, 2008.

Goldenberg et al. "Multifunctional Antibodies by the Dock-and-Lock Method for Improved Cancer Imaging and Therapy by Pretargeting", J. Nucl. Med. 49:158-63, 2008.

Hausken et al. "Mutational Analysis of the A-Kinase Anchoring Protein (AKAP)-binding Site on RII", J. Biol. Chem. 271:29016-22 (1996).

Hodneland et al. "Selective immobilization of proteins to self-assembled monolayers presenting active site-directed capture ligands", Proc. Natl. Acd. Sci. USA 2002; 99:5048-5052.

Lohmann et al. "High-affinity binding of the regulatory subunit (RII) of cAMP-dependent protein kinase to microtubule-associated and other cellular proteins", Proc. Natl. Acad. Sci. USA 81:6723-27 (1984).

Mason, Anthony J. "Functional Analysis of the Cysteine Residues of Activin A", Mol. Endocrinol. 8:325-32, 1994.

Newlon et al. "A Novel Mechanism of PKA Anchoring Revealed by Solution Structures of Anchoring Complexes", EMBO J. 2001; 20:1651-1662.

Newlon et al. "The molecular basis for protein kinase A anchoring revealed by solution NMR", Nature Struct. Biol. 1999; 3:222-227.

Ngo et al. "Computational Complexity, Protein Structure Prediction, and the Levinthal Paradox", The Protein Folding Problem and Tertiary Structure Prediction, Ch. 14, pp. 492-495, (Mertz & Le Grand, Eds.), Birkhauser Boston, 1994.

Oyen et al. "Human testis cDNA for the regulatory subunit RIIα of cAMP-dependent protein kinase encodes an alternate amino-terminal region", FEBS Letters 246:57-64, 1989.

Rose et al. "Structural basis of dimerization, coactivator recognition and MODY3 mutations in HNF-1α", Nature Struct. Biol. 2000; 7:744-748.

Rossi et al. "Novel Designs of Multivalent Anti-CD20 Humanized Antibodies as Improved Lymphoma Therapeutics", Cancer Res. 68:8384-92, 2008.

Rustandi et al. "The Ca2+-Dependent Interaction of S100B(ββ) with a Peptide Derived from p53", Biochemistry 1998; 37: 1951-1960.

Scott et al. "Type II Regulatory Subunit Dimerization Determines the Subcellular Localization of the cAMP-dependent Protein Kinase", J. Biol. Chem. 265:21561-66 (1990).

Sharkey et al. "Improved Therapeutic Results by Pretargeted Radioimmunotherapy of Non-Hodgkin's Lymphoma with a New Recombinant, Trivalent, Anti-CD20, Bispecific Antibody", Cancer Res. 68:5282-90, 2008.

Sharkey et al. "Metastatic Human Colonic Carcinoma: Molecular Imaging with Pretargeted SPECT and PET in a Mouse Model", Radiology 246:497-507, 2008.

Stryer et al. "Levels of Structure in Protein Architecture", Biochemistry, 3rd Ed., pp. 31-33, W.H. Freeman & Co., New York, 1988.

Winkler et al. "Changing the Antigen Binding Specificity by Single Point Mutations of an Anti-p24 (HIV-1) Antibody", J. Immunol. 165:4505-14, 2000.

Wong et al. "AKAP Signalling Complexes: Focal Points in Space and Time", Nat. Rev. Mol. Cell Biol. 12:959-70 (2004).

Zhu et al. "Inhibition of tumor growth and metastasis by targeting tumor-associated angiogenesis with antagonists to the receptors of vascular endothelial growth factor", Invest. New Drugs 17:195-212, 1999.

Santini et al., "Type I Interferon as a Powerful Adjuvant for Monocyte-derived Dendritic Cell Development and Activity in Vivo and in Hu-PBL-SCID Mice" J. Exp. Med. 191(10):1777-1788 (2000).

Scott et al., "Cyclic nucleotide-dependent protein kinases" Pharmacol. Ther. 1991;50(1):123-45.

Seffernick et al., "Melamine Deaminase and Atrazine Chlorohydrolase: 98 Percent Identical but Functionally Different" J. Bacteriol. 183(8):2405-2410 (2001).

Sidky et al., "Inhibition of Angiogenesis by Interferons: Effects on Tumor- and Lymphocyte-induced Vascular Responses" Cancer Res. 47:5155-5161, Oct. 1, 1987.

Stein et al., "Characterization of a New Humanized Anti-CD20 Monoclonal Antibody, IMMU-106, and Its Use in Combination with the Humanized Anti-CD22 Antibody, Epratuzumab, for the Therapy of Non-Hodgkin's Lymphoma" Clin. Cancer Res. vol. 10, 2868-2878, Apr. 15, 2004.

Stein et al., "Characterization of a humanized IgG4 anti-HLA-DR monoclonal antibody that lacks effector cell functions but retains direct antilymphoma activity and increases the potency of rituximab" Blood 2006;108:2736-2744.

Stokka et al., "Characterization of A-kinase-anchoring disruption using a solution-based assay" Biochem. J. (2006) 400, 493-499.

Takaoka et al., "Integration of interferon-α/βsignalling to p53 responses in tumour suppression and antiviral defence" Nature Jul. 31, 2003;424(6948):516-23.

Taylor, S., "cAMP-dependent Protein Kinase" J. Biol. Chem. 1989;264(15):8443-8446.

Walsh et al., "An Adenosine 3', 5'-Monophosphate-dependant Protein Kinase from Rabbit Skeletal Muscle" J. Biol. Chem. 243(13):3763-3774 (1968).

Weck et al., "Comparison of the Antiviral Activities of Various Cloned Human Interferon-α Subtypes in Mammalian Cell Cultures" J. Gen. Virol. (1981), 57, 233-237.

Witkowski et al., "Conversion of a β-Ketoacyl Synthase to a Malonyl Decarboxylase by Replacement of the Active-Site Cysteine with Glutamine" Biochemistry 38(36):11643-50 (1999).

Abbas et al., Cellular and Molecular Immunology, W.B. Saunders Comp. 1991, p. 43.

Backer et al., "Self-Assembled "Dock and Lock" System for Linking Payloads to Targeting Proteins" Bioconjugate Chem., 2006, 17(4):912-919.

Baillie et al., "Compartmentalisation of phospodiesterases and protein kinase A: opposites attract", FEBS Letters 2005; 579:3264-3270.

Basu et al., "Structure-Function Engineering of Interferon-β-1b for Improving Stability, Solubility, Potency, Immunogenicity, and Pharmacokinetic Properties by Site-Selective Mono-PEGylation", Bioconjugate Chem. 2006; 17:618-630.

Belardelli et al., "Interferon-alpha in tumor immunity and immunotherapy" Cytokine Growth Factor Rev. 13(2):119-134 (2002).

Belardelli et al., "International Meeting on Cancer Vaccines: How Can We Enhance Efficacy of Therapeutic Vaccines?" Cancer Res. 64:6827-6830 (2004).

Belardelli et al., "The neglected role of type I interferon in the T-cell response: implications for its clinical use" Immunol. Today 17(8):369-72 (1996).

Biron et al., "Natural killer cells in antiviral defense: function and regulation by innate cytokines" Annu. Rev. Immunol. 17:189-220 (1999).

Brunda et al., "Modulation of Murine Natural Killer Cell Activity in Vitro and in Vivo by Recombinant Human Interferons" Cancer Res. 44:597-601 (1984).

Burns-Hamuro et al., "Distinct interaction modes of an AKAP bound to two regulatory subunit isoforms of protein kinase A revealed by amide hydrogen/deuterium exchange" Protein Science (2005), 14:2982-2992.

Carr et al., "Identification of Sperm-specific Proteins That Interact with A-kinase Anchoring Proteins in a Manner Similar to the Type II Regulatory Subunit of PKA" J. Biol. Chem. 276(20):17332-17338 (2001).

Carrero et al., "Lymphocytes are detrimental during the early innate immune response against Listeria monocytogenes" J. Exp. Med. 203(4):933-940 (2006).

Chmura et al., "Antibodies with infinite affinity" Proc. Natl. Acad. Sci. USA 98(15):8480-8484 (2001).

Dhalluin et al., "Structural and Biophysical Characterization of the 40 kDa PEG-Interferon-α2a and Its Individual Positional Isomers" Bioconjugate Chem. 2005;16:504-517.

Dodart et al., "Immunotherapy for Alzheimer's Disease: will vaccination work?" Trends Mol. Med. 9(3):85-87 (2003).

Doherty et al., "Site-Specific PEGylation of Engineered Cysteine Analogues of Recombinant Human Granulocyte-Macrophage Colony-Stimulating Factor", Bioconjugate Chem. 2005;16:1291-1298.

Ferrantini et al., "IFN-α1 Gene Expression into a Metastatic Murine Adenocarcinoma (TS/A) Results in CD8+ T Cell-Mediated Tumor Rejection and Development of Antitumor Immunity" J. Immunol. 153:4604-15 (1994).

Ferrantini et al., "Interferon-α and cancer: Mechanisms of action and new perspectives of clinical use" Biochimie 89: 884-893 (2007).

Glennie et al., "Mechanisms of killing by anti-CD20 monoclonal antibodies" Mol. Immunol. 44:3823-3837 (2007).

Gold et al., "Molecular Basis of AKAP Specificity for PKA Regulatory Subunits" Mol. Cell Nov. 3, 2006;24(3):383-95.

Goldenberg et al., "Properties and structure-function relationships of veltuzumab (hA20), a humanized anti-CD20 monoclonal antibody" Blood 113:1062-70 (2009).

Goodson et al., "Site-Directed PEGylation of Recombinant Interleukin-2 at its Glycosylation Site", Nat. Biotechnology Apr. 1990;8(4):343-6.

Grace et al., "Site of Pegylation and Polyethylene Glycol Molecule Size Attenuate Interferon-α Antiviral and Antiproliferative Activities through the JAK/STAT Signaling Pathway" J. Biol. Chem. 2005;280(8):6327-6336.

Grimley et al., "Prolonged STAT1 Activation Related to the Growth Arrest of Malignant Lymphoma Cells by Interferon-α" Blood 91(8):3017-27 (1998).

Gutterman et al., "Leukocyte Interferon-Induced Tumor Regression in Human Metastatic Breast Cancer, Multiple Myeloma, and Malignant Lymphoma" Ann. Intern. Med. 93(3):399-406 (1980).

Gutterman et al., "Cytokine therapeutics: Lessons from interferon α" Proc. Natl. Acad. Sci. USA 91:1198-205 (1994).

Harris et al., "Effect of pegylation on pharmaceuticals" Nat. Rev. Drug. Discov. 2:214-221 (2003).

Huang et al., "Targeting IFN-α to B Cell Lymphoma by a Tumor-Specific Antibody Elicits Potent Antitumor Activities" J. Immunol. 179:6881-88 (2007).

Hundsrucker et al., "High-affinity AKAP7δ-protein kinase A interaction yields novel protein kinase A-anchoring disruptor peptides" Biochem. J. (2006) 396, 297-306.

Kimby et al., "Long-term molecular remissions in patients with indolent lymphoma treated with rituximab as a single agent or in combination with interferon alpha-2a: A randomized phase II study from the Nordic Lymphoma Group" Leuk. Lymphoma 49(1):102-112 (2008).

Kinderman et al., "A Dynamic Mechanism for AKAP Binding to RII Isoforms of cAMP-Dependent Protein Kinase" Mol. Cell 24(3):397-408 (2006).

Kinstler et al., "Characterization and Stability of N-terminally PEGylated rhG-CSF" Pharm. Res. 1996;13 (7):996-1002.

Kramer et al., "Cell and virus sensitivity studies with recombinant human alpha interferons" J. Interferon. Res. 3 (4):425-35 (1983).

Le Bon et al., "Type I Interferons Potently Enhance Humoral Immunity and Can Promote Isotype Switching by Stimulating Dendritic Cells In Vivo" Immunity 14:461-470 (2001).

Lee et al., "Solid-Phase PEGylation of Recombinant Interferon α-2a for Site-Specific Modification: Process Performance, Characterization, and in Vitro Bioactivity" Bioconjugate Chem. 2007; 18:1728-34.

Luft et al., "Type I IFNs Enhance the Terminal Differentiation of Dendritic Cells" J. Immunol. 161:1947-1953 (1998).

Matarrese et al., "Type I Interferon Gene Transfer Sensitizes Melanoma Cells to Apoptosis via a Target Activity on Mitochondrial Function" Am. J. Pathol. 2002, 160(4):1507-1520.

Mecchia et al., "Type I consensus interferon (CIFN) gene transfer into human melanoma cells up-regulates p53 and enhances cisplatin-induced apoptosis: implications for new therapeutic strategies with IFN-alpha" Gene Ther. (2000) 7, 167-179.

Osborn et al., "Pharmacokinetic and Pharmacodynamic Studies of a Human Serum Albumin-Interferon-α Fusion Protein in Cynomolgus Monkeys" J. Pharmacol. Exp. Ther. 303(2):540-548 (2002).

Ozzello et al., "Conjugation of interferon alpha to a humanized monoclonal antibody (HuBrE-3vI) enhances the selective localization and antitumor effects of interferon in breast cancer xenografts" Breast Cancer Res. Treat. 48: 135-147 (1998).

Paquette et al., "Interferon-α and granulocyte-macrophage colony-stimulating factor differentiate peripheral blood monocytes into potent antigen-presenting cells" J. Leukoc. Biol. 64:358-367; 1998.

Pelham et al., "Interferon-α conjugation to human osteogenic sarcoma monoclonal antibody 791T/36" Cancer Immunol. Immuother 1983;15(3):210-216.

Pepinsky et al., "Improved Pharmacokinetic Properties of a Polyethylene Glycol-Modified Form of Interferon-β-1a with Preserved in Vitro Bioactivity" Pharmacol. Exp. Ther. 2001; 297(3):1059-1066.

Pilling et al., "Interferon-β mediates stromal cell rescue of T cells from apoptosis" Eur. J. Immunol. 29:1041-1050 (1999).

Rabjohn et al., "Molecular Cloning and Epitope Analysis of the Peanut Allergen Ara h 3" J. Clinical Investigation 103 (4):535-542 (1999).

Raefsky et al., "Studies of Interferon as a regulator of hematopoietic cells proliferation" J. Immunol. 135 (4):2507-2512 (1985).

Rosendahl et al., "A Long-Acting, Highly Potent Interferon α-2 Conjugate Created Using Site-Specific PEGylation" Bioconjugate Chem. 2005;16:200-207.

Rossi et al., "Stably tethered multifunctional structures of defined composition made by the dock and lock method for use in cancer targeting" Proc. Natl. Acad. Sci. Epub Apr. 24, 2006, vol. 103, No. 18, pp. 6841-6846.

Sabaawy et al., "Enhancement of 5-fluorouracil cytotoxicity on human colon cancer cells by retrovirus-mediated interferon-α gene transfer" Int. J. Oncol. Jun. 1999; 14(6):1143-51.

Salles et al., "Rituximab combined with chemotherapy and interferon in follicular lymphoma patients: results of the GELA-GOELAMS FL2000 study" Blood 2008; 112:4824-4831.

* cited by examiner

Figure 1 a) DDD1:

*NH2-*SHIQIPPGLTELLQGYTVEVLRQQPPDLVEFAVEYFTRLR EARA*-COOH* (SEQ ID NO:1)

b) DDD2:

*NH2-*CGHIQIPPGLTELLQGYTVEVLRQQPPDLVEFAVEYFTRL REARA*-COOH* (SEQ ID NO:2)

Figure 5

AD1-C:
*NH2*-KQIEYLAKQIVDNAIQQAKGC-*COOH* (SEQ ID NO:3)

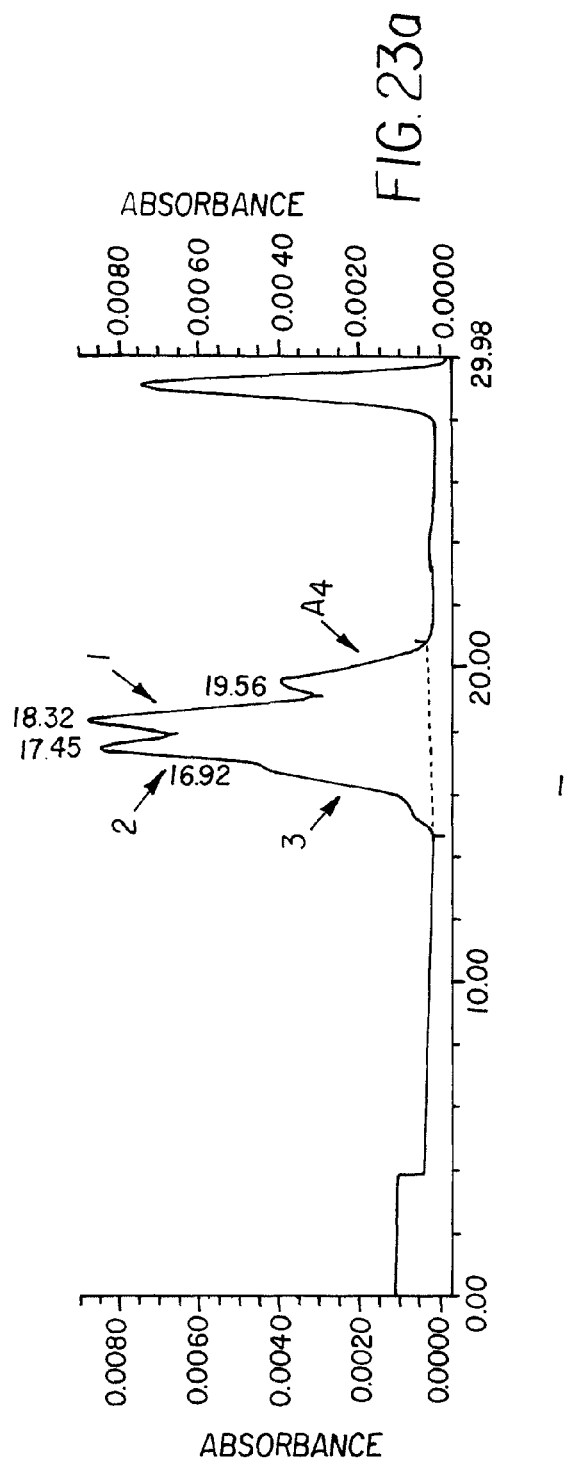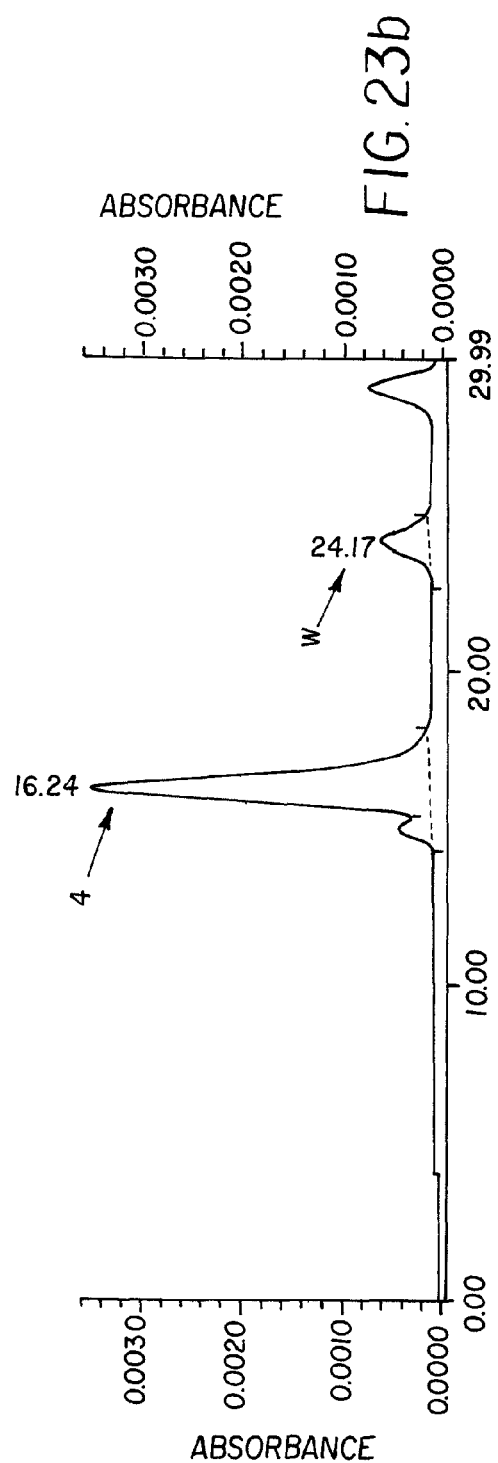

SEQUENCE LISTING

<160> NUMBER OF SEQ ID NOS: 18

<210> SEQ ID NO 1
<211> LENGTH: 44
<212> TYPE: PRT
<213> ORGANISM: Artificial
<220> FEATURE:
<223> OTHER INFORMATION: peptide, synthetic

<400> SEQUENCE: 1

Ser His Ile Gln Ile Pro Pro Gly Leu Thr Glu Leu Leu Gln Gly Tyr
 1               5                  10                  15

Thr Val Glu Val Leu Arg Gln Gln Pro Pro Asp Leu Val Glu Phe Ala
                20                  25                  30

Val Glu Tyr Phe Thr Arg Leu Arg Glu Ala Arg Ala
            35                  40

<210> SEQ ID NO 2
<211> LENGTH: 45
<212> TYPE: PRT
<213> ORGANISM: Artificial
<220> FEATURE:
<223> OTHER INFORMATION: peptide, synthetic

<400> SEQUENCE: 2

Cys Gly His Ile Gln Ile Pro Pro Gly Leu Thr Glu Leu Leu Gln Gly
 1               5                  10                  15

Tyr Thr Val Glu Val Leu Arg Gln Gln Pro Pro Asp Leu Val Glu Phe
                20                  25                  30

Ala Val Glu Tyr Phe Thr Arg Leu Arg Glu Ala Arg Ala
            35                  40                  45

<210> SEQ ID NO 3
<211> LENGTH: 21
<212> TYPE: PRT
<213> ORGANISM: Artificial
<220> FEATURE:
<223> OTHER INFORMATION: peptide, synthetic

<400> SEQUENCE: 3

Lys Gln Ile Glu Tyr Leu Ala Lys Gln Ile Val Asp Asn Ala Ile Gln
 1               5                  10                  15

Gln Ala Lys Gly Cys
            20

<210> SEQ ID NO 4
<211> LENGTH: 20
<212> TYPE: DNA
<213> ORGANISM: Artificial
<220> FEATURE:
<223> OTHER INFORMATION: oligonucleotide, synthetic

<400> SEQUENCE: 4
gaacctcgcg gacagttaag                                            20

<210> SEQ ID NO 5
<211> LENGTH: 53
<212> TYPE: DNA
<213> ORGANISM: Artificial
<220> FEATURE:
<223> OTHER INFORMATION: oligonucleotide, synthetic

<400> SEQUENCE: 5

```
ggatcctccg ccgccgcagc tcttaggttt cttgtccacc ttggtgttgc tgg      53
```

<210> SEQ ID NO 6
<211> LENGTH: 55
<212> TYPE: PRT
<213> ORGANISM: Artificial
<220> FEATURE:
<223> OTHER INFORMATION: peptide, synthetic

<400> SEQUENCE: 6

```
Gly Ser Gly Gly Gly Ser Gly Gly Gly Ser His Ile Gln Ile
1               5                   10                  15
Pro Pro Gly Leu Thr Glu Leu Leu Gln Gly Tyr Thr Val Glu Val Leu
            20                  25                  30
Arg Gln Gln Pro Pro Asp Leu Val Glu Phe Ala Val Glu Tyr Phe Thr
        35                  40                  45
Arg Leu Arg Glu Ala Arg Ala
    50                  55
```

<210> SEQ ID NO 7
<211> LENGTH: 92
<212> TYPE: DNA
<213> ORGANISM: Artificial
<220> FEATURE:
<223> OTHER INFORMATION: oligonucleotide, synthetic

<400> SEQUENCE: 7

```
gtggcgggtc tggcggaggt ggcagccaca tccagatccc gccggggctc acggagctgc      60
tgcagggcta cacggtggag gtgctgcgac ag                                    92
```

<210> SEQ ID NO 8
<211> LENGTH: 92
<212> TYPE: DNA
<213> ORGANISM: Artificial
<220> FEATURE:
<223> OTHER INFORMATION: oligonucleotide, synthetic

<400> SEQUENCE: 8

```
gcgcgagctt ctctcaggcg ggtgaagtac tccactgcga attcgacgag gtcaggcggc      60
tgctgtcgca gcacctccac cgtgtagccc tg                                    92
```

<210> SEQ ID NO 9
<211> LENGTH: 30
<212> TYPE: DNA
<213> ORGANISM: Artificial
<220> FEATURE:
<223> OTHER INFORMATION: oligonucleotide, synthetic

<400> SEQUENCE: 9

```
ggatccggag gtggcgggtc tggcggaggt                                       30
```

<210> SEQ ID NO 10
<211> LENGTH: 30
<212> TYPE: DNA
<213> ORGANISM: Artificial
<220> FEATURE:
<223> OTHER INFORMATION: oligonucleotide, synthetic

<400> SEQUENCE: 10

```
cggccgtcaa gcgcgagctt ctctcaggcg                                       30
```

<210> SEQ ID NO 11
<211> LENGTH: 28
<212> TYPE: DNA

-continued

<213> ORGANISM: Artificial
<220> FEATURE:
<223> OTHER INFORMATION: oligonucleotide, synthetic

<400> SEQUENCE: 11
ccatgggcag ccacatccag atcccgcc                                                28

<210> SEQ ID NO 12
<211> LENGTH: 55
<212> TYPE: DNA
<213> ORGANISM: Artificial
<220> FEATURE:
<223> OTHER INFORMATION: oligonucleotide, synthetic

<400> SEQUENCE: 12
ggatccgcca cctccagatc ctccgccgcc agcgcgagct tctctcaggc gggtg            55

<210> SEQ ID NO 13
<211> LENGTH: 55
<212> TYPE: DNA
<213> ORGANISM: Artificial
<220> FEATURE:
<223> OTHER INFORMATION: oligonucleotide, synthetic

<400> SEQUENCE: 13
ggatccgcca cctccagatc ctccgccgcc agcgcgagct tctctcaggc gggtg            55

<210> SEQ ID NO 14
<211> LENGTH: 30
<212> TYPE: DNA
<213> ORGANISM: Artificial
<220> FEATURE:
<223> OTHER INFORMATION: oligonucleotide, synthetic

<400> SEQUENCE: 14
cggccgtcag cagctcttag gtttcttgtc                                              30

<210> SEQ ID NO 15
<211> LENGTH: 48
<212> TYPE: DNA
<213> ORGANISM: Artificial
<220> FEATURE:
<223> OTHER INFORMATION: oligonucleotide, synthetic

<400> SEQUENCE: 15
catgtgcggc cacatccaga tcccgccggg gctcacggag ctgctgca                       48

<210> SEQ ID NO 16
<211> LENGTH: 40
<212> TYPE: DNA
<213> ORGANISM: Artificial
<220> FEATURE:
<223> OTHER INFORMATION: oligonucleotide, synthetic

<400> SEQUENCE: 16
gcagctccgt gagccccggc gggatctgga tgtggccgca                                   40

<210> SEQ ID NO 17
<211> LENGTH: 73
<212> TYPE: DNA
<213> ORGANISM: Artificial
<220> FEATURE:
<223> OTHER INFORMATION: oligonucleotide, synthetic

<400> SEQUENCE: 17
gatccggagg tggcgggtct ggcggaggtt gcggccacat ccagatcccg ccggggctca          60

```
                                         -continued cggagctgct gca                                                          73

<210> SEQ ID NO 18
<211> LENGTH: 65
<212> TYPE: DNA
<213> ORGANISM: Artificial
<220> FEATURE:
<223> OTHER INFORMATION: oligonucleotide, synthetic

<400> SEQUENCE: 18
gcagctccgt gagcccggc gggatctgga tgtggccgca acctccgcca gacccgccac        60
ctccg                                                                   65
```

METHODS FOR GENERATING STABLY LINKED COMPLEXES COMPOSED OF HOMODIMERS, HOMOTETRAMERS OR DIMERS OF DIMERS AND USES

RELATED APPLICATIONS

This application is a divisional of U.S. patent application Ser. No. 11/389,358, filed Mar. 24, 2006, which claimed the benefit under 35 U.S.C. §119(e) of provisional U.S. patent application Ser. No. 60/668,603, filed Apr. 6, 2005; 60/728,292, filed Oct. 20, 2005; 60/751,196, filed Dec. 16, 2005; and 60/782,332, filed Mar. 14, 2006. The text of each of the priority applications is incorporated herein by reference in its entirety.

BACKGROUND OF THE INVENTION

Man-made agents that incorporate multiple copies of both targeting and effector moieties are highly desirable, as they should provide more avid binding and confer enhanced potency. Although recombinant technologies are commonly applied for making fusion proteins with both targeting and effector domains, multimeric structures that comprise the same or different monomeric components to acquire multivalency or multifunctionality may be obtained only with judicious applications of conjugation chemistries.

For agents generated by recombinant engineering, problems may include high manufacturing cost, low expression yields, instability in serum, instability in solution resulting in formation of aggregates or dissociated subunits, undefined batch composition due to the presence of multiple product forms, contaminating side-products, reduced functional activities or binding affinity/avidity attributed to steric factors or altered conformations, etc. For agents generated by various methods of chemical cross-linking, high manufacturing cost and heterogeneity of the purified product are two major limitations.

Thus, there remains a need in the art for a method of making multivalent structures of multiple specificities or functionalities in general, which are of defined composition, homogeneous purity, and unaltered affinity, and can be produced in high yields without the requirement of extensive purification steps. Furthermore, such structures must also be sufficiently stable in serum to allow in vivo applications. A need exists for stable, multivalent structures of multiple specificities or functionalities that are easy to construct and/or obtain in relatively purified form.

SUMMARY OF THE INVENTION

The present invention discloses a platform technology for generating stably tethered structures that may have multiple functions or binding specificities or both, and are suitable for in vitro as well as in vivo applications. In one embodiment, the stably tethered structures are produced as a homodimer of any organic substance, which can be proteins or non-proteins. The homodimer, referred to as $a_2$ hereafter, is composed of two identical subunits linked to each other via a distinct peptide sequence, termed the dimerization and docking domain (DDD), which is contained in each subunit. The subunit is constructed by linking a DDD sequence to a precursor of interest by recombinant engineering or chemical conjugation via a spacer group, resulting in a structure that is capable of self-association to form a dimer. Representative $a_2$ constructs made with the DDD sequence referred to as DDD1 (FIG. 1a, SEQ ID NO:1) are described in Examples 2 and 3.

In another embodiment, the stably tethered structures are produced predominantly as a homotetramer of any organic substance, which can be proteins or non-proteins. The homotetramer, referred to as $a_4$ hereafter, is composed of two identical $a_2$ constructs made with the DDD sequence referred to as DDD2 (FIG. 1b, SEQ ID NO:2), which is contained in each of the four subunits. Five such $a_4$ constructs are described in Examples 4 and 5.

In yet another embodiment, the stably tethered structures are produced as a hybrid tetramer from any two distinct $a_4$ constructs. The hybrid tetramer, referred to as $a_2a'_2$ hereafter, is composed of two different $a_2$ constructs derived from respective $a_4$ constructs. Three such $a_2a'_2$ constructs are described in Example 6. In other embodiments, fusion proteins that are single-chain polypeptides comprising multiple domains, such as avimers (Silverman et al., Nat. Biotechnol. (2005), 23: 1556-1561) for example, may serve as precursors of interest to increase the valency, functionality, and specificity of the resulting $a_2$, $a_4$ and $a_2a'_2$ constructs, which may be further conjugated with effectors and carriers to acquire additional functions enabled by such modifications.

Numerous $a_2$, $a_4$ and $a_2a'_2$ constructs can be designed and produced with the disclosed methods and compositions. For example, at least 7 types of protein- or peptide-based constructs as listed below are envisioned:

Type 1: A bivalent $a_2$ construct composed of two Fab or scFv fragments derived from the same mAb. See Table 1 for selected examples.

Type 2: A bivalent $a_2$ construct composed of two identical non-immunoglobulin proteins. See Table 2 for selected examples.

Type 3: A tetravalent $a_4$ construct composed of four Fab or scFv fragments derived from the same mAb. See Table 3 for selected examples.

Type 4: A tetravalent $a_4$ constructs composed of four identical non-immunoglobulin proteins. See Table 4 for selected examples.

Type 5: A bispecific tetravalent $a_2a'_2$ construct composed of two Fab or scFv fragments derived from the same mAb and two Fab or scFv fragment derived from a different mAb. See Table 5 for selected examples.

Type 6: A multifunctional $a_2a'_2$ constructs composed of two Fab or scFv fragments derived from the same mAb and two identical non-immunoglobulin proteins. See Table 6 for selected examples.

Type 7: A multifunctional $a_2a'_2$ constructs composed of two pairs of different non-immunoglobulin proteins. See Table 7 for selected examples.

In general, the products in the type 1 category are useful in various applications where a bivalent binding protein composed of two stably tethered Fab (or scFv) fragments derived from the same monoclonal antibody is more desirable than the corresponding bivalent F(ab')$_2$, which is known to dissociate into monovalent Fab' in vivo. For example, the efficacy of an $a_2$ product composed of two stably tethered Fab fragments of 7E3 should be improved over that of ReoPro™ (Centocor, Inc.), which uses the Fab fragment of 7E3 to prevent platelet aggregation.

In general, the products in the type 2 category are useful in various applications where a bivalent agent may be more desirable than a monovalent agent either for improved efficacy or pharmacokinetics or both. For example, an $a_2$ product composed of two copies of erythropoietin may be preferred to Epogen® (Amgen), which contains only one erythropoietin. Another example is an $a_2$ product composed of two copies of Aβ12-28P fused to the CH2 and CH3 domains of human IgG1. Aβ12-28P is the peptide containing the N-terminal 12 to 28 residues of β-amyloid (Aβ) with valine at position 18 replaced by proline. Aβ12-28P is non-fibrillogenic and non-toxic and can block the binding of apolipoprotein E (apoE) to Aβ with reduction of Aβ plaques in a transgenic mouse model (Sadowski et al., Am J Pathol. (2004), 165: 937-948). The fusion of CH2 and CH3 to Aβ12-28P would serve two purposes: (1) to facilitate the resulting complex to cross the blood brain barrier through the FcRn; (2) for effective reduction of Aβ plaque by microglia cells following binding of Aβ to the anti-Aβ arms and binding of the CH2-CH3 domain to the Fc receptors on microglia (Hartman et al., J. Neurosci. (2005), 25: 6213-6220).

In general, the products in the type 3 category are useful in various applications where a tetravalent binding protein composed of four stably tethered Fab (or scFv) fragments derived from the same monoclonal antibody is more desirable than a trivalent, bivalent or monovalent binding protein based on the same monoclonal antibody. For example, the efficacy of an $a_4$ product composed of four stably tethered Fab fragments of an anti-TNF-α antibody such as adalimumab may be more efficacious in treating arthritis than HUMIRA™ (Abbott Laboratories).

In general, the products in the type 4 category are useful in various applications where a tetravalent agent may be more desirable than a trivalent, bivalent or monovalent agent due to the enhanced avidity of binding to the target. For example, an $a_4$ product composed of four copies of factor IX may be preferred as a therapeutic agent for treating hemophilia to Benefix™ (Wyeth), which contains only one factor IX.

In general, the products in the type 5 category are useful in various applications where a bispecific tetravalent binding protein composed of two different $a_2$ subunits is desired. For example, an $a_2a'_2$ product composed of two Fab fragments of trastuzumab and two Fab fragments of pertuzumab may be more efficacious than either Herceptin® (Genentech) or Omnitarg™ (Genentech) for treating cancers that overexpress the HER2 receptor.

In general, the products in the type 6 category are useful in various applications where target-specific delivery or binding of a non-immunoglobulin protein is desired. For example, an $a_2a'_2$ product composed of two Fab fragments of an internalizing antibody against a tumor associated antigen (such as CD74) and two copies of a toxin (such as deglycosylated ricin A chain or ranpirnase) would be valuable for selective delivery of the toxin to destroy the target tumor cell. Another example is an $a_2a'_2$ product composed of two Fab fragments of an antibody against Aβ and two copies of transferin (Tf), which is expected to cross the blood brain barrier and neutralize Aβ for effective therapy of Alzheimer's disease.

In general, the products in the type 7 category are useful in various applications where the combination of two different non-immunoglobulin proteins are more desirable than each respective non-immunoglobulin protein alone. For example, an $a_2a'_2$ product composed of two copies of a soluble component of the receptor for IL-4R (sIL-4R) and two copies of a soluble component of the receptor for IL-13 (sIL-13R) would be a potential therapeutic agent for treating asthma or allergy. Another example is an $a_2a'_2$ product composed of two copies of Aβ12-28P and two copies of Tf. The addition of Tf to Aβ12-28P is expected to enable the resulting complex to cross the blood brain barrier for effective treatment of Alzheimer's disease.

The stably tethered structures of the present invention, including their conjugates, are suitable for use in a wide variety of therapeutic and diagnostic applications. For example, the $a_2$, $a_4$, or $a_2a'_2$ constructs based on the antibody binding domains can be used for therapy where such a construct is not conjugated to an additional functional agent, in the same manner as therapy using a naked antibody. Alternatively, these stably tethered structures can be derivatized with one or more functional agents to enable diagnostic or therapeutic applications. The additional agent may be covalently linked to the stably tethered structures using conventional conjugation chemistries.

Methods of use of stably tethered structures may include detection, diagnosis and/or treatment of a disease or other medical condition. Such conditions may include, but are not limited to, cancer, hyperplasia, diabetic retinopathy, macular degeneration, inflammatory bowel disease, Crohn's disease, ulcerative colitis, rheumatoid arthritis, sarcoidosis, asthma, edema, pulmonary hypertension, psoriasis, corneal graft rejection, neovascular glaucoma, Osler-Webber Syndrome, myocardial angiogenesis, plaque neovascularization, restenosis, neointima formation after vascular trauma, telangiectasia, hemophiliac joints, angiofibroma, fibrosis associated with chronic inflammation, lung fibrosis, deep venous thrombosis or wound granulation.

In particular embodiments, the disclosed methods and compositions may be of use to treat autoimmune disease, such as acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, juvenile diabetes mellitus, Henoch-Schonlein purpura, post-streptococcalnephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitisubiterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis or fibrosing alveolitis.

In certain embodiments, the stably tethered structures may be of use for therapeutic treatment of cancer. It is anticipated that any type of tumor and any type of tumor antigen may be targeted. Exemplary types of tumors that may be targeted include acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal, gastric, head and neck cancer, Hodgkin's lymphoma, lung cancer, medullary thyroid cancer, non-Hodgkin's lymphoma, multiple myeloma, renal cancer, ovarian cancer, pancreatic cancer, glioma, melanoma, liver cancer, prostate cancer, and urinary bladder cancer.

Tumor-associated antigens that may be targeted include, but are not limited to, carbonic anhydrase IX, A3, antigen specific for A33 antibody, BrE3-antigen, CD1, CD1a, CD3, CD5, CD15, CD16, CD19, CD20, CD21, CD22, CD23, CD25, CD30, CD45, CD74, CD79a, CD80, HLA-DR, NCA 95, NCA90, HCG and its subunits, CEA (CEACAM-5), CEACAM-6, CSAp, EGFR, EGP-1, EGP-2, Ep-CAM, Ba 733, HER2/neu, hypoxia inducible factor (HIF), KC4-antigen, KS-1-antigen, KS1-4, Le-Y, macrophage inhibition factor (MIF), MAGE, MUC1, MUC2, MUC3, MUC4, PAM-4-antigen, PSA, PSMA, RS5, S100, TAG-72, p53, tenascin, IL-6, IL-8, insulin growth factor-1 (IGF-1), Tn antigen, Thomson-Friedenreich antigens, tumor necrosis antigens, VEGF, placenta growth factor (P1GF), 17-1A-antigen, an angiogenesis marker (e.g., ED-B fibronectin), an oncogene marker, an oncogene product, and other tumor-associated antigens. Recent reports on tumor associated antigens include Mizukami et al., (2005, *Nature Med.* 11:992-97); Hatfield et al., (2005, *Curr. Cancer Drug Targets* 5:229-48); Vallbohmer et al. (2005, *J. Clin. Oncol.* 23:3536-44); and Ren et al. (2005, *Ann. Surg.* 242:55-63), each incorporated herein by reference.

In other embodiments, the stably tethered structures may be of use to treat infection with pathogenic organisms, such as bacteria, viruses or fungi. Exemplary fungi that may be treated include *Microsporum, Trichophyton, Epidermophyton, Sporothrix schenckii, Cryptococcus neoformans, Coccidioides immitis, Histoplasma capsulatum, Blastomyces dermatitidis* or *Candida albican*. Exemplary viruses include human immunodeficiency virus (HIV), herpes virus, cytomegalovirus, rabies virus, influenza virus, human papilloma virus, hepatitis B virus, hepatitis C virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus or blue tongue virus. Exemplary bacteria include *Bacillus anthraces, Streptococcus agalactiae, Legionella pneumophilia, Streptococcus pyogenes, Escherichia coli, Neisseria gonorrhoeae, Neisseria meningitidis, Pneumococcus* spp., *Hemophilis influenzae* B, *Treponema pallidum*, Lyme disease spirochetes, *Pseudomonas aeruginosa, Mycobacterium leprae, Brucella abortus, Mycobacterium tuberculosis* or a *Mycoplasma*.

Although not limiting, in various embodiments, the precursors incorporated into the monomers, dimers and/or tetramers may comprise one or more proteins, such as a bacterial toxin, a plant toxin, ricin, abrin, a ribonuclease (RNase), DNase I, Staphylococcal enterotoxin-A, pokeweed antiviral protein, gelonin, diphtherin toxin, *Pseudomonas* exotoxin, *Pseudomonas* endotoxin, Ranpirnase (Rap), Rap (N69Q), PE38, dgA, DT390, PLC, tPA, a cytokine, a growth factor, a soluble receptor component, surfactant protein D, IL-4, sIL-4R, sIL-13R, $VEGF_{121}$, TPO, EPO, a clot-dissolving agent, an enzyme, a fluorescent protein, sTNFα-R, an avimer, a scFv, a dsFv or a nanobody.

In other embodiments, an anti-angiogenic agent may form part or all of a precursor or may be attached to a stably tethered structure. Exemplary anti-angiogenic agents of use include angiostatin, baculostatin, canstatin, maspin, anti-VEGF antibodies or peptides, anti-placental growth factor antibodies or peptides, anti-Flk-1 antibodies, anti-Flt-1 antibodies or peptides, laminin peptides, fibronectin peptides, plasminogen activator inhibitors, tissue metalloproteinase inhibitors, interferons, interleukin 12, IP-10, Gro-β, thrombospondin, 2-methoxyoestradiol, proliferin-related protein, carboxiamidotriazole, CM101, Marimastat, pentosan polysulphate, angiopoietin 2, interferon-alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline.

In still other embodiments, one or more therapeutic agents, such as aplidin, azaribine, anastrozole, azacytidine, bleomycin, bortezomib, bryostatin-1, busulfan, calicheamycin, camptothecin, 10-hydroxycamptothecin, carmustine, CELEBREX®, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, 2-pyrrolinodoxorubicine (2P-DOX), cyano-morpholino doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, testosterone propionate, thalidomide, thioguanine, thiotepa, teniposide, topotecan, uracil mustard, VELCADE®, vinblastine, vinorelbine, vincristine, ricin, abrin, ribonuclease, ONCONASE®, rapLR1, DNase I, Staphylococcal enterotoxin-A, pokeweed antiviral protein, gelonin, diphtheria toxin, *Pseudomonas* exotoxin, *Pseudomonas* endotoxin, an antisense oligonucleotide, an interference RNA, or a combination thereof, may be conjugated to or incorporated into a stably tethered structure.

In various embodiments, one or more effectors, such as a diagnostic agent, a therapeutic agent, a chemotherapeutic agent, a radioisotope, an imaging agent, an anti-angiogenic agent, a cytokine, a chemokine, a growth factor, a drug, a prodrug, an enzyme, a binding molecule, a ligand for a cell surface receptor, a chelator, an immunomodulator, an oligonucleotide, a hormone, a photodetectable label, a dye, a peptide, a toxin, a contrast agent, a paramagnetic label, an ultrasound label, a pro-apoptotic agent, a liposome, a nanoparticle or a combination thereof, may be attached to a stably tethered structure.

Various embodiments may concern stably tethered structures and methods of use of same that are of use to induce apoptosis of diseased cells. Further details may be found in U.S. Patent Application Publication No. 20050079184, the entire text of which is incorporated herein by reference. Such structures may comprise a first and/or second precursor with binding affinity for an antigen selected from the group consisting of CD2, CD3, CD8, CD10, CD21, CD23, CD24, CD25, CD30, CD33, CD37, CD38, CD40, CD48, CD52, CD55, CD59, CD70, CD74, CD80, CD86, CD138, CD147, HLA-DR, CEA, CSAp, CA-125, TAG-72, EFGR, HER2, HER3, HER4, IGF-1R, c-Met, PDGFR, MUC1, MUC2, MUC3, MUC4, TNFR1, TNFR2, NGFR, Fas (CD95), DR3, DR4, DR5, DR6, VEGF, PlGF, ED-B fibronectin, tenascin, PSMA, PSA, carbonic anhydrase IX, and IL-6. In more particular embodiments, a stably tethered structure of use to induce apoptosis may comprise monoclonal antibodies, Fab fragments, chimeric, humanized or human antibodies or fragments. In preferred embodiments, the stably tethered structure may comprise combinations of anti-CD74 X anti-CD20, anti-CD74 X anti-CD22, anti-CD22 X anti-CD20, anti-CD20 X anti-HLA-DR, anti-CD19 X anti-CD20, anti-CD20 X anti-CD80, anti-CD2 X anti-CD25, anti-CD8 X anti-CD25, and anti-CD2 X anti-CD147. In more preferred embodiments, the chimeric, humanized or human antibodies or antibody fragments may be derived from the variable domains of LL2 (anti-CD22), LL1 (anti-CD74) and A20 (anti-CD20).

BRIEF DESCRIPTION OF THE DRAWINGS

FIG. 1 shows two exemplary DDD sequences. The underlined sequence in DDD1 (SEQ ID NO:1) corresponds to the first 44 amino-terminal residues found in the RIIα of human PKA. DDD2 (SEQ ID NO:2) differs from DDD1 in the two amino acid residues at the N-terminus.

FIG. 5 shows the peptide sequence for AD1-C (SEQ ID NO:3).

FIG. 23 shows that the tetravalent C-DDD2-Fab-hMN-14 consists of four functional CEA-binding Fab fragments. The conditions of SE-HPLC were the same as described for FIG. 22. (a) When WI2 Fab' was mixed with the tetravalent C-DDD2-Fab-hMN-14 at 1:1 molar ratio, four protein peaks representing the binding of the tetravalent C-DDD2-Fab-hMN-14 to one (indicated as 1, at 18.32 min), two (indicated as 2, at 17.45 min) or three (indicated as 3, at 16.92 min) WI2 Fab' fragments as well as the unbound form of C-DDD2-Fab-hMN-14 were observed. (b) When WI2 Fab' was mixed with the tetravalent C-DDD2-Fab-hMN-14 at 5:1 molar ratio, only the complex consisting of the tetravalent C-DDD2-Fab-hMN-14 bound to four WI2 Fab fragment's was observed (indicated as 4) at 16.24 min. Excess WI2 Fab' (indicated as W) was detected at 24.17 min peak.

DESCRIPTION OF ILLUSTRATIVE EMBODIMENTS

Figure 2:
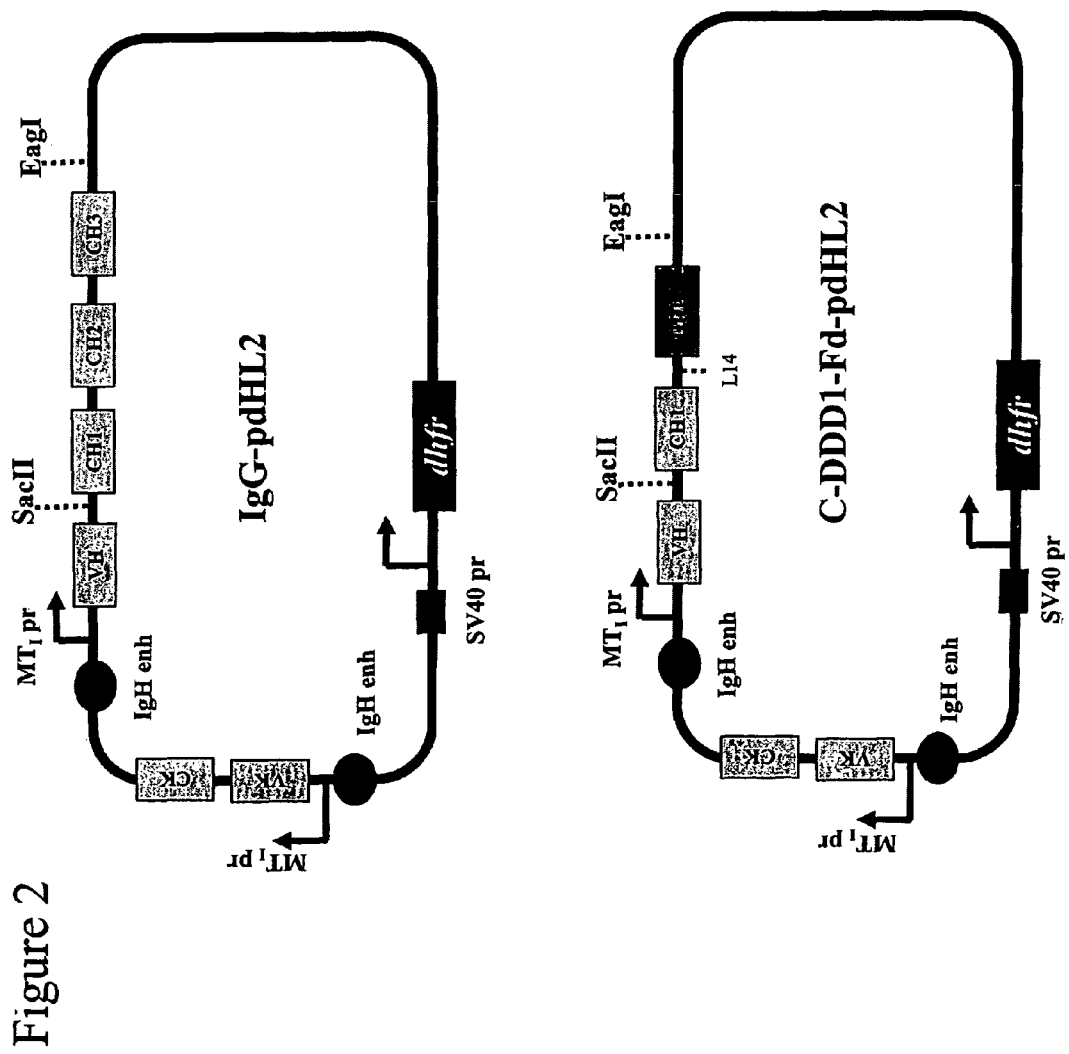
FIG. 2 shows a schematic diagram for pdHL2-based expression vectors for IgG (upper panel) and C-DDD1-Fab (lower panel).

All documents, or portions of documents, cited in this application, including but not limited to patents, patent applications, articles, books, and treatises, are hereby expressly incorporated by reference in their entirety.

Definitions

As used herein, "a" or "an" may mean one or more than one of an item.

As used herein, the terms "and" and "or" may be used to mean either the conjunctive or disjunctive. That is, both terms should be understood as equivalent to "and/or" unless otherwise stated.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion or analog of an immunoglobulin molecule, like an antibody fragment.

An antibody fragment is a portion of an antibody such as F(ab)$_2$, F(ab')$_2$, Fab, Fv, sFv and the like. Regardless of structure, an antibody fragment binds with the same antigen that is recognized by the intact antibody. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units (CDR) consisting of the amino acid residues that mimic the hypervariable region.

An effector is an atom, molecule, or compound that brings about a chosen result. An effector may include a therapeutic agent and/or a diagnostic agent.

A therapeutic agent is an atom, molecule, or compound that is useful in the treatment of a disease. Examples of therapeutic agents include antibodies, antibody fragments, drugs, toxins, enzymes, nucleases, hormones, immunomodulators, antisense oligonucleotides, small interfering RNA (siRNA), chelators, boron compounds, photoactive agents, dyes, and radioisotopes. Other exemplary therapeutic agents and methods of use are disclosed in U.S. Patent Publication Nos. 20050002945, 20040018557, 20030148409 and 20050014207, each incorporated herein by reference.

A diagnostic agent is an atom, molecule, or compound that is useful in diagnosing a disease. Useful diagnostic agents include, but are not limited to, radioisotopes, dyes (such as with the biotin-streptavidin complex), contrast agents, fluorescent compounds or molecules, and enhancing agents (e.g., paramagnetic ions) for magnetic resonance imaging (MRI).

An immunoconjugate is a conjugate of a binding molecule (e.g., an antibody component) with an atom, molecule, or a higher-ordered structure (e.g., with a carrier, a therapeutic agent, or a diagnostic agent).

A naked antibody is an antibody that is not conjugated to any other agent.

A carrier is an atom, molecule, or higher-ordered structure that is capable of associating with a therapeutic or diagnostic agent to facilitate delivery of such agent to a targeted cell. Carriers may include lipids (e.g., amphiphilic lipids that are capable of forming higher-ordered structures), polysaccharides (such as dextran), or other higher-ordered structures, such as micelles, liposomes, or nanoparticles.

As used herein, the term antibody fusion protein is a recombinantly produced antigen-binding molecule in which two or more of the same or different scFv or antibody fragments with the same or different specificities are linked. Valency of the fusion protein indicates how many binding arms or sites the fusion protein has to a single antigen or epitope; i.e., monovalent, bivalent, trivalent or multivalent. The multivalency of the antibody fusion protein means that it can take advantage of multiple interactions in binding to an antigen, thus increasing the avidity of binding to the antigen. Specificity indicates how many antigens or epitopes an antibody fusion protein is able to bind; i.e., monospecific, bispecific, trispecific, multispecific. Using these definitions, a natural antibody, e.g., an IgG, is bivalent because it has two binding arms but is monospecific because it binds to one epitope. Monospecific, multivalent fusion proteins have more than one binding site for an epitope but only binds to one such epitope, for example a diabody with two binding site reactive with the same antigen. The fusion protein may comprise a single antibody component, a multivalent or multispecific combination of different antibody components, or multiple copies of the same antibody component. The fusion protein may additionally comprise an antibody or an antibody fragment and a therapeutic agent. Examples of therapeutic agents suitable for such fusion proteins include immunomodulators ("antibody-immunomodulator fusion protein") and toxins ("antibody-toxin fusion protein"). One preferred toxin comprises a ribonuclease (RNase), preferably a recombinant RNase.

An antibody or immunoconjugate preparation, or a composition described herein, is said to be administered in a "therapeutically effective amount" if the amount administered is physiologically significant. An agent is physiologically significant if its presence results in a detectable change in the physiology of a recipient mammal. In particular, an antibody preparation is physiologically significant if its presence invokes an antitumor response or mitigates the signs and symptoms of an autoimmune disease state. A physiologically significant effect could also be the evocation of a humoral and/or cellular immune response in the recipient mammal leading to growth inhibition or death of target cells.

Conjugates of the Stably Tethered Structures

Additional moieties can be conjugated to the stably tethered structures described above. For example, drugs, toxins, radioactive compounds, enzymes, hormones, cytotoxic proteins, chelates, cytokines, and other functional agents may be conjugated to the stably tethered structures. Conjugation can be via, for example, covalent attachments to amino acid residues containing amine, carboxyl, thiol or hydroxyl groups in the side-chains. Various conventional linkers may be used for this purpose, for example, diisocyanates, diisothiocyanates, bis(hydroxysuccinimide) esters, carbodiimides, maleimide-hydroxysuccinimide esters, glutaraldehyde and the like. Conjugation of agents to the stably tethered structures preferably does not significantly affect the activity of each subunit contained in the unmodified structures. Conjugation can be carried out separately to the $a_4$ and $a'_4$ constructs and the resulting conjugates are used for preparing the $a_2a'_2$ constructs In addition, cytotoxic agents may be first coupled to a polymeric carrier, which is then conjugated to a stably tethered structure. For this method, see Ryser et al., Proc. Natl. Acad. Sci. USA, 75:3867-3870, 1978; U.S. Pat. No. 4,699,784 and U.S. Pat. No. 4,046,722, which are incorporated herein by reference.

The conjugates described herein can be prepared by various methods known in the art. For example, a stably tethered structure can be radiolabeled with $^{131}I$ and conjugated to a lipid, such that the resulting conjugate can form a liposome. The liposome may incorporate one or more therapeutic (e.g., a drug such as FUdR-dO) or diagnostic agents. Alternatively, in addition to the carrier, a stably tethered structure may be conjugated to $^{131}I$ (e.g., at a tyrosine residue) and a drug (e.g., at the epsilon amino group of a lysine residue), and the carrier may incorporate an additional therapeutic or diagnostic agent. Therapeutic and diagnostic agents may be covalently associated with one or more than one subunit of the stably tethered structures.

The formation of liposomes and micelles is known in the art. See, e.g., Wrobel and Collins, Biochimica et Biophysica Acta (1995), 1235: 296-304; Lundberg et al., J. Pharm. Pharmacol. (1999), 51:1099-1105; Lundberg et al., Int. J. Pharm. (2000), 205:101-108; Lundberg, J. Pharm. Sci. (1994), 83:72-75; Xu et al., Molec. Cancer Ther. (2002), 1:337-346; Torchilin et al., Proc. Nat'l. Acad. Sci., U.S.A. (2003), 100: 6039-6044; U.S. Pat. No. 5,565,215; U.S. Pat. No. 6,379,698; and U.S. 2003/0082154.

Nanoparticles or nanocapsules formed from polymers, silica, or metals, which are useful for drug delivery or imaging, have been described as well. See, e.g., West et al., Applications of Nanotechnology to Biotechnology (2000), 11:215-217; U.S. Pat. No. 5,620,708; U.S. Pat. No. 5,702,727; and U.S. Pat. No. 6,530,944. The conjugation of antibodies or binding molecules to liposomes to form a targeted carrier for therapeutic or diagnostic agents has been described. See, e.g., Bendas, Biodrugs (2001), 15:215-224; Xu et al., Mol. Cancer Ther (2002), 1:337-346; Torchilin et al., Proc. Nat'l. Acad. Sci. U.S.A (2003), 100:6039-6044; Bally, et al., J. Liposome Res. (1998), 8:299-335; Lundberg, Int. J. Pharm. (1994), 109:73-81; Lundberg, J. Pharm. Pharmacol. (1997), 49:16-21; Lundberg, Anti-cancer Drug Design (1998), 13: 453-461.

See also U.S. Pat. No. 6,306,393; U.S. Ser. No. 10/350,096; U.S. Ser. No. 09/590,284, and U.S. Ser. No. 60/138,284, filed Jun. 9, 1999. All these references are incorporated herein by reference.

A wide variety of diagnostic and therapeutic agents can be advantageously used to form the conjugates of the stably tethered structures, or may be linked to haptens that bind to a recognition site on the stably tethered structures. Diagnostic agents may include radioisotopes, enhancing agents for use in MRI or contrast agents for ultrasound imaging, and fluorescent compounds. Many appropriate imaging agents are known in the art, as are methods for their attachment to proteins or peptides (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the protein or peptide (U.S. Pat. No. 4,472,509).

In order to load a stably tethered structure with radioactive metals or paramagnetic ions, it may be necessary to first react it with a carrier to which multiple copies of a chelating group for binding the radioactive metals or paramagnetic ions have been attached. Such a carrier can be a polylysine, polysaccharide, or a derivatized or derivatizable polymeric substance having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and the like known to be useful for this purpose. Carriers containing chelates are coupled to the stably tethered structure using standard chemistries in a way to minimize aggregation and loss of immunoreactivity.

Other, more unusual, methods and reagents that may be applied for preparing such conjugates are disclosed in U.S. Pat. No. 4,824,659, which is incorporated herein in its entirety by reference. Particularly useful metal-chelate combinations include 2-benzyl-DTPA and its monomethyl and cyclohexyl analogs, used with diagnostic isotopes in the general energy range of 60 to 4,000 keV. Some useful diagnostic nuclides may include $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94}$Tc, $^{94m}$Tc, $^{99m}$Tc, or $^{111}$In. The same chelates complexed with non-radioactive metals, such as manganese, iron and gadolinium, are useful for MRI, when used along with the stably tethered structures and carriers described herein. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates, such as macrocyclic polyethers for complexing $^{223}$Ra, may be used.

Therapeutic agents include, for example, chemotherapeutic drugs such as vinca alkaloids, anthracyclines, epidophyllotoxins, taxanes, antimetabolites, alkylating agents, antibiotics, Cox-2 inhibitors, antimitotics, antiangiogenic and proapoptotic agents, particularly doxorubicin, methotrexate, TAXOL®, CPT-11, camptothecans, and others from these and other classes of anticancer agents, and the like. Other cancer chemotherapeutic drugs include nitrogen mustards, alkyl sulfonates, nitrosoureas, triazenes, folic acid analogs, pyrimidine analogs, purine analogs, platinum coordination complexes, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art, and may be conjugated to the stably tethered structures described herein using methods that are known in the art.

Another class of therapeutic agents consists of radionuclides that emit α-particles (such as $^{212}$Pb, $^{212}$Bi, $^{213}$Bi, $^{211}$At, $^{223}$Ra, $^{225}$Ac), β-particles (such as $^{32}$P, $^{33}$P, $^{47}$Sc, $^{67}$Cu, $^{67}$Ga, $^{89}$Sr, $^{90}$Y, $^{111}$Ag, $^{125}$I, $^{131}$I, $^{142}$Pr, $^{153}$Sm, $^{161}$Tb, $^{166}$Ho, $^{166}$Dy, $^{177}$Lu, $^{186}$Re, $^{188}$Re, $^{189}$Re), or Auger electrons (such as $^{111}$In, $^{125}$I, $^{67}$Ga, $^{191}$Os, $^{193m}$Pt, $^{195m}$Pt, $^{195m}$Hg). The stably tethered structures may be labeled with one or more of the above radionuclides using methods as described for the diagnostic agents.

A suitable peptide containing a detectable label (e.g., a fluorescent molecule), or a cytotoxic agent, (e.g., a radioiodine), can be covalently, non-covalently, or otherwise associated with the stably tethered structures. For example, a therapeutically useful conjugate can be obtained by incorporating a photoactive agent or dye onto the stably tethered structures. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy. See Jori et al. (eds.), PHOTODYNAMIC THERAPY OF TUMORS AND OTHER DISEASES (Libreria Progetto 1985); van den Bergh, Chem. Britain (1986), 22:430. Moreover, monoclonal antibodies have been coupled with photoactivated dyes for achieving phototherapy. See Mew et al., J. Immunol. (1983), 130:1473; idem., Cancer Res. (1985), 45:4380; Oseroff et al., Proc. Natl. Acad. Sci. USA (1986), 83:8744; idem., Photochem. Photobiol. (1987), 46:83; Hasan et al., Prog. Clin. Biol. Res. (1989), 288:471; Tatsuta et al., Lasers Surg. Med. (1989), 9:422; Pelegrin et al., Cancer (1991), 67:2529. Endoscopic applications are also contemplated. Endoscopic methods of detection and therapy are described in U.S. Pat. Nos. 4,932,412; 5,525,338; 5,716,595; 5,736,119; 5,922,302; 6,096,289; and U.S. Pat. No. 6,387,350, which are incorporated herein by reference in their entirety.

In certain embodiments, the novel constructs and methods disclosed herein are useful for targeted delivery of RNAi for therapeutic intervention. The delivery vehicle can be either an a2 (dimer) or an a4 (tetramer) structure with an internalizing antibody binding domain fused to human protamine (peptide of ~50 amino acid residues) as its precursor. An example of an a2 construct would be VH—CH1-hP1-DDD1//VL-CL or VH—CH1-hP2-DDD1//VL-CL, where hP1 and hP2 are human protamine 1 and human protamine 2, respectively; both capable of forming stable DNA complexes for in vivo applications (Nat Biotechnol. 23: 709-717, 2005; Gene Therapy. 13: 194-195, 2006). An example of an a4 construct would be VH—CH1-hP1-DDD2//VL-CL or VH—CH1-hP2-DDD2//VL-CL, which would provide four active Fab fragments, each carrying a human protamine for binding to RNAi. The multivalent complex will facilitate the binding to and receptor-mediated internalization into target cells, where the noncovalently bound RNAi is dissociated in the endosomes and released into cytoplasm. As no redox chemistry is involved, the existence of 3 intramolecular disulfide bonds in hP1 or hP2 does not present a problem. In addition to delivery of RNAi, these constructs may also be of use for targeted delivery of therapeutic genes or DNA vaccines. Another area of use is to apply the A4/A2 technology for producing intrabodies, which is the protein analog of RNAi in terms of function.

Peptide Administration

Various embodiments of the claimed methods and/or compositions may concern one or more peptide based stably tethered structures to be administered to a subject. Administration may occur by any route known in the art, including but not limited to oral, nasal, buccal, inhalational, rectal, vaginal, topical, orthotopic, intradermal, subcutaneous, intramuscular, intraperitoneal, intraarterial, intrathecal or intravenous injection.

Unmodified peptides administered orally to a subject can be degraded in the digestive tract and depending on sequence and structure may exhibit poor absorption across the intestinal lining. However, methods for chemically modifying peptides to render them less susceptible to degradation by endogenous proteases or more absorbable through the alimentary tract are well known (see, for example, Blondelle et al., 1995, Biophys. J. 69:604-11; Ecker and Crooke, 1995, Biotechnology 13:351-69; Goodman and Ro, 1995, BURGER'S MEDICINAL CHEMISTRY AND DRUG DISCOVERY, VOL. I, ed. Wolff, John Wiley & Sons; Goodman and Shao, 1996, Pure & Appl. Chem. 68:1303-08). Methods for preparing libraries of peptide analogs, such as peptides containing D-amino acids; peptidomimetics consisting of organic molecules that mimic the structure of a peptide; or peptoids such as vinylogous peptoids, have also been described and may be used to construct peptide based stably tethered structures suitable for oral administration to a subject.

In certain embodiments, the standard peptide bond linkage may be replaced by one or more alternative linking groups, such as $CH_2$—NH, $CH_2$—S, $CH_2$—$CH_2$, CH=CH, CO—$CH_2$, CHOH—$CH_2$ and the like. Methods for preparing peptide mimetics are well known (for example, Hruby, 1982, *Life Sci* 31:189-99; Holladay et al., 1983, *Tetrahedron Lett.* 24:4401-04; Jennings-White et al., 1982, *Tetrahedron Lett.* 23:2533; Almquiest et al., 1980, *J. Med. Chem.* 23:1392-98; Hudson et al., 1979, *Int. J. Pept. Res.* 14:177-185; Spatola et al., 1986, *Life Sci* 38:1243-49; U.S. Pat. Nos. 5,169,862; 5,539,085; 5,576,423, 5,051,448, 5,559,103, each incorporated herein by reference.) Peptide mimetics may exhibit enhanced stability and/or absorption in vivo compared to their peptide analogs.

Alternatively, peptides may be administered by oral delivery using N-terminal and/or C-terminal capping to prevent exopeptidase activity. For example, the C-terminus may be capped using amide peptides and the N-terminus may be capped by acetylation of the peptide. Peptides may also be cyclized to block exopeptidases, for example by formation of cyclic amides, disulfides, ethers, sulfides and the like.

Peptide stabilization may also occur by substitution of D-amino acids for naturally occurring L-amino acids, particularly at locations where endopeptidases are known to act. Endopeptidase binding and cleavage sequences are known in the art and methods for making and using peptides incorporating D-amino acids have been described (e.g., U.S. Patent Application Publication No. 20050025709, McBride et al., filed Jun. 14, 2004, incorporated herein by reference). In certain embodiments, peptides and/or proteins may be orally administered by co-formulation with proteinase- and/or peptidase-inhibitors.

Other methods for oral delivery of therapeutic peptides are disclosed in Mehta ("Oral delivery and recombinant production of peptide hormones," June 2004, *BioPharm International*). The peptides are administered in an enteric-coated solid dosage form with excipients that modulate intestinal proteolytic activity and enhance peptide transport across the intestinal wall. Relative bioavailability of intact peptides using this technique ranged from 1% to 10% of the administered dosage. Insulin has been successfully administered in dogs using enteric-coated microcapsules with sodium cholate and a protease inhibitor (Ziv et al., 1994, *J. Bone Miner. Res.* 18 (Suppl. 2):792-94. Oral administration of peptides has been performed using acylcarnitine as a permeation enhancer and an enteric coating (Eudragit L30D-55, Rohm Pharma Polymers, see Mehta, 2004). Excipients of use for orally administered peptides may generally include one or more inhibitors of intestinal proteases/peptidases along with detergents or other agents to improve solubility or absorption of the peptide, which may be packaged within an enteric-coated capsule or tablet (Mehta, 2004). Organic acids may be included in the capsule to acidify the intestine and inhibit intestinal protease activity once the capsule dissolves in the intestine (Mehta, 2004). Another alternative for oral delivery of peptides would include conjugation to polyethylene glycol (PEG)-based amphiphilic oligomers, increasing absorption and resistance to enzymatic degradation (Soltero and Ekwuribe, 2001, *Pharm. Technol.* 6:110).

In still other embodiments, peptides may be modified for oral or inhalational administration by conjugation to certain proteins, such as the Fc region of IgG1 (see Examples 3-7). Methods for preparation and use of peptide-Fc conjugates are disclosed, for example, in Low et al. (2005, *Hum. Reprod.* 20:1805-13) and Dumont et al. (2005, *J. Aerosol. Med.* 18:294-303), each incorporated herein by reference. Low et al. (2005) disclose the conjugation of the alpha and beta subunits of FSH to the Fc region of IgG1 in single chain or heterodimer form, using recombinant expression in CHO cells. The Fc conjugated peptides were absorbed through epithelial cells in the lung or intestine by the neonatal Fc receptor mediated transport system. The Fc conjugated peptides exhibited improved stability and absorption in vivo compared to the native peptides. It was also observed that the heterodimer conjugate was more active than the single chain form.

Proteins and Peptides

A variety of polypeptides or proteins may be used within the scope of the claimed methods and compositions. In certain embodiments, the proteins may comprise antibodies or fragments of antibodies containing an antigen-binding site. As used herein, a protein, polypeptide or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide" and "peptide" are used interchangeably herein. Accordingly, the term "protein or peptide" encompasses amino acid sequences comprising at least one of the 20 common amino acids found in naturally occurring proteins, or at least one modified or unusual amino acid.

As used herein, an "amino acid residue" refers to any naturally occurring amino acid, any amino acid derivative or any amino acid mimic known in the art. In certain embodiments, the residues of the protein or peptide are sequential, without any non-amino acid interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid, including but not limited to those shown below.

| Modified and Unusual Amino Acids | | | |
|---|---|---|---|
| Abbr. | Amino Acid | Abbr. | Amino Acid |
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed and may be found at computerized databases known to those of ordinary skill in the art. One such database is the National Center for Biotechnology Information's Genbank and GenPept databases (www.ncbi.nlm.nih.gov/). The coding regions for known genes may be amplified and/or expressed using the techniques disclosed herein or as would be know to those of ordinary skill in the art. Alternatively, various commercial preparations of proteins, polypeptides, and peptides are known to those of skill in the art.

Peptide Mimetics

Another embodiment for the preparation of polypeptides is the use of peptide mimetics. Mimetics are peptide-containing molecules that mimic elements of protein secondary structure. See, for example, Johnson et al., "Peptide Turn Mimetics" in BIOTECHNOLOGY AND PHARMACY, Pezzuto et al., Eds., Chapman and Hall, New York (1993), incorporated herein by reference. The rationale behind the use of peptide mimetics is that the peptide backbone of proteins exists chiefly to orient amino acid side chains so as to facilitate molecular interactions, such as those of antibody and antigen. A peptide mimetic is expected to permit molecular interactions similar to the natural molecule.

Fusion Proteins

Various embodiments may concern fusion proteins. These molecules generally have all or a substantial portion of a peptide, linked at the N- or C-terminus, to all or a portion of a second polypeptide or protein. Methods of generating fusion proteins are well known to those of skill in the art. Such proteins may be produced, for example, by chemical attachment using bifunctional cross-linking reagents, by de novo synthesis of the complete fusion protein, or by attachment of a DNA sequence encoding a first protein or peptide to a DNA sequence encoding a second peptide or protein, followed by expression of the intact fusion protein.

Synthetic Peptides

Proteins or peptides may be synthesized, in whole or in part, in solution or on a solid support in accordance with conventional techniques. Various automatic synthesizers are commercially available and can be used in accordance with known protocols. See, for example, Stewart and Young, (1984, Solid Phase Peptide Synthesis, 2d. ed., Pierce Chemical Co.); Tam et al., (1983, J. Am. Chem. Soc., 105:6442); Merrifield, (1986, Science, 232: 341-347); and Barany and Merrifield (1979, The Peptides, Gross and Meienhofer, eds., Academic Press, New York, pp. 1-284). Short peptide sequences, usually from about 6 up to about 35 to 50 amino acids, can be readily synthesized by such methods. Alternatively, recombinant DNA technology may be employed wherein a nucleotide sequence which encodes a peptide of interest is inserted into an expression vector, transformed or transfected into an appropriate host cell, and cultivated under conditions suitable for expression.

Antibodies

Various embodiments may concern antibodies for a target. The term "antibody" is used herein to refer to any antibody-like molecule that has an antigen binding region, and includes antibody fragments such as Fab', Fab, F(ab')$_2$, single domain antibodies (DABs), Fv, scFv (single chain Fv), and the like. Techniques for preparing and using various antibody-based constructs and fragments are well known in the art. Means for preparing and characterizing antibodies are also well known in the art (See, e.g., Harlowe and Lane, 1988, Antibodies: A Laboratory Manual, Cold Spring Harbor Laboratory). Antibodies of use may also be commercially obtained from a wide variety of known sources. For example, a variety of antibody secreting hybridoma lines are available from the American Type Culture Collection (ATCC, Manassas, Va.).

Production of Antibody Fragments

Some embodiments of the claimed methods and/or compositions may concern antibody fragments. Such antibody fragments may be obtained by pepsin or papain digestion of whole antibodies by conventional methods. For example, antibody fragments may be produced by enzymatic cleavage of antibodies with pepsin to provide F(ab')$_2$ fragments. This fragment may be further cleaved using a thiol reducing agent and, optionally, followed by a blocking group for the sulfhydryl groups resulting from cleavage of disulfide linkages, to produce Fab' monovalent fragments. Alternatively, an enzymatic cleavage using papain n produces two monovalent Fab fragments and an Fc fragment. Exemplary methods for producing antibody fragments are disclosed in U.S. Pat. No. 4,036,945; U.S. Pat. No. 4,331,647; Nisonoff et al., 1960, Arch. Biochem. Biophys., 89:230; Porter, 1959, Biochem. J., 73:119; Edelman et al., 1967, METHODS IN ENZYMOLOGY, page 422 (Academic Press), and Coligan et al. (eds.), 1991, CURRENT PROTOCOLS IN IMMUNOLOGY, (John Wiley & Sons).

Other methods of cleaving antibodies, such as separation of heavy chains to form monovalent light-heavy chain fragments, further cleavage of fragments or other enzymatic, chemical or genetic techniques also may be used, so long as the fragments bind to the antigen that is recognized by the intact antibody. For example, Fv fragments comprise an association of $V_H$ and $V_L$ chains. This association can be noncovalent, as described in Inbar et al., 1972, Proc. Nat'l. Acad. Sci. USA, 69:2659. Alternatively, the variable chains may be linked by an intermolecular disulfide bond or cross-linked by chemicals such as glutaraldehyde. See Sandhu, 1992, Crit. Rev. Biotech., 12:437.

Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains, connected by an oligonucleotides linker sequence. The structural gene is inserted into an expression vector that is subsequently introduced into a host cell, such as

*E. coli*. The recombinant host cells synthesize a single polypeptide chain with a linker peptide bridging the two V domains. Methods for producing sFv's are well-known in the art. See Whitlow et al., 1991, Methods: A Companion to Methods in Enzymology 2:97; Bird et al., 1988, Science, 242:423; U.S. Pat. No. 4,946,778; Pack et al., 1993, Bio/Technology, 11:1271, and Sandhu, 1992, Crit. Rev. Biotech., 12:437.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See Larrick et al., 1991, Methods: A Companion to Methods in Enzymology 2:106; Ritter et al. (eds.), 1995, MONOCLONAL ANTIBODIES: PRODUCTION, ENGINEERING AND CLINICAL APPLICATION, pages 166-179 (Cambridge University Press); Birch et al., (eds.), 1995, MONOCLONAL ANTIBODIES: PRINCIPLES AND APPLICATIONS, pages 137-185 (Wiley-Liss, Inc.).

Chimeric and Humanized Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, Hybridoma 13:469).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. The affinity of humanized antibodies for a target may also be increased by selected modification of the CDR sequences (WO0029584A1). Techniques for production of humanized monoclonal antibodies are well known in the art. (See, e.g., Jones et al., 1986, Nature, 321:522; Riechmann et al., Nature, 1988, 332:323; Verhoeyen et al., 1988, Science, 239:1534; Carter et al., 1992, Proc. Nat'l Acad. Sci. USA, 89:4285; Sandhu, Crit. Rev. Biotech., 1992, 12:437; Tempest et al., 1991, Biotechnology 9:266; Singer et al., J. Immunol., 1993, 150:2844.)

Other embodiments may concern non-human primate antibodies. General techniques for raising therapeutically useful antibodies in baboons may be found, for example, in Goldenberg et al., WO 91/11465 (1991), and in Losman et al., Int. J. Cancer 46: 310 (1990).

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the μ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97, incorporated herein by reference). Library construction was performed according to Andris-Widhopf et al. (2000, In: *Phage Display Laboratory Manual*, Barbas et al. (eds), $1^{st}$ edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods, as known in the art. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols. A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along accessory genes and regulatory sequences. The human variable region repertoire may be used to generate antibody producing B cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Such human antibodies may be coupled to other molecules by chemical cross-linking or other known methodologies. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Pre-Targeting

One strategy for use of bi-specific stably tethered constructs includes pre-targeting methodologies, in which an effector molecule is administered to a subject after a bi-specific construct has been administered. The bi-specific construct, which would include a binding site for an effector, hapten or carrier and one for the diseased tissue, localizes to the diseased tissue and increases the specificity of localization of the effector to the diseased tissue (U.S. Patent Application No. 20050002945). Because the effector molecule may be cleared from circulation much more rapidly than the bi-specific construct, normal tissues may have a decreased exposure to the effector molecule when a pre-targeting strategy is used than when the effector molecule is directly linked to the disease targeting antibody.

Pre-targeting methods have been developed to increase the target:background ratios of detection or therapeutic agents. Examples of pre-targeting and biotin/avidin approaches are described, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256,395; Stickney et al., Cancer Res. 51:6650, 1991; Yuan et al., Cancer Res. 51:3119, 1991; U.S. Pat. Nos. 6,077,499; 09/597,580; 10/361,026; 09/337,756; 09/823,746; 10/116,116; 09/382,186; 10/150,654; 6,090,381; 6,472,511; 10/114,315; U.S. Provisional Application No. 60/386,411; U.S. Provisional Application No. 60/345,641; U.S. Provisional Application No. 60/3328,835; U.S. Provisional Application No. 60/426,379; U.S. Ser. Nos. 09/823,746; 09/337,756; and U.S. Provisional Application No. 60/342,103, all of which are incorporated herein by reference.

In certain embodiments, bi-specific constructs and targetable constructs may be of use in treating and/or imaging normal or diseased tissue and organs, for example using the methods described in U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, each incorporated by reference. Additional methods are described in U.S. application Ser. No. 09/337,756 filed Jun. 22, 1999 and in U.S. application Ser. No. 09/823,746, filed Apr. 3, 2001.

Aptamers

In certain embodiments, a precursor for construct formation may comprise an aptamer. Methods of constructing and determining the binding characteristics of aptamers are well known in the art. For example, such techniques are described in U.S. Pat. Nos. 5,582,981, 5,595,877 and 5,637,459, each incorporated herein by reference.

Aptamers may be prepared by any known method, including synthetic, recombinant, and purification methods, and may be used alone or in combination with other ligands specific for the same target. In general, a minimum of approximately 3 nucleotides, preferably at least 5 nucleotides, are necessary to effect specific binding. Aptamers of sequences shorter than 10 bases may be feasible, although aptamers of 10, 20, 30 or 40 nucleotides may be preferred.

Aptamers need to contain the sequence that confers binding specificity, but may be extended with flanking regions and otherwise derivatized. In preferred embodiments, the binding sequences of aptamers may be flanked by primer-binding sequences, facilitating the amplification of the aptamers by PCR or other amplification techniques. In a further embodiment, the flanking sequence may comprise a specific sequence that preferentially recognizes or binds a moiety to enhance the immobilization of the aptamer to a substrate.

Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. One or more phosphodiester linkages may be replaced by alternative linking groups, such as P(O)O replaced by P(O)S, P(O)NR$_2$, P(O)R, P(O)OR', CO, or CNR$_2$, wherein R is H or alkyl (1-20C) and R' is alkyl (1-20C); in addition, this group may be attached to adjacent nucleotides through O or S. Not all linkages in an oligomer need to be identical.

Methods for preparation and screening of aptamers that bind to particular targets of interest are well known, for example U.S. Pat. No. 5,475,096 and U.S. Pat. No. 5,270,163, each incorporated by reference. The technique generally involves selection from a mixture of candidate aptamers and step-wise iterations of binding, separation of bound from unbound aptamers and amplification. Because only a small number of sequences (possibly only one molecule of aptamer) corresponding to the highest affinity aptamers exist in the mixture, it is generally desirable to set the partitioning criteria so that a significant amount of aptamers in the mixture (approximately 5-50%) is retained during separation. Each cycle results in an enrichment of aptamers with high affinity for the target. Repetition for between three to six selection and amplification cycles may be used to generate aptamers that bind with high affinity and specificity to the target.

Avimers

In certain embodiments, the precursors, components and/or complexes described herein may comprise one or more avimer sequences. Avimers are a class of binding proteins somewhat similar to antibodies in their affinities and specificities for various target molecules. They were developed from human extracellular receptor domains by in vitro exon shuffling and phage display. (Silverman et al., 2005, Nat. Biotechnol. 23:1493-94; Silverman et al., 2006, Nat. Biotechnol. 24:220.) The resulting multidomain proteins may comprise multiple independent binding domains that may exhibit improved affinity (in some cases sub-nanomolar) and specificity compared with single-epitope binding proteins. (Id.) In various embodiments, avimers may be attached to, for example, DDD sequences for use in the claimed methods and compositions. Additional details concerning methods of construction and use of avimers are disclosed, for example, in U.S. Patent Application Publication Nos. 20040175756, 20050048512, 20050053973, 20050089932 and 20050221384, the Examples section of each of which is incorporated herein by reference.

Methods of Disease Tissue Detection, Diagnosis and Imaging

Protein-Based In Vitro Diagnosis

The present invention contemplates the use of stably tethered structures to screen biological samples in vitro and/or in vivo for the presence of the disease-associated antigens. In exemplary immunoassays, a stably tethered structure comprising an antibody, fusion protein, or fragment thereof may be utilized in liquid phase or bound to a solid-phase carrier, as described below. In preferred embodiments, particularly those involving in vivo administration, the antibody or fragment thereof is humanized. Also preferred, the antibody or fragment thereof is fully human. Still more preferred, the fusion protein comprises a humanized or fully human antibody. The skilled artisan will realize that a wide variety of techniques are known for determining levels of expression of a particular gene and any such known method, such as immunoassay, RT-PCR, mRNA purification and/or cDNA preparation followed by hybridization to a gene expression assay chip may be utilized to determine levels of expression in individual subjects and/or tissues. Exemplary in vitro assays of use include RIA, ELISA, sandwich ELISA, Western blot, slot blot, dot blot, and the like. Although such techniques were developed using intact antibodies, stably tethered structures that incorporate antibodies, antibody fragments or other binding moieties may be used.

Stably tethered structures incorporating antibodies, fusion proteins, antibody fragments and/or other binding moieties may also be used to detect the presence of a target antigen in tissue sections prepared from a histological specimen. Such in situ detection can be used to determine the presence of the antigen and to determine the distribution of the antigen in the examined tissue. In situ detection can be accomplished by applying a detectably-labeled structure to frozen or paraffin-embedded tissue sections. General techniques of in situ detection are well-known to those of ordinary skill. See, for example, Ponder, "Cell Marking Techniques and Their Application," in MAMMALIAN DEVELOPMENT: A PRACTICAL APPROACH 113-38 Monk (ed.) (IRL Press 1987), and Coligan at pages 5.8.1-5.8.8.

Stably tethered structures can be detectably labeled with any appropriate marker moiety, for example, a radioisotope, an enzyme, a fluorescent label, a dye, a chromogen, a chemiluminescent label, a bioluminescent label or a paramagnetic label.

The marker moiety may be a radioisotope that is detected by such means as the use of a gamma counter or a beta-scintillation counter or by autoradiography. In a preferred embodiment, the diagnostic conjugate is a gamma-, beta- or a positron-emitting isotope. A marker moiety refers to a molecule that will generate a signal under predetermined conditions. Examples of marker moieties include radioisotopes, enzymes, fluorescent labels, chemiluminescent labels, bioluminescent labels and paramagnetic labels. The binding of marker moieties to stably tethered structures can be accomplished using standard techniques known to the art. Typical methodology in this regard is described by Kennedy et al., Clin. Chim. Acta 70: 1 (1976), Schurs et al., Clin. Chim. Acta 81: 1 (1977), Shih et al., Int'l J. Cancer 46: 1101 (1990).

Nucleic Acid Based In Vitro Diagnosis

Stably tethered structures may, in some embodiments, incorporated nucleic acid moieties. In particular embodiments, nucleic acids may be analyzed to determine levels of binding, particularly using nucleic acid amplification methods. Various forms of amplification are well known in the art and any such known method may be used. Generally, amplification involves the use of one or more primers that hybridize selectively or specifically to a target nucleic acid sequence to be amplified.

The term primer, as defined herein, is meant to encompass any nucleic acid that is capable of priming the synthesis of a nascent nucleic acid in a template-dependent process. Computerized programs for selection and design of amplification primers are available from commercial and/or public sources well known to the skilled artisan. A number of template dependent processes are available to amplify the marker sequences present in a given sample. One of the best-known amplification methods is the polymerase chain reaction (referred to as PCR), which is described in detail in U.S. Pat. Nos. 4,683,195, 4,683,202 and 4,800,159. However, other methods of amplification are known and may be used.

In Vivo Diagnosis

Methods of diagnostic imaging with labeled peptides or MAbs are well-known. For example, in the technique of immunoscintigraphy, ligands or antibodies are labeled with a gamma-emitting radioisotope and introduced into a patient. A gamma camera is used to detect the location and distribution of gamma-emitting radioisotopes. See, for example, Srivastava (ed.), RADIOLABELED MONOCLONAL ANTIBODIES FOR IMAGING AND THERAPY (Plenum Press 1988), Chase, "Medical Applications of Radioisotopes," in REMINGTON'S PHARMACEUTICAL SCIENCES, 18th Edition, Gennaro et al. (eds.), pp. 624-652 (Mack Publishing Co., 1990), and Brown, "Clinical Use of Monoclonal Antibodies," in BIOTECHNOLOGY AND PHARMACY 227-49, Pezzuto et al. (eds.) (Chapman & Hall 1993). Also preferred is the use of positron-emitting radionuclides (PET isotopes), such as with an energy of 511 keV, such as $^{18}$F, $^{68}$Ga, $^{64}$Cu, and $^{124}$I. Such imaging can be conducted by direct labeling of the stably tethered structure, or by a pretargeted imaging method, as described in Goldenberg et al, "Antibody Pre-targeting Advances Cancer Radioimmunodetection and Radioimmunotherapy," (J Clin Oncol 2006; 24:823-834), see also U.S. Patent Publication Nos. 20050002945, 20040018557, 20030148409 and 20050014207, each incorporated herein by reference.

The radiation dose delivered to the patient is maintained at as low a level as possible through the choice of isotope for the best combination of minimum half-life, minimum retention in the body, and minimum quantity of isotope which will permit detection and accurate measurement. Examples of radioisotopes that are appropriate for diagnostic imaging include $^{99m}$Tc and $^{111}$In.

The stably tethered structures, or haptens or carriers that bind to them, also can be labeled with paramagnetic ions and a variety of radiological contrast agents for purposes of in vivo diagnosis. Contrast agents that are particularly useful for magnetic resonance imaging comprise gadolinium, manganese, dysprosium, lanthanum, or iron ions. Additional agents include chromium, copper, cobalt, nickel, rhenium, europium, terbium, holmium, or neodymium. ligands, antibodies and fragments thereof can also be conjugated to ultrasound contrast/enhancing agents. For example, one ultrasound contrast agent is a liposome that comprises a humanized IgG or fragment thereof. Also preferred, the ultrasound contrast agent is a liposome that is gas filled.

Imaging Agents and Radioisotopes

Many appropriate imaging agents are known in the art, as are methods for their attachment to proteins or peptides (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the protein or peptide (U.S. Pat. No. 4,472,509). Proteins or peptides also may be reacted with an enzyme in the presence of a coupling agent such as glutaraldehyde or periodate. Conjugates with fluorescein markers are prepared in the presence of these coupling agents or by reaction with an isothiocyanate.

Non-limiting examples of paramagnetic ions of potential use as imaging agents include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

Radioisotopes of potential use as imaging or therapeutic agents include astatine$^{211}$, carbon$^{14}$, chromium$^{51}$, chlorine$^{36}$, cobalt$^{57}$, cobalt$^{58}$, copper$^{62}$, copper$^{64}$, copper$^{67}$, Eu$^{152}$, fluorine$^{18}$, gallium$^{67}$, gallium$^{68}$, hydrogen$^{3}$, iodine$^{123}$, iodine$^{124}$, iodine$^{125}$, iodine$^{131}$, indium$^{111}$, iron$^{52}$, iron$^{59}$, lutetium$^{177}$, phosphorus32, phosphorus$^{33}$, rhenium$^{186}$, rhenium$^{188}$, Sc$^{47}$, selenium$^{75}$, silver$^{111}$, sulphur$^{35}$, technetium$^{94m}$, technetium$^{99m}$, yttrium$^{86}$ yttrium$^{90}$, and zirconium$^{89}$. I$^{125}$ is often being preferred for use in certain embodiments, and technetium$^{99m}$ and indium$^{111}$ are also often preferred due to their low energy and suitability for long-range detection.

Radioactively labeled proteins or peptides may be produced according to well-known methods in the art. For instance, they can be iodinated by contact with sodium or potassium iodide and a chemical oxidizing agent such as sodium hypochlorite, or an enzymatic oxidizing agent, such as lactoperoxidase. Proteins or peptides may be labeled with technetium-$^{99m}$ by ligand exchange process, for example, by reducing pertechnate with stannous solution, chelating the reduced technetium onto a Sephadex column and applying the peptide to this column or by direct labeling techniques, e.g., by incubating pertechnate, a reducing agent such as SNCl$_2$, a buffer solution such as sodium-potassium phthalate solution, and the peptide. Intermediary functional groups which are often used to bind radioisotopes which exist as metallic ions to peptides include diethylenetriaminepentaacetic acid (DTPA), DOTA, NOTA, porphyrin chelators and ethylene diaminetetracetic acid (EDTA). Also contemplated for use are fluorescent labels, including rhodamine, fluorescein isothiocyanate and renographin.

In certain embodiments, the proteins or peptides may be linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference. These fluorescent labels are preferred for in vitro uses, but may also be of utility in in vivo applications, particularly endoscopic or intravascular detection procedures.

In alternative embodiments, ligands, antibodies, or other proteins or peptides may be tagged with a fluorescent marker. Non-limiting examples of photodetectable labels include Alexa 350, Alexa 430, AMCA, aminoacridine, BODIPY 630/650, BODIPY 650/665, BODIPY-FL, BODIPY-R6G, BODIPY-TMR, BODIPY-TRX, 5-carboxy-4',5'-dichloro-2',7'-dimethoxy fluorescein, 5-carboxy-2',4',5',7'-tetrachlorofluorescein, 5-carboxyfluorescein, 5-carboxyrhodamine, 6-carboxyrhodamine, 6-carboxytetramethyl amino, Cascade Blue, Cy2, Cy3, Cy5,6-FAM, dansyl chloride, Fluorescein, HEX, 6-JOE, NBD (7-nitrobenz-2-oxa-1,3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, La Jolla blue dye, allopycocyanin, allococyanin B, phycocyanin C, phycocyanin R, thiamine, phycoerythrocyanin, phycoerythrin R, REG, Rhodamine Green, rhodamine isothiocyanate, Rhodamine Red, ROX, TAMRA, TET, TRIT (tetramethyl rhodamine isothiol), Tetramethylrhodamine, Edans and Texas Red. These and other luminescent labels may be obtained from commercial sources such as Molecular Probes (Eugene, Oreg.), and EMD Biosciences (San Diego, Calif.).

Chemiluminescent labeling compounds of use may include luminol, isoluminol, an aromatic acridinium ester, an imidazole, an acridinium salt and an oxalate ester, or a bioluminescent compound such as luciferin, luciferase and aequorin. Diagnostic conjugates may be used, for example, in intraoperative, endoscopic, or intravascular tumor or disease diagnosis.

In various embodiments, labels of use may comprise metal nanoparticles. Methods of preparing nanoparticles are known. (See e.g., U.S. Pat. Nos. 6,054,495; 6,127,120; 6,149,868; Lee and Meisel, J. Phys. Chem. 86:3391-3395, 1982.) Nanoparticles may also be obtained from commercial sources (e.g., Nanoprobes Inc., Yaphank, N.Y.; Polysciences, Inc., Warrington, Pa.). Modified nanoparticles are available commercially, such as Nanogold® nanoparticles from Nanoprobes, Inc. (Yaphank, N.Y.). Functionalized nanoparticles of use for conjugation to proteins or peptides may be commercially obtained.

Therapeutic Agents

Pharmaceutical Compositions

In some embodiments, a stably tethered structure and/or one or more other therapeutic agents may be administered to a subject, such as a subject with cancer. Such agents may be administered in the form of pharmaceutical compositions. Generally, this will entail preparing compositions that are essentially free of impurities that could be harmful to humans or animals. One skilled in the art would know that a pharmaceutical composition can be administered to a subject by various routes including, for example, orally or parenterally, such as intravenously.

In certain embodiments, an effective amount of a therapeutic agent must be administered to the subject. An "effective amount" is the amount of the agent that produces a desired effect. An effective amount will depend, for example, on the efficacy of the agent and on the intended effect. For example, a lesser amount of an antiangiogenic agent may be required for treatment of a hyperplastic condition, such as macular degeneration or endometriosis, compared to the amount required for cancer therapy in order to reduce or eliminate a solid tumor, or to prevent or reduce its metastasizing. An effective amount of a particular agent for a specific purpose can be determined using methods well known to those in the art.

Chemotherapeutic Agents

In certain embodiments, chemotherapeutic agents may be administered. Anti-cancer chemotherapeutic agents of use include, but are not limited to, 5-fluorouracil, bleomycin, busulfan, camptothecins, carboplatin, chlorambucil, cisplatin (CDDP), cyclophosphamide, dactinomycin, daunorubicin, doxorubicin, estrogen receptor binding agents, etoposide (VP16), farnesyl-protein transferase inhibitors, gemcitabine, ifosfamide, mechlorethamine, melphalan, methotrexate, mitomycin, navelbine, nitrosurea, plicamycin, procarbazine, raloxifene, tamoxifen, TAXOL®, temazolomide (an aqueous form of DTIC), transplatinum, vinblastine and methotrexate, vincristine, or any analog or derivative variant of the foregoing. Chemotherapeutic agents of use against infectious organisms include, but are not limited to, acyclovir, albendazole, amantadine, amikacin, amoxicillin, amphotericin B, ampicillin, aztreonam, azithromycin, bacitracin, BACTRIM®, Batrafen®, bifonazole, carbenicillin, caspofungin, cefaclor, cefazolin, cephalosporins, cefepime,ceftriaxone, cefotaxime, chloramphenicol, cidofovir, Cipro®, clarithromycin, clavulanic acid, clotrimazole, cloxacillin, doxycycline, econazole, erythrocycline, erythromycin, FLAGYL®, fluconazole, flucytosine, FOSCARNET®, furazolidone, ganciclovir, gentamycin, imipenem, isoniazid, itraconazole, kanamycin, ketoconazole, lincomycin, linezolid, meropenem, miconazole, minocycline, naftifine, nalidixic acid, neomycin, netilmicin, nitrofurantoin, nystatin, oseltamivir, oxacillin, paromomycin, penicillin, pentamidine, piperacillin-tazobactam, rifabutin, rifampin, rimantadine, streptomycin, sulfamethoxazole, sulfasalazine, tetracycline, tioconazole, tobramycin, tolciclate, tolnaftate, trimethoprim sulfamethoxazole, valacyclovir, vancomycin, zanamir, and zithromycin.

Chemotherapeutic agents and methods of administration, dosages, etc., are well known to those of skill in the art (see for example, the "Physicians Desk Reference", Goodman & Gilman's "The Pharmacological Basis of Therapeutics" and in "Remington's Pharmaceutical Sciences", incorporated herein by reference in relevant parts). Some variation in dosage will necessarily occur depending on the condition of the subject being treated. The person responsible for administration will, in any event, determine the appropriate dose for the individual subject.

Hormones

Corticosteroid hormones can increase the effectiveness of other chemotherapy agents, and consequently, they are frequently used in combination treatments. Prednisone and dexamethasone are examples of corticosteroid hormones. Progestins, such as hydroxyprogesterone caproate, medroxyprogesterone acetate, and megestrol acetate, have been used in cancers of the endometrium and breast. Estrogens such as diethylstilbestrol and ethinyl estradiol have been used in cancers such as prostate cancer. Antiestrogens such as tamoxifen have been used in cancers such as breast cancer. Androgens such as testosterone propionate and fluoxymesterone have also been used in treating breast cancer.

Angiogenesis Inhibitors

In certain embodiments, anti-angiogenic agents, such as angiostatin, baculostatin, canstatin, maspin, anti-VEGF antibodies, anti-PIGF peptides and antibodies, anti-vascular growth factor antibodies, anti-Flk-1 antibodies, anti-Flt-1 antibodies and peptides, laminin peptides, fibronectin peptides, plasminogen activator inhibitors, tissue metalloproteinase inhibitors, interferons, interleukin-12, IP-10, Gro-β, thrombospondin, 2-methoxyoestradiol, proliferin-related protein, carboxiamidotriazole, CM101, Marimastat, pentosan polysulphate, angiopoietin-2, interferon-alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline may be of use.

Immunomodulators

As used herein, the term "immunomodulator" includes cytokines, stem cell growth factors, lymphotoxins and hematopoietic factors, such as interleukins, colony-stimulating factors, interferons (e.g., interferons-α, -β and -γ) and the stem cell growth factor designated "S1 factor." Examples of suitable immunomodulator moieties include IL-2, IL-6, IL-10, IL-12, IL-18, IL-21, interferon-gamma, TNF-alpha, and the like.

The term "cytokine" is a generic term for proteins or peptides released by one cell population which act on another cell as intercellular mediators. As used broadly herein, examples of cytokines include lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, Il-15, IL-16, IL-17, IL-18, IL-21, LIF, G-CSF, GM-CSF, M-CSF, EPO, kit-ligand or FLT-3, angiostatin, thrombospondin, endostatin, tumor necrosis factor and LT. As used herein, the term cytokine includes proteins from natural sources or from recombinant cell culture and biologically active equivalents of the native sequence cytokines.

Chemokines generally act as chemoattractants to recruit immune effector cells to the site of chemokine expression. Chemokines include, but are not limited to, RANTES, MCAF, MIP1-alpha, MIP1-Beta, and IP-10. The skilled artisan will recognize that certain cytokines are also known to have chemoattractant effects and could also be classified under the term chemokines. Similarly, the terms immunomodulator and cytokine overlap in their respective members.

Radioisotope Therapy and Radioimmunotherapy

In some embodiments, the peptides and/or proteins may be of use in radionuclide therapy or radioimmunotherapy methods (see, e.g., Govindan et al., 2005, *Technology in Cancer Research & Treatment*, 4:375-91; Sharkey and Goldenberg, 2005, *J. Nucl. Med.* 46:115S-127S; Goldenberg et al. (J Clin Oncol 2006; 24:823-834), "Antibody Pre-targeting Advances Cancer Radioimmunodetection and Radioimmunotherapy," each incorporated herein by reference.) In specific embodiments, stably tethered structures may be directly tagged with a radioisotope of use and administered to a subject. In alternative embodiments, radioisotope(s) may be administered in a pre-targeting method as discussed above, using a haptenic peptide or ligand that is radiolabeled and injected after administration of a bispecific stably tethered structure that localizes at the site of elevated expression in the diseased tissue.

Radioactive isotopes useful for treating diseased tissue include, but are not limited to-$^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, 1-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV.

For example, $^{67}Cu$, considered one of the more promising radioisotopes for radioimmunotherapy due to its 61.5 hour half-life and abundant supply of beta particles and gamma rays, can be conjugated to a protein or peptide using the chelating agent, p-bromoacetamido-benzyl-tetraethylamine-tetraacetic acid (TETA). Alternatively, $^{90}Y$, which emits an energetic beta particle, can be coupled to a peptide, antibody, fusion protein, or fragment thereof, using diethylenetriamine-pentaacetic acid (DTPA).

Additional potential radioisotopes include $^{11}C$, $^{13}N$, $^{15}O$, $^{75}Br$, $^{198}Au$, $^{224}Ac$, $^{126}I$, $^{133}I$, $^{77}Br$, $^{113m}In$, $^{95}Ru$, $^{97}Ru$, $^{103}Ru$, $^{105}Ru$, $^{107}Hg$, $^{203}Hg$, $^{121m}Te$, $^{122m}Te$, $^{125m}Te$, $^{165}Tm$, $^{167}Tm$, $^{168}Tm$, $^{197}Pt$, $^{109}Pd$, $^{105}Rh$, $^{142}Pr$, $^{143}Pr$, $^{161}Tb$, $^{166}Ho$, $^{199}Au$, $^{57}Co$, $^{58}Co$, $^{51}Cr$, $^{59}Fe$, $^{75}Se$, $^{201}Tl$, $^{225}Ac$, $^{76}Br$, $^{169}Yb$, and the like.

In another embodiment, a radiosensitizer can be used. The addition of the radiosensitizer can result in enhanced efficacy. Radiosensitizers are described in D. M. Goldenberg (ed.), CANCER THERAPY WITH RADIOLABELED ANTIBODIES, CRC Press (1995), which is incorporated herein by reference in its entirety.

The peptide, antibody, antibody fragment, or fusion protein that has a boron addend-loaded carrier for thermal neutron activation therapy will normally be effected in similar ways. However, it will be advantageous to wait until non-targeted immunoconjugate clears before neutron irradiation is performed. Clearance can be accelerated using an antibody that binds to the ligand. See U.S. Pat. No. 4,624,846 for a description of this general principle. For example, boron addends such as carboranes, can be attached to antibodies. Carboranes can be prepared with carboxyl functions on pendant side chains, as is well-known in the art. Attachment of carboranes to a carrier, such as aminodextran, can be achieved by activation of the carboxyl groups of the carboranes and condensation with amines on the carrier. The intermediate conjugate is then conjugated to the antibody. After administration of the conjugate, a boron addend is activated by thermal neutron irradiation and converted to radioactive atoms which decay by alpha-emission to produce highly toxic, short-range effects.

Kits

Various embodiments may concern kits containing components suitable for treating or diagnosing diseased tissue in a patient. Exemplary kits may contain at least one stably tethered structure. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used.

The kit components may be packaged together or separated into two or more separate containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

The following examples are provided to illustrate, but not to limit the claimed invention.

Example 1

General Strategy for Producing Fab-Based Subunits with the DDD1 Sequence Appended to Either the C- or N-Terminus of the Fd Chain Fab-based subunits with the DDD1 sequence (SEQ ID NO:1) appended to either the C- or N-terminus of the Fd chain are produced as fusion proteins. The plasmid vector pdHL2 has been used to produce a number of antibodies and antibody-based constructs. See Gillies et al., J Immunol Methods (1989), 125:191-202; Losman et al., Cancer (Phila) (1997), 80:2660-6. The di-cistronic mammalian expression vector directs the synthesis of the heavy and light chains of IgG. The vector sequences are mostly identical for many different IgG-pdHL2 constructs, with the only differences existing in the variable domain (VH and VL) sequences. Using molecular biology tools known to those skilled in the art, these IgG-pdHL2 expression vectors can be converted into Fd-DDD1-pdHL2 or Fd-DDD2-pdHL2 expression vectors by replacing the coding sequences for the hinge, CH2 and CH3 domains of the heavy chain with a sequence encoding the first 4 residues of the hinge, a 14 residue Gly-Ser linker and the first 44 residues of human RIIα. The shuttle vector CH1-DDD1-pGemT was designed to facilitate the conversion of IgG-pdHL2 vectors (FIG. 2a) to Fd-DDD1-pdHL2 vectors (FIG. 2b), as described below.

Generation of the Shuttle Vector CH1-DDD1-pGemT

Preparation of CH1

The CH1 domain was amplified by PCR using the pdHL2 plasmid vector as a template. The left PCR primer consists of the upstream (5') of the CH1 domain and a SacII restriction endonuclease site, which is 5' of the CH1 coding sequence. The right primer consists of the sequence coding for the first 4 residues of the hinge (PKSC) followed by GGGGS with the final two codons (GS) comprising a Bam HI restriction site.

```
5' of CH1 Left Primer
                                          (SEQ ID NO: 4)
5'GAACCTCGCGGACAGTTAAG-3'

CH1 + G4S-Bam Right
                                          (SEQ ID NO: 5)
5'GGATCCTCCGCCGCCGCAGCTCTTAGGTTTCTTGTCCACCTTG
GTGTTGCTGG-3'
```

The 410 bp PCR amplimer was cloned into the pGemT PCR cloning vector (Promega, Inc.) and clones were screened for inserts in the T7 (5') orientation.

Construction of (G₄S)₂DDD1

A duplex oligonucleotide, designated (G₄S)₂DDD1, was synthesized by Sigma Genosys (Haverhill, UK) to code for the amino acid sequence of DDD1 (SEQ ID NO:1) preceded by 11 residues of the linker peptide, with the first two codons comprising a BamHI restriction site. A stop codon and an EagI restriction site are appended to the 3'end. The encoded polypeptide sequence is shown below.

(SEQ ID NO: 6)
GSGGGGSGGGGSHIQIPPGLTELLQGYTVEVLRQQPPDLVEFAVEYFT

RLREARA

The two oligonucleotides, designated RIIA1-44 top and RIIA1-44 bottom, which overlap by 30 base pairs on their 3' ends, were synthesized (Sigma Genosys) and combined to comprise the central 154 base pairs of the 174 bp DDD1 sequence. The oligonucleotides were annealed and subjected to a primer extension reaction with Taq polymerase.

```
RIIA1-44 top
                                       (SEQ ID NO: 7)
5'GTGGCGGGTCTGGCGGAGGTGGCAGCCACATCCAGATCC

CGCCGGGGCTCACGGAGCTGCTGCAGGGCTACACGGTGGAG

GTGCTGCGACAG-3'

RIIA1-44 bottom
                                       (SEQ ID NO: 8)
5'GCGCGAGCTTCTCTCAGGCGGGTGAAGTACTCCACTGCGAA

TTCGACGAGGTCAGGCGGCTGCTGTCGCAGCACCTCCACCGTGT

AGCCCTG-3'
```

Following primer extension, the duplex was amplified by PCR using the following primers:

```
G4S Bam-Left
                                       (SEQ ID NO: 9)
5'-GGATCCGGAGGTGGCGGGTCTGGCGGAGGT-3'

1-44 stop Eag Right
                                       (SEQ ID NO: 10)
5'-CGGCCGTCAAGCGCGAGCTTCTCTCAGGCG-3'
```

This amplimer was cloned into pGemT and screened for inserts in the T7 (5') orientation.

Ligating DDD1 with CH1

A 190 bp fragment encoding the DDD1 sequence was excised from pGemT with BamHI and NotI restriction enzymes and then ligated into the same sites in CH1-pGemT to generate the shuttle vector CH1-DDD1-pGemT.

Cloning CH1-DDD1 into pdHL2-Based Vectors

The sequence encoding CH1-DDD1 can be incorporated into any IgG construct in the pdHL2 vector as follows. The entire heavy chain constant domain is replaced with CH1-DDD1 by removing the SacII/EagI restriction fragment (CH1-CH3) from pdHL2 and replacing it with the SacII/EagI fragment of CH1-DDD1, which is excised from the respective pGemT shuttle vector.

It is noted that the location of DDD1 is not restricted to the carboxyl terminal end of CH1 and can be placed at the amino terminal end of the VH domain, as shown in Example 2.

Example 2

Methods for Generating a₂ Constructs Composed of Two Identical Fab Subunits Stably Linked Via the DDD1 Sequence Fused to Either the C- or N-Terminus of the Fd Chain Construction of C-DDD1-Fd-hMN-14-pdHL2

Figure 3:
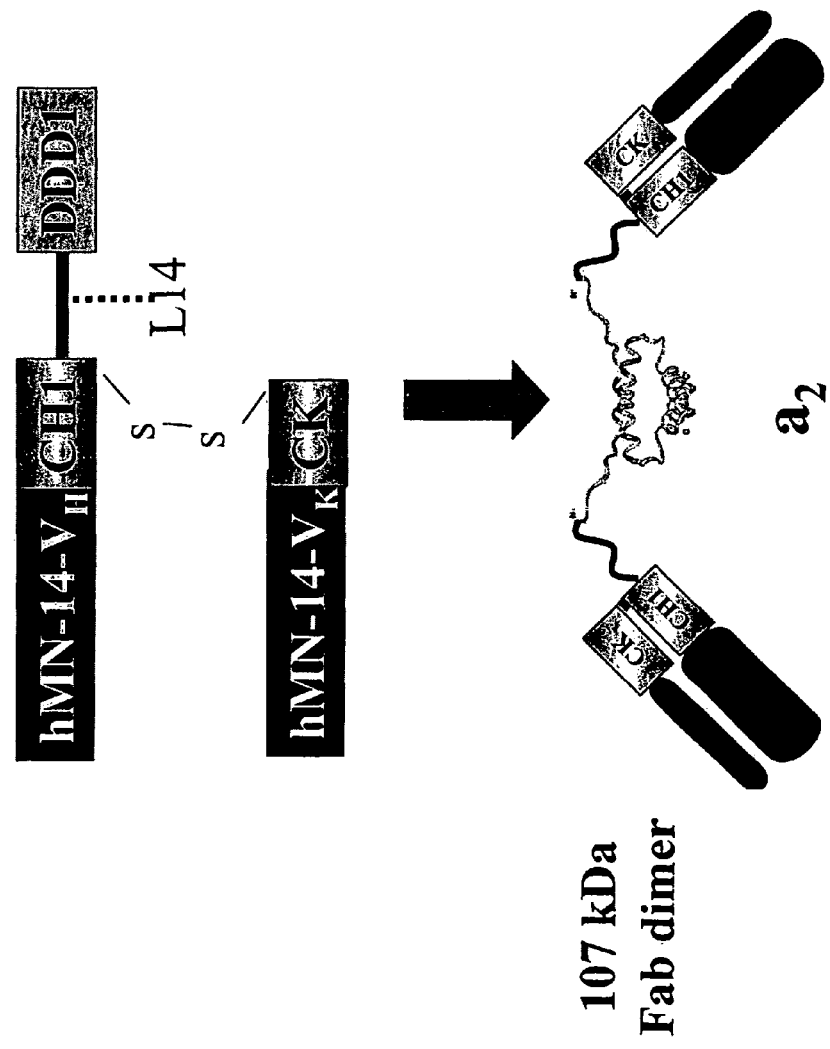
FIG. 3 shows a schematic diagram of C-DDD1-Fab-hMN-14 and the putative $a_2$ structure formed by DDD1 mediated dimerization.

C-DDD1-Fd-hMN-14-pdHL2 is an expression vector for producing an a₂ construct that comprises two copies of a fusion protein in which the DDD1 sequence is linked to hMN-14 Fab at the C-terminus of the Fd chain via a flexible peptide spacer (FIG. 3). The plasmid vector hMN14(I)-pdHL2, which has been used to produce hMN-14 IgG, was converted to C-DDD1-Fd-hMN-14-pdHL2 by digestion with SacII and EagI restriction endonucleases, to remove the fragment encoding the CH1-CH3 domains, and insertion of the CH1-DDD1 fragment, which was excised from the CH1-DDD1-SV3 shuttle vector with SacII and EagI.

Construction of N-DDD1-Fd-hMN-14-pdHL2

Figure 4:
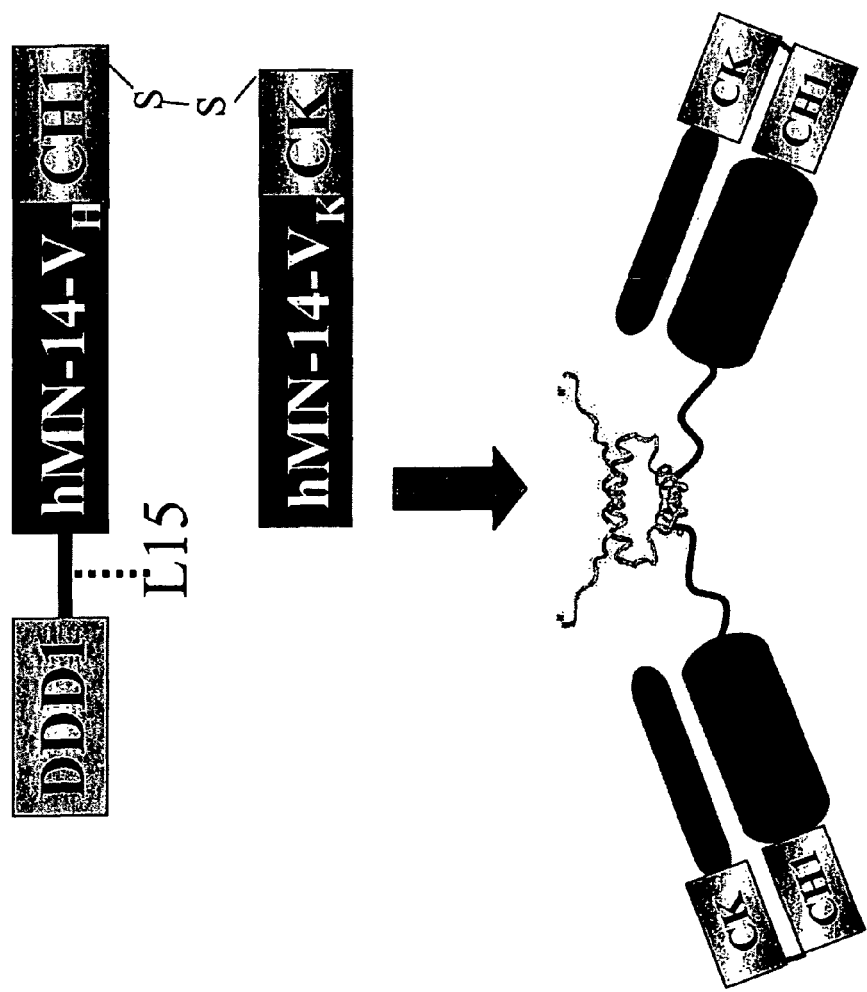
FIG. 4 shows a schematic diagram of N-DDD1-Fab-hMN-14 and the putative $a_2$ structure formed by DDD1 mediated dimerization.

N-DDD1-Fd-hMN-14-pdHL2 is an expression vector for producing an a₂ construct that comprises two copies of a fusion protein in which the DDD1 sequence is linked to hMN-14 Fab at the N-terminus of the Fd chain via a flexible peptide spacer (FIG. 4).

The expression vector was engineered as follows. The DDD1 domain was amplified by PCR using the two primers shown below.

```
DDD1 Nco Left
                                       (SEQ ID NO: 11)
5' CCATGGGCAGCCACATCCAGATCCCGCC-3'

DDD1-G4S Bam Right
                                       (SEQ ID NO: 12)
5'GGATCCGCCACCTCCAGATCCTCCGCCGCCAGCGCGAGCTTCTCTCAG

GCGGGTG-3'
```

As a result of the PCR, an NcoI restriction site and the coding sequence for part of the linker (G₄S)₂ containing a BamHI restriction were appended to the 5' and 3' ends, respectively. The 170 bp PCR amplimer was cloned into the pGemT vector and clones were screened for inserts in the T7 (5') orientation. The 194 bp insert was excised from the pGemT vector with NcoI and SalI restriction enzymes and cloned into the SV3 shuttle vector, which was prepared by digestion with those same enzymes, to generate the intermediate vector DDD1-SV3.

The hMN-14 Fd sequence was amplified by PCR using the oligonucleotide primers shown below.

```
hMN-14VH left G4S Bam
                                       (SEQ ID NO: 13)
5'-GGATCCGGCGGAGGTGGCTCTGAGGTCCAACTGGTGGAGAGCGG-3'

CH1-C stop Eag
                                       (SEQ ID NO: 14)
5'-CGGCCGTCAGCAGCTCTTAGGTTTCTTGTC-3'
```

As a result of the PCR, a BamHI restriction site and the coding sequence for part of the linker (G₄S) were appended to the 5' end of the amplimer. A stop codon and EagI restriction site was appended to the 3'end. The 1043 bp amplimer was cloned into pGemT. The hMN-14-Fd insert was excised from pGemT with BamHI and EagI restriction enzymes and then ligated with DDD1-SV3 vector, which was prepared by digestion with those same enzymes, to generate the construct N-DDD1-Fd-hMN-14-SV3.

The N-DDD1-hMN-14 Fd sequence was excised with XhoI and EagI restriction enzymes and the 1.28 kb insert fragment was ligated with a vector fragment that was prepared by digestion of C-DDD1-Fd-hMN-14-pdHL2 with those same enzymes. The final expression vector is N-DDD1-Fd-hMN-14-pDHL2.

Production, Purification and Characterization of N-DDD1-Fab-hMN-14 and C-DDD1-Fab-hMN-14

The C-DDD1-Fd-hMN-14-pdHL2 and N-DDD1-Fd-hMN-14-pdHL2 vectors were transfected into Sp2/0-derived myeloma cells by electroporation. C-DDD1-Fd-hMN-14-pdHL2 is a di-cistronic expression vector, which directs the synthesis and secretion of both hMN-14 kappa light chain and hMN-14 Fd-DDD1, which combine to form C-DDD1-hMN-14 Fab. N-DDD1-hMN-14-pdHL2 is a di-cistronic expression vector, which directs the synthesis and secretion of both hMN-14 kappa light chain and N-DDD1-Fd-hMN-14, which combine to form N-DDD1-Fab-hMN-14. Each fusion protein forms a stable homodimer via the interaction of the DDD1 domain.

Following electroporation, the cells were plated in 96-well tissue culture plates and transfectant clones were selected with 0.05 µM methotrexate (MTX). Clones were screened for protein expression by ELISA, using microtitre plates coated with WI2 (a rat anti-id monoclonal antibody to hMN-14) and detection with HRP-conjugated goat anti-human Fab. The initial productivity of the highest producing C-DDD1-Fab-hMN14 and N-DDD1-Fab-hMN14 clones was 60 mg/L and 6 mg/L, respectively.

Figure 6:
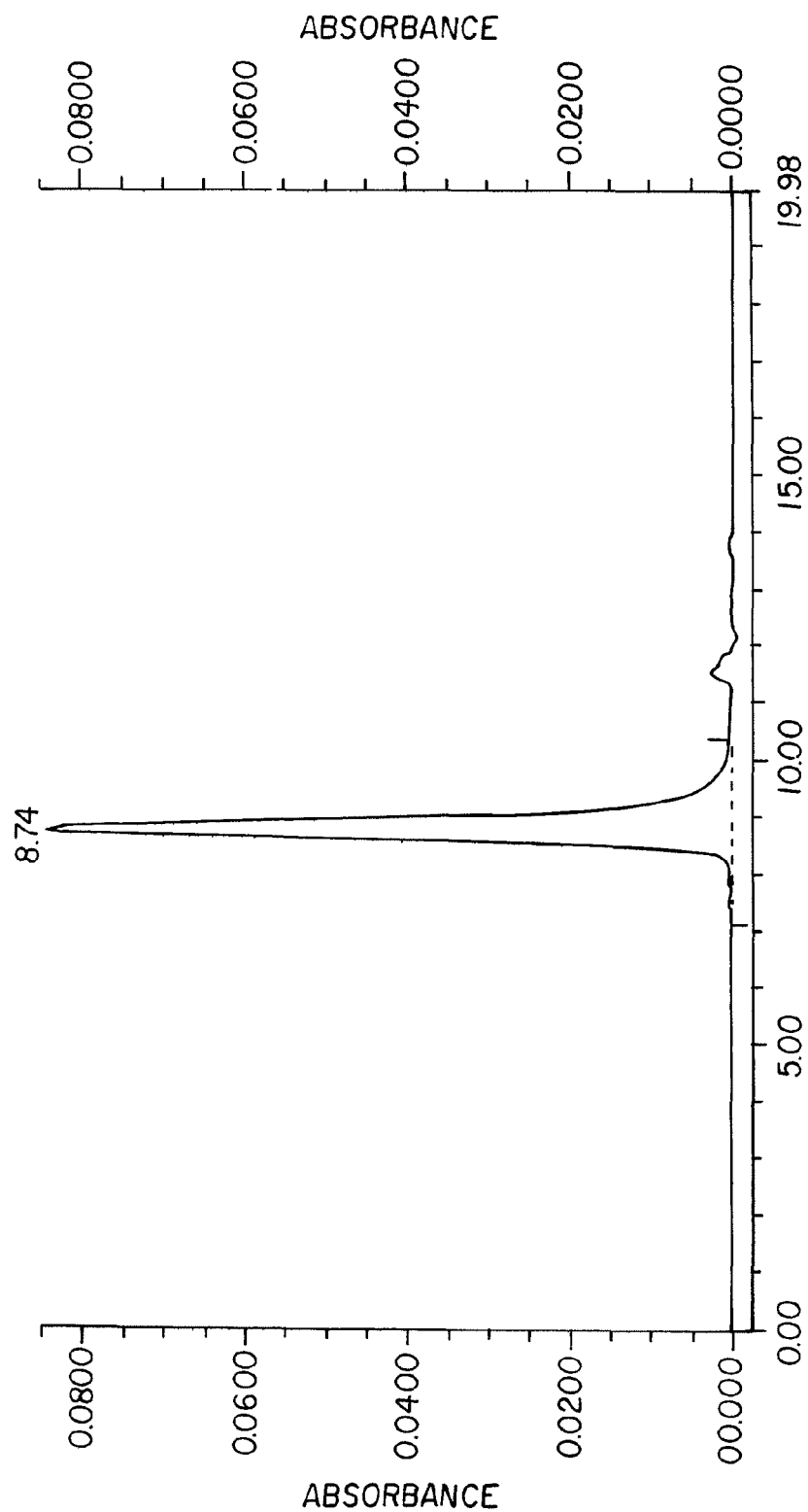
FIG. 6 shows SE-HPLC analysis of affinity-purified C-DDD1-Fab-hMN-14.
Figure 7:
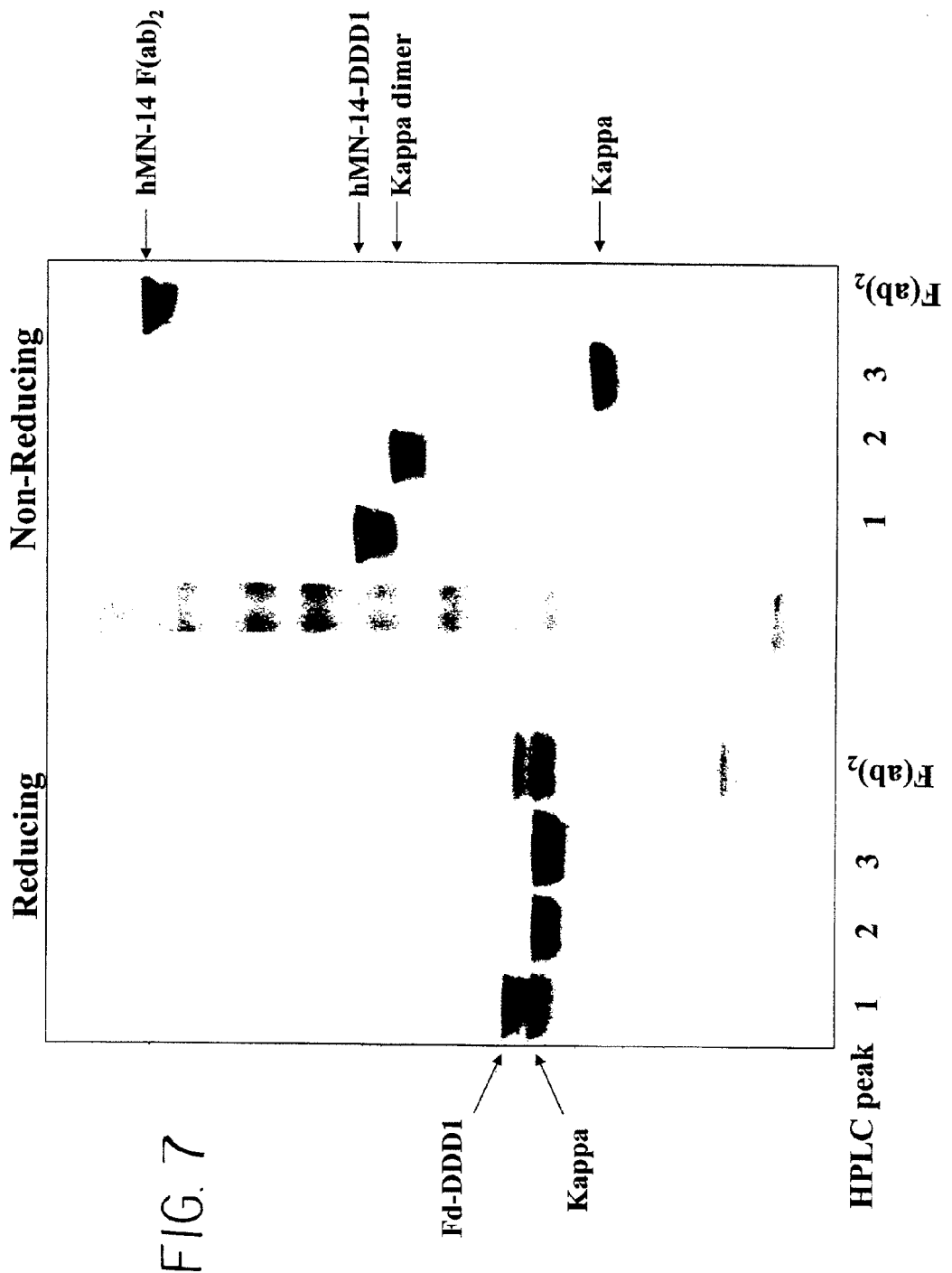
FIG. 7 shows SDS-PAGE analysis of affinity-purified C-DDD1-Fab-hMN-14.

Both fusion proteins are purified using affinity chromatography. AD1-C is a peptide that binds specifically to DDD1-containing $a_2$ constructs. The amino acid sequence of AD1-C (SEQ ID NO:3) is shown in FIG. 5. AD1-C was coupled to Affigel following reaction of the suithydryl group with chloroacetic anhydride. Culture supernatants were concentrated approximately 10-fold by ultrafiltration before loading onto an AD1-C-affigel column. The column was washed to baseline with PBS and C-DDD1-Fab-hMN-14 was eluted with 0.1 M Glycine, pH 2.5. The one-step affinity purification yielded about 81 mg of C-DDD1-Fab-hMN-14 from 1.2 liters of roller bottle culture. SE-HPLC analysis (FIG. 6) of the eluate shows a single protein peak with a retention time (8.7 min) consistent with a 107-kDa protein. The purity was also confirmed by reducing SDS-PAGE (FIG. 7), showing only two bands of molecular size expected for the two polypeptide constituents of C-DDD1-Fab-hMN-14.

Figure 8:
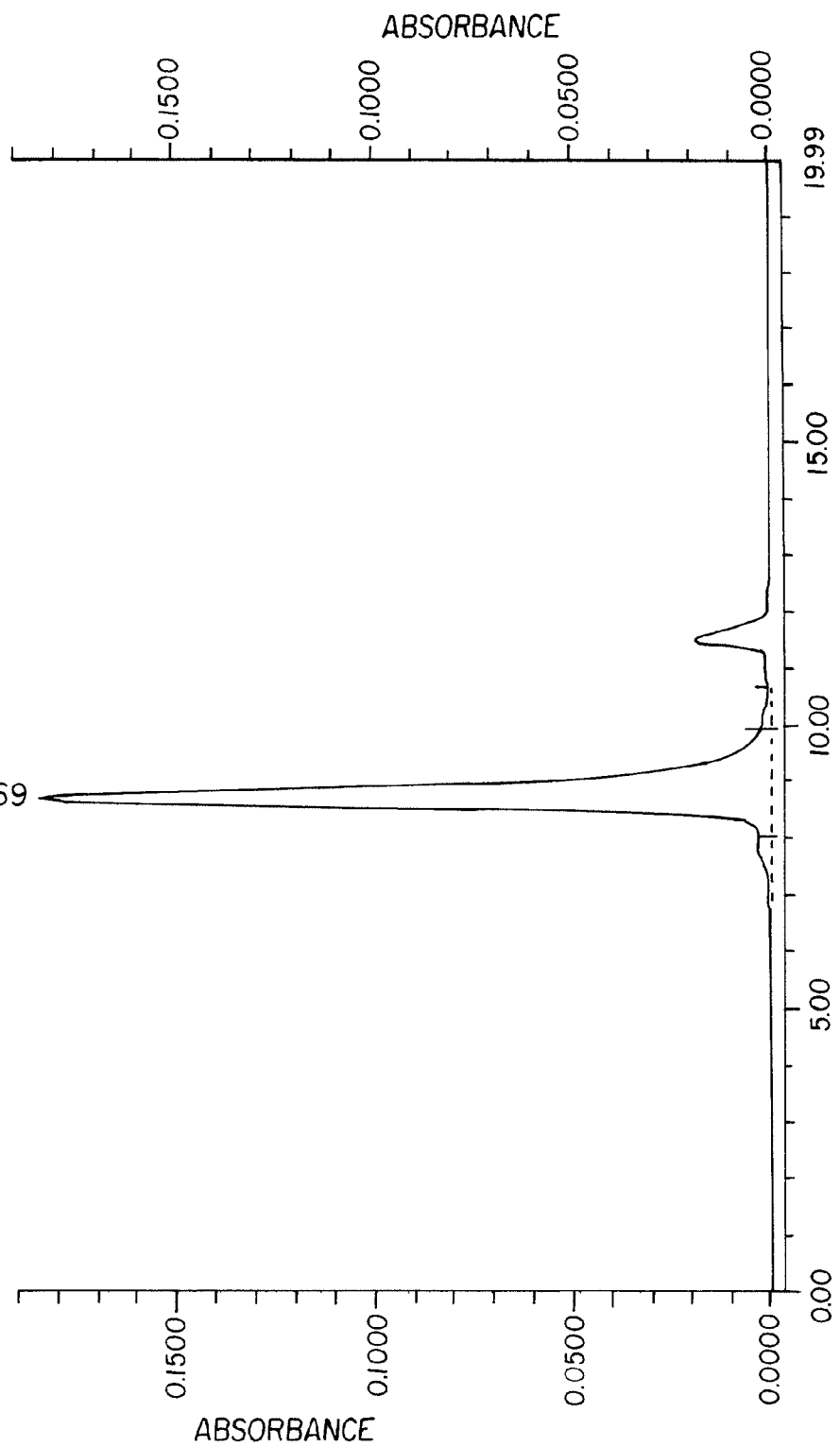
FIG. 8 shows SE-HPLC analysis of affinity-purified N-DDD1-Fab-hMN-14.

N-DDD1-Fab-hMN-14 was purified as described above for C-DDD1-Fab-hMN-14, yielding 10 mg from 1.2 liters of roller bottle culture. SE-HPLC analysis (FIG. 8) of the eluate shows a single protein peak with a retention time (8.77 min) similar to C-DDD1-Fab-hMN-14 and consistent with a 107 kDa protein. Reducing SDS-PAGE shows only two bands attributed to the polypeptide constituents of N-DDD1-Fab-hMN-14.

Figure 9:
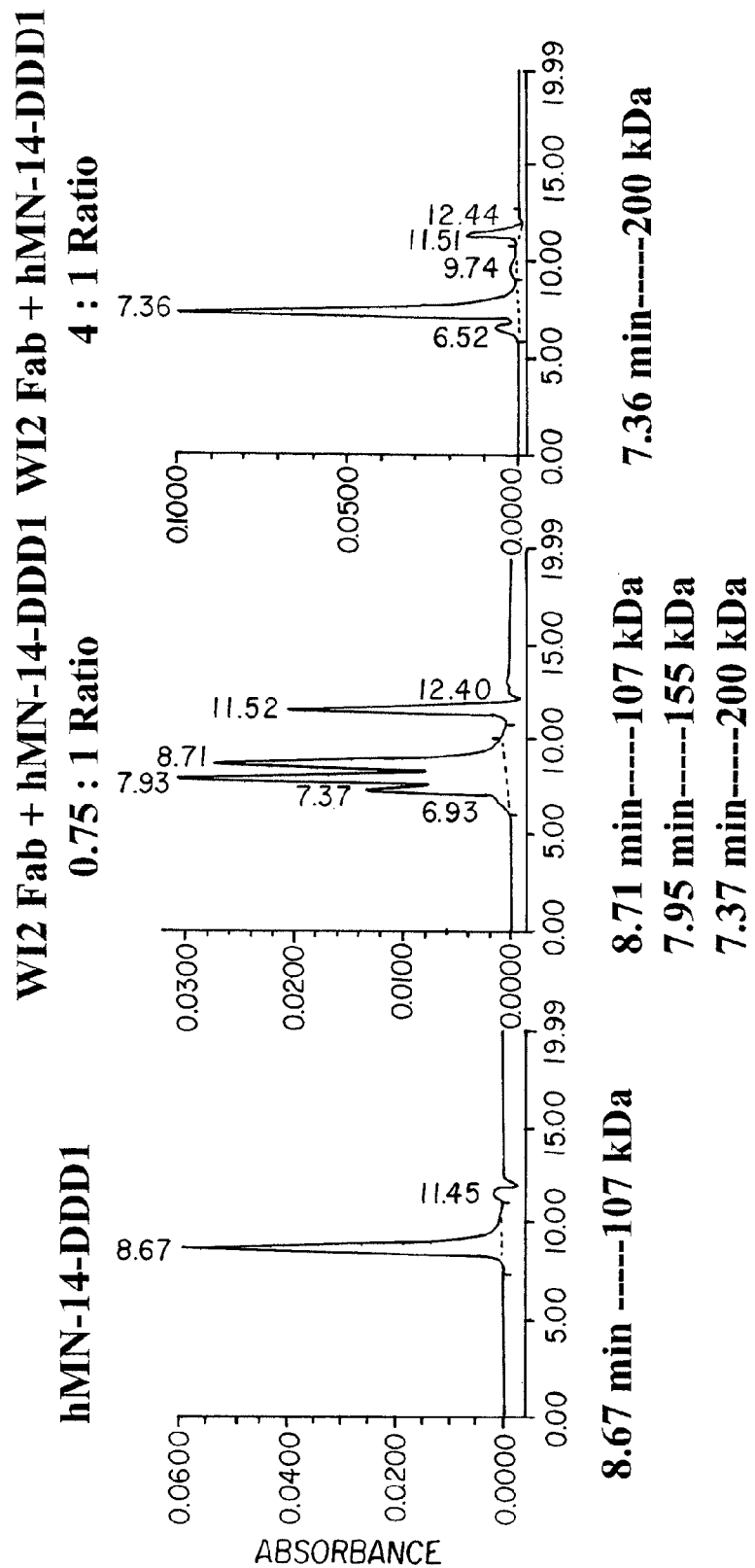
FIG. 9 shows C-DDD1-Fab-hMN-14 contains two active binding sites.
Figure 10:
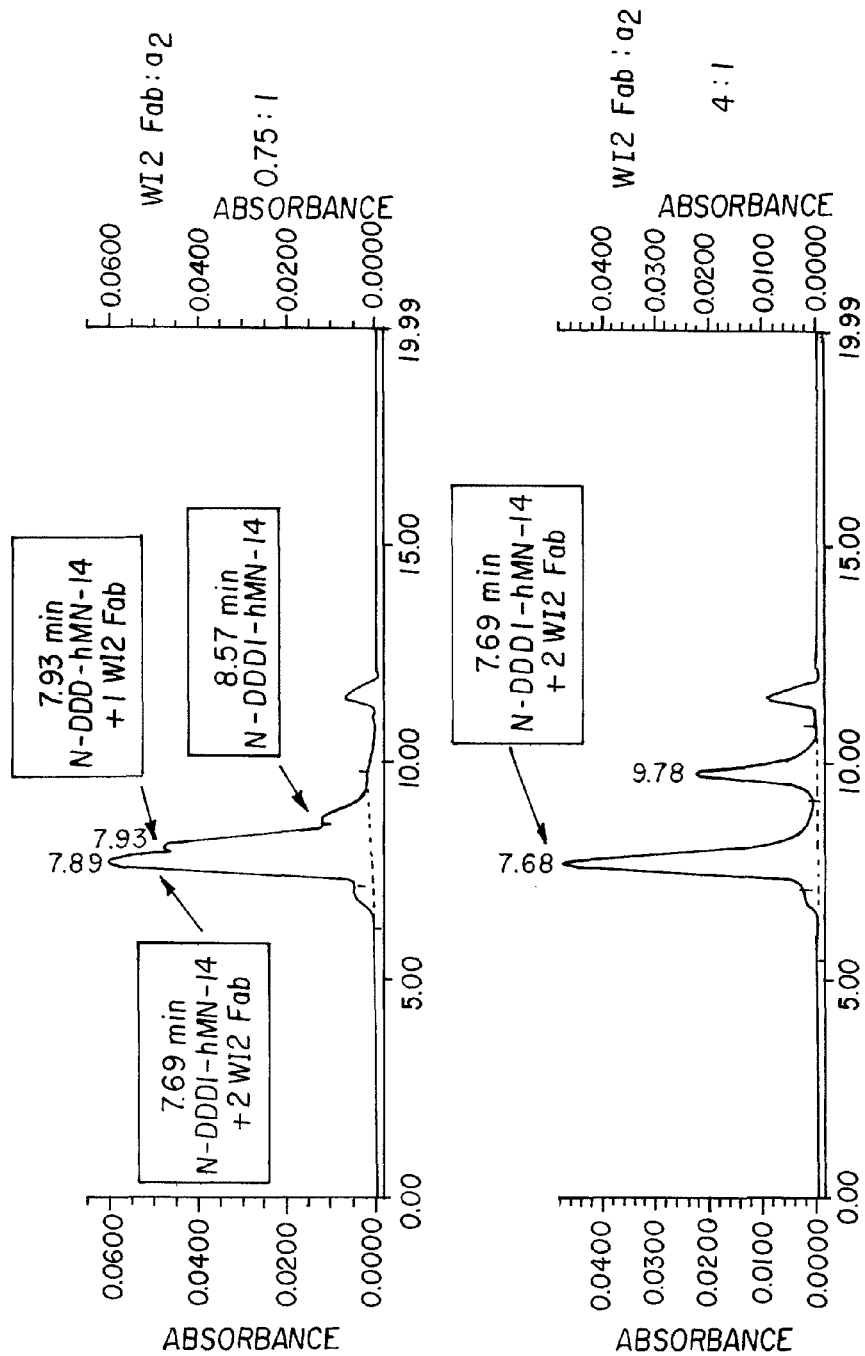
FIG. 10 shows N-DDD1-Fab-hMN-14 contains two active binding sites

The binding activity of C-DDD1-Fab-hMN-14 was determined by SE-HPLC analysis of samples in which the test article was mixed with various amounts of WI2. A sample prepared by mixing WI2 Fab and C-DDD1-Fab-hMN-14 at a molar ratio of 0.75:1 showed three peaks, which were attributed to unbound C-DDD1-Fab-hMN14 (8.71 min.), C-DDD1-Fab-hMN-14 bound to one WI2 Fab (7.95 min.), and C-DDD1-Fab-hMN14 bound to two WI2 Fabs (7.37 min.). When a sample containing WI2 Fab and C-DDD1-Fab-hMN-14 at a molar ratio of 4 was analyzed, only a single peak at 7.36 minutes was observed. These results (FIG. 9) demonstrate that C-DDD1-Fab-hMN-14 is dimeric and has two active binding sites. Very similar results (FIG. 10) were obtained when this experiment was repeated with N-DDD1-Fab-hMN-14.

Figure 11:
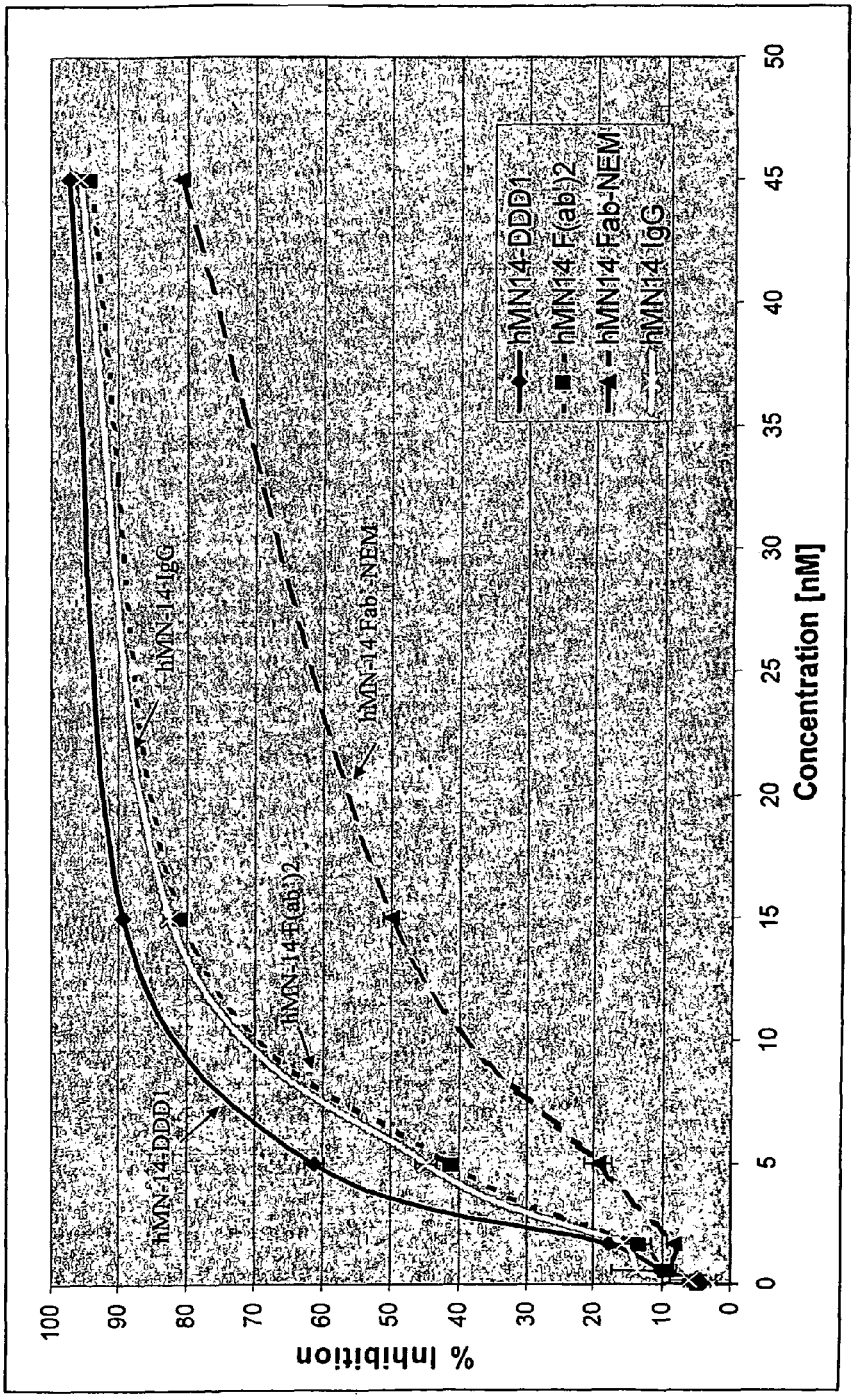
FIG. 11 shows the binding affinity of C-DDD1-Fab-hMN-14 is at least equivalent to the bivalent hMN-14 IgG or F(ab')2 and about 5-fold higher than the monovalent Fab.
Figure 12:
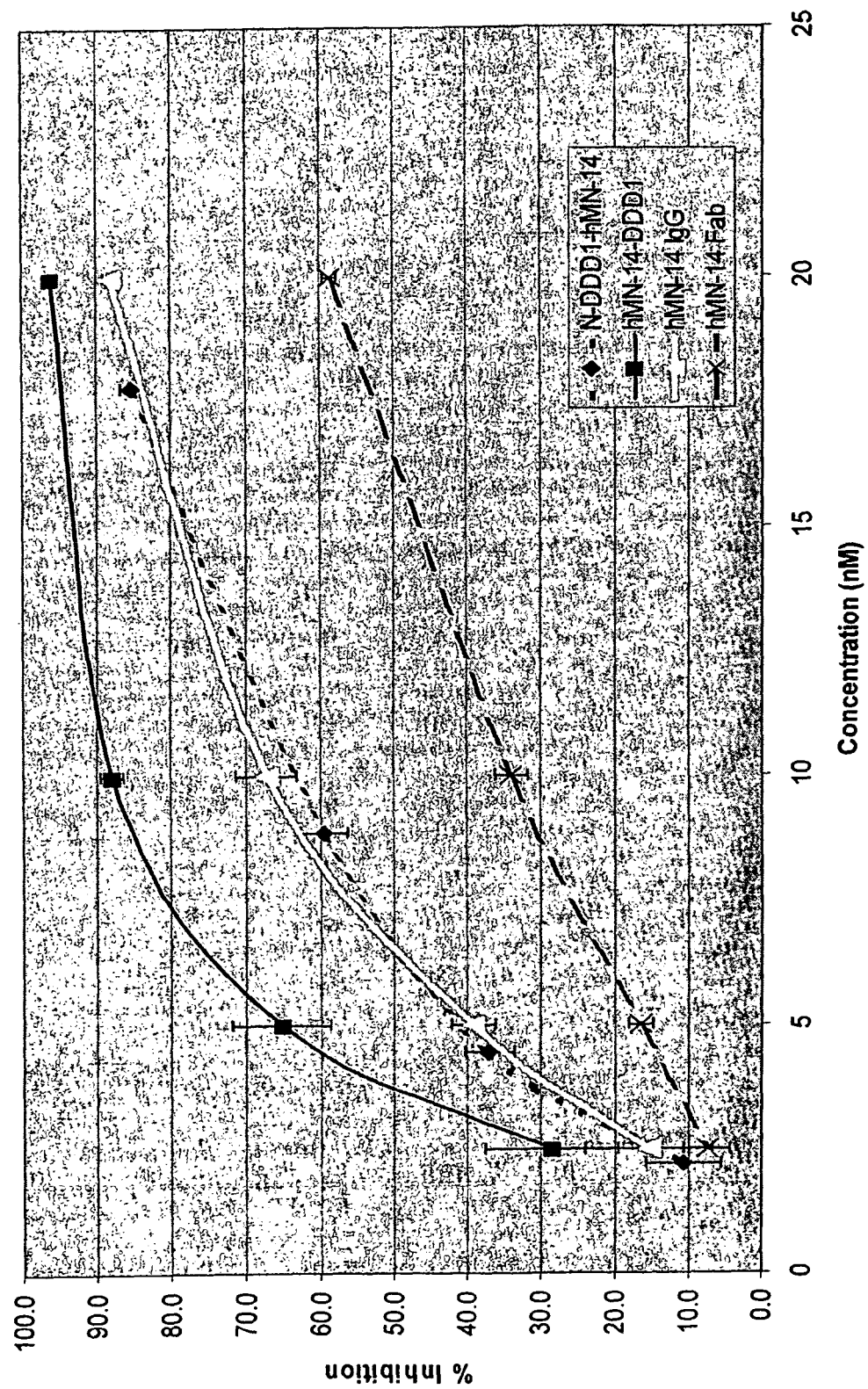
FIG. 12 shows the binding affinity of N-DDD1-Fab-hMN-14 is equivalent to bivalent hMN-14 IgG and the binding affinity of C-DDD1-Fab-hMN-14 is higher than hMN-14 IgG.
Figure 13:
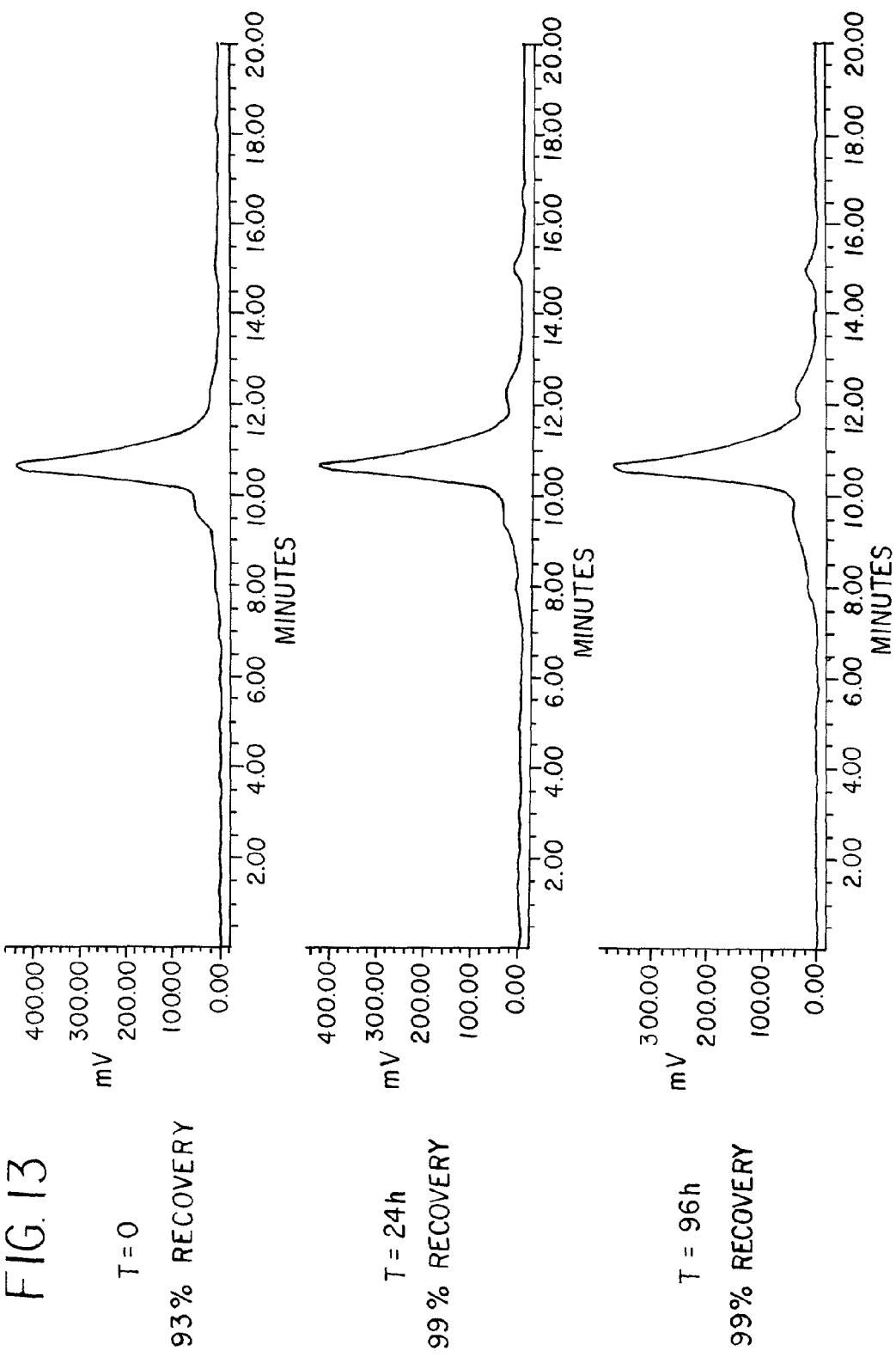
FIG. 13 shows C-DDD1-Fab-hMN-14 is stable in pooled human serum with no apparent change in molecular integrity over 96 h.
Figure 14:
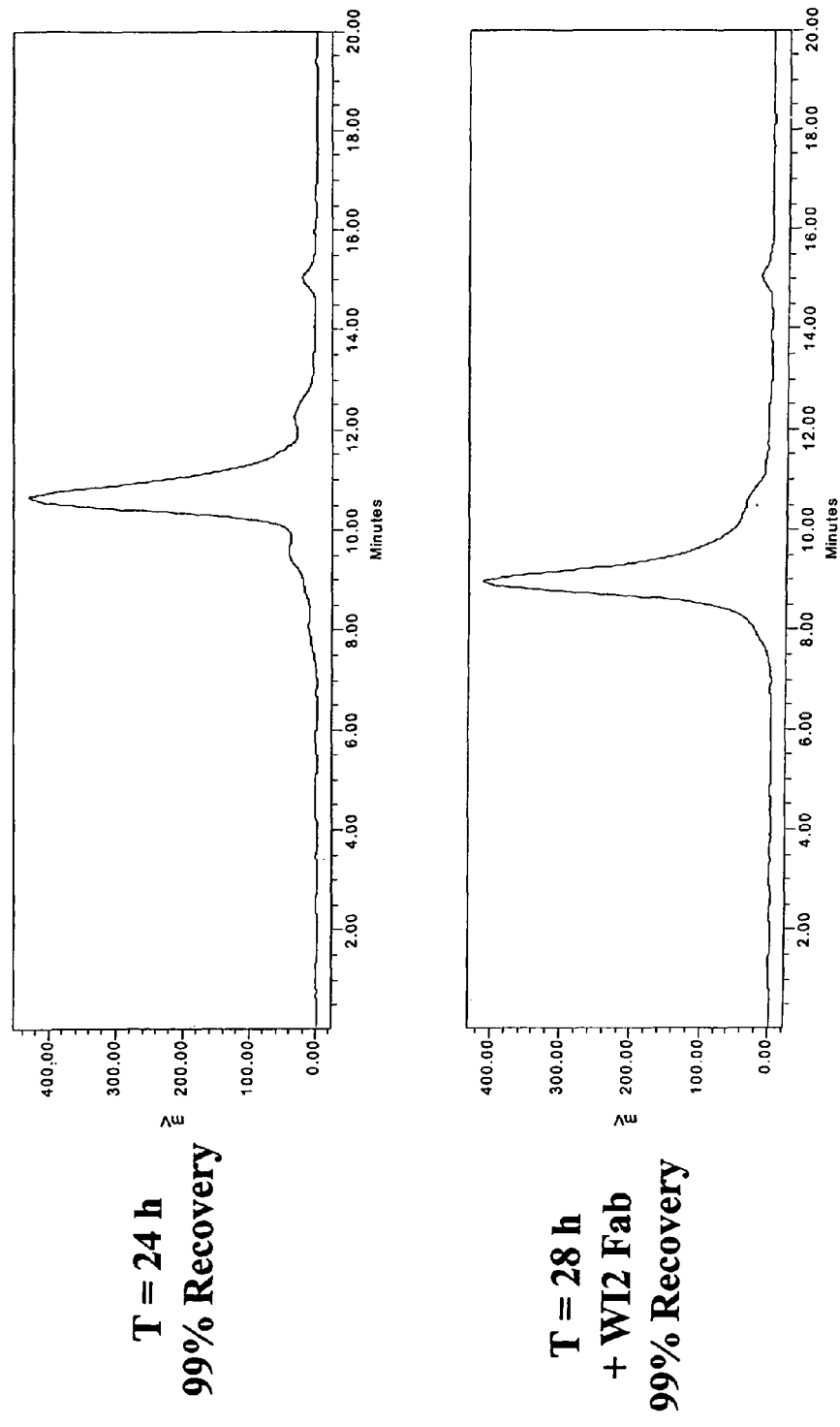
FIG. 14 shows C-DDD1-Fab-hMN-14 is stable in pooled human serum with unchanged immunoreactivity over 28 h.
Figure 15:
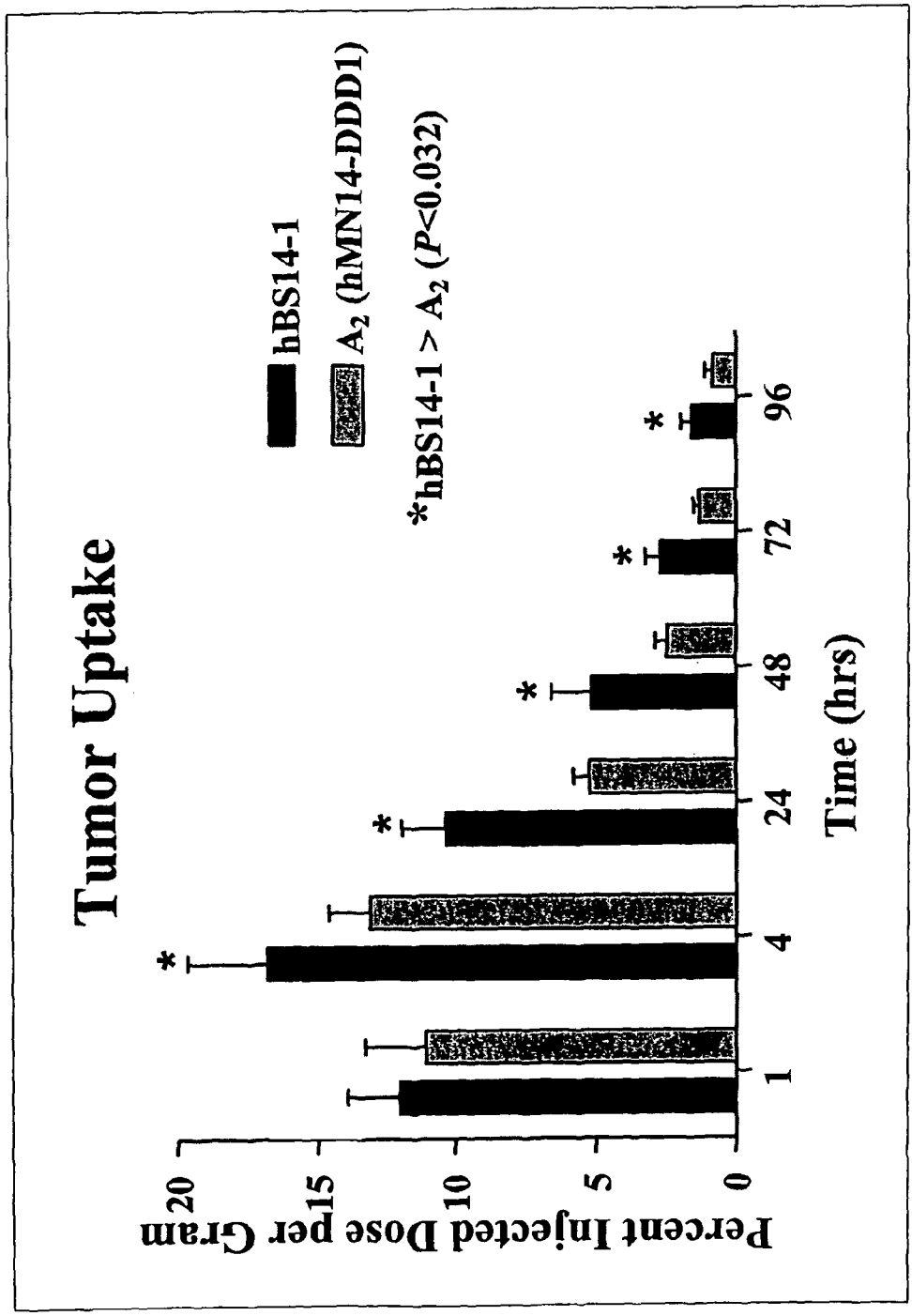
FIG. 15 compares the tumor uptake of C-DDD1-Fab-hMN-14 with that of hBS14-1 in mice bearing human colorectal cancer xenografts.
Figure 16:
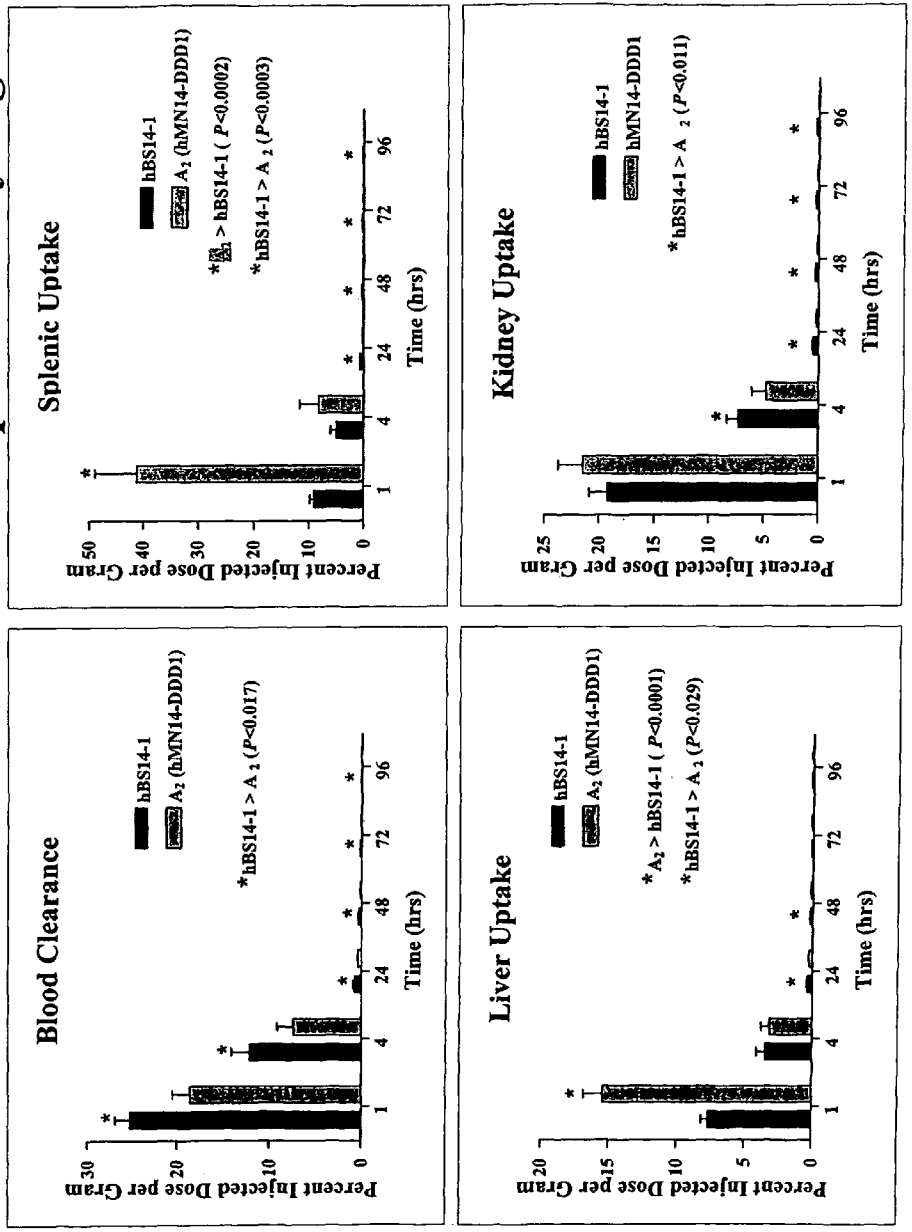
FIG. 16 compares the normal organ uptake of C-DDD1-Fab-hMN-14 with that of hBS14-1 in mice bearing human colorectal cancer xenografts

Competitive ELISA (FIGS. 11 and 12) demonstrated that C-DDD1-Fab-hMN-14 and N-DDD1-Fab-hMN-14 binds to CEA with similar avidity to hMN-14 IgG, and significantly stronger than monovalent hMN-14 Fab. ELISA plates were coated with a fusion protein containing the epitope (A3B3) of CEA to which hMN-14 binds specifically. C-DDD1-Fab-hMN-14 is stable in pooled human serum for at least 24 h without appreciable loss in immunoreactivity as shown in FIGS. 13 and 14. C-DDD1-Fab-hMN-14 has been evaluated in mice bearing human colorectal cancer xenografts (LS174T) and the results (FIGS. 15 and 16) were similar to those obtained for hBS14-1, which is also bivalent for binding to CEA.

Example 3

Methods for Generating $a_2$ Constructs Composed of Two Identical Fab Fusion Proteins, each Containing Ranpirnase (Rap) and the DDD1 Sequence Linked to the N-Terminus of the Light Chain and the C-terminus of the Fd Chain, Respectively Construction of Rap-hPAM4-Fd-DDD1-pdHL2

Rap-hPAM4-Fd-DDD1-pdHL2 is an expression vector for producing an $a_2$ construct that comprises two identical Fab fusion proteins, each containing ranpimase (Rap) and the DDD1 sequence linked to the N-terminus of the light chain and the C-terminus of the Fd chain, respectively. hPAM4 is a humanized monoclonal antibody specific for MUC-1. The plasmid vector Rap-hPAM4-γ1-pdHL2 used for producing the immunotoxin referred to as 2L-Rap(N69Q)-hPAM4, which is composed of two molecules of Rap, each fused to the N-terminus of the light chain of hPAM4, was digested with Sac2 and NgoM4 to remove the fragment encoding the CH1-CH3 domains, followed by ligation of the CH1-DDD1 fragment, which was excised from the plasmid vector C-DDD1-Fd-hMN-14-pdHL2 with Sac2 and NgoM4 to generate Rap-hPAM4-Fd-DDD1-pdHL2.

Production, Purification and Characterization of Rap-hPAM4-Fab-DDD1

The Rap-hPAM4-Fd-DDD1-pdHL2 vector was transfected into NS0 myeloma cells by electroporation. Rap-hPAM4-Fd-DDD1-pdHL2 is a di-cistronic expression vector, which directs the synthesis and secretion of both Rap-fused hPAM4 light chain and hPAM4-Fd-DDD1, which combine to form the Rap-Fab fusion protein. Each fusion protein forms a stable homodimer, referred to as Rap-hPAM4-Fab-DDD1, via the interaction of the DDD1 domain.

Following electroporation, the cells were plated in 96-well tissue culture plates and transfectant clones were selected with 0.05 µM methotrexate (MTX). Clones were screened for protein expression by ELISA using microtitre plates coated with WS (a rat anti-id monoclonal antibody to hPAM4) and probed with ML98-1 (a mouse monoclonal antibody to Rap) and HRP-conjugated goat anti-mouse Fc.

Figure 17:
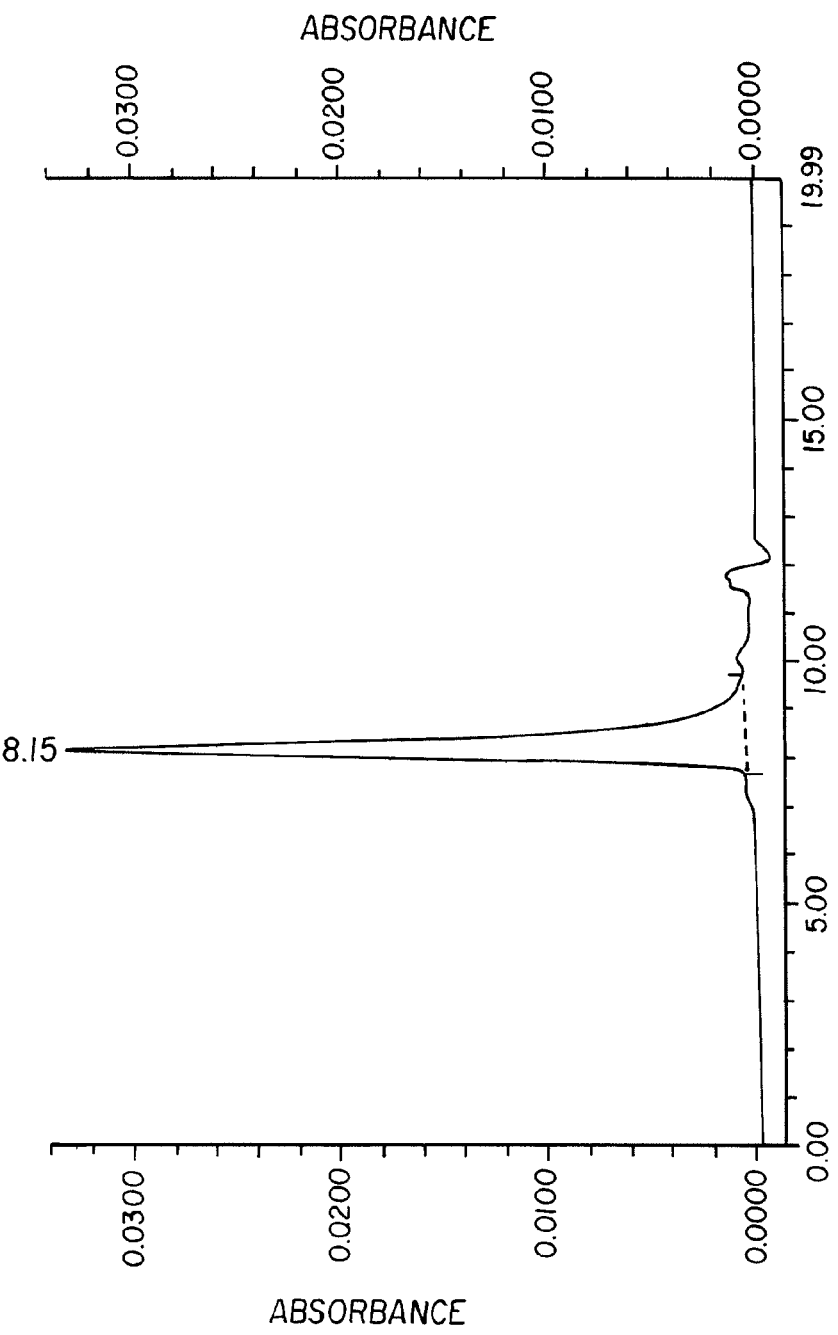
FIG. 17 shows the SE-HPLC analysis of affinity-purified Rap-hPAM4-Fab-DDD1.
Figure 18:
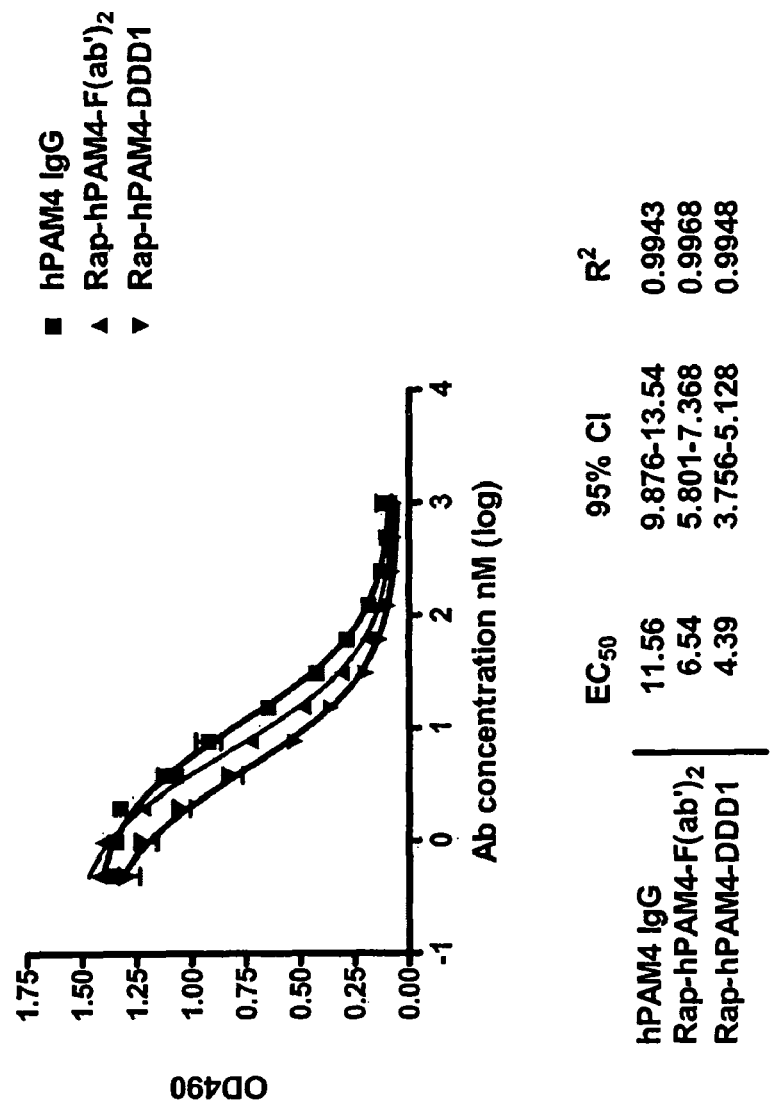
FIG. 18 shows the binding affinity of Rap-hPAM4-Fab-DDD1 is equivalent to that of hPAM4 IgG.

Rap-hPAM4-Fab-DDD1 was purified as described above using an AD1-C-affigel column. The initial productivity of the selected clone was about 0.5 mg per liter. SE-HPLC analysis (FIG. 17) of the affinity-purified Rap-hPAM4-Fab-DDD1 shows a single protein peak with a retention time (8.15 min) consistent with the expected molecular mass of ~130 kDa. The binding affinity of Rap-hPAM4-Fab-DDD1 for WS was shown to be similar to that of hPAM4 IgG (FIG. 18).

Example 4

Methods for Generating $a_4$ Constructs Composed of Four Identical Fab Fusion Proteins, each Containing the DDD2 Sequence Linked to the N-Terminus of the Fd Chain via a Peptide Spacer Construction of N-DDD2-Fd-hMN-14-pdHL2

N-DDD2-Fd-hMN-14-pdHL2 is an expression vector for producing an $a_4$ construct, referred to as the tetravalent N-DDD2-Fab-hMN-14 hereafter, that comprises four copies of a fusion protein in which the DDD2 sequence is appended to hMN-14 Fab at the N-terminus of the Fd chain via a flexible peptide spacer.

The expression vector was engineered as follows. Two overlapping, complimentary oligonucleotides (DDD2 Top and DDD2 Bottom), which comprise residues 1-13 of DDD2, were made synthetically. The oligonucleotides were annealed and phosphorylated with T4 polynucleotide kinase (PNK), resulting in overhangs on the 5' and 3' ends that are compatible for ligation with DNA digested with the restriction endonucleases NcoI and PstI, respectively

```
DDD2 Top
                                         (SEQ ID NO: 15)
5'CATGTGCGGCCACATCCAGATCCCGCCGGGGCTCACGGAGCTGCT

GCA-3'

DDD2 Bottom
                                         (SEQ ID NO: 16)
5'GCAGCTCCGTGAGCCCCGGCGGGATCTGGATGTGGCCGCA-3'
```

The duplex DNA was ligated with a vector fragment, DDD1-hMN14 Fd-SV3 that was prepared by digestion with NcoI and PstI, to generate the intermediate construct DDD2-hMN14 Fd-SV3. A 1.28 kb insert fragment, which contained the coding sequence for DDD2-hMN14 Fd, was excised from the intermediate construct with XhoI and EagI restriction endonucleases and ligated with hMN14-pdHL2 vector DNA that was prepared by digestion with those same enzymes. The final expression vector is N-DDD2-Fd-hMN-14-pdHL2.

Production, Purification and Characterization of the Tetravalent N-DDD2-Fab-hMN-14

N-DDD2-Fd-hMN-14-pdHL2 vector was transfected into Sp/EEE myeloma cells by electroporation. The di-cistronic expression vector directs the synthesis and secretion of both hMN-14 kappa light chain and N-DDD2-Fd-hMN-14, which combine to form the Fab-based subunit N-DDD2-Fab-hMN14. Following electroporation, the cells were plated in 96-well tissue culture plates and transfectant clones were selected with 0.05 µM methotrexate (MTX).

Figure 19:
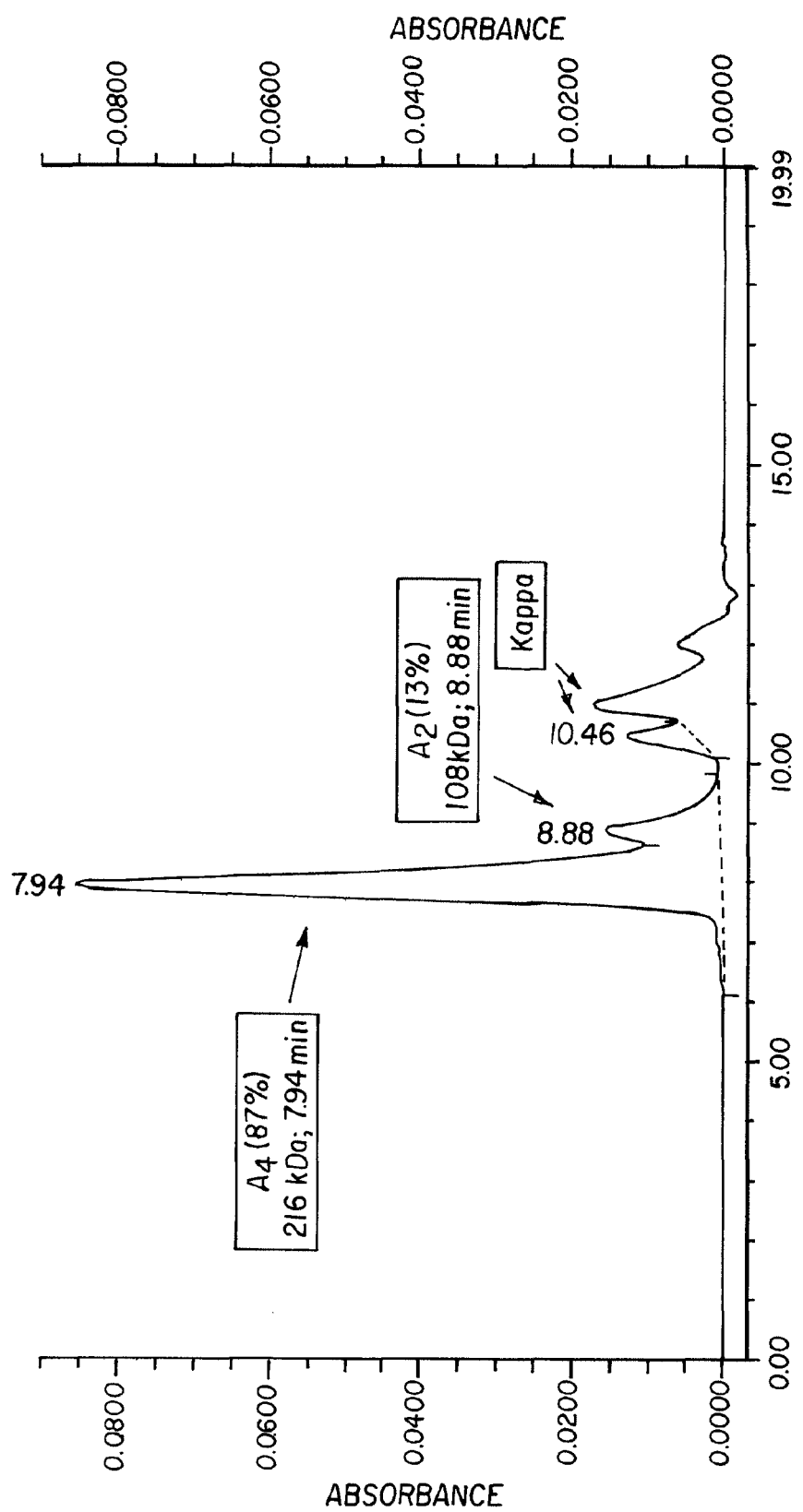
FIG. 19 shows the predominant presence of the $a_4$ form in N-DDD2-Fab-hMN-14 purified with CBind L (Protein L cellulose). The SE-HPLC trace also reveals the presence of the $a_2$ form, as well as free light chains in both monomeric and dimeric forms.
Figure 20:
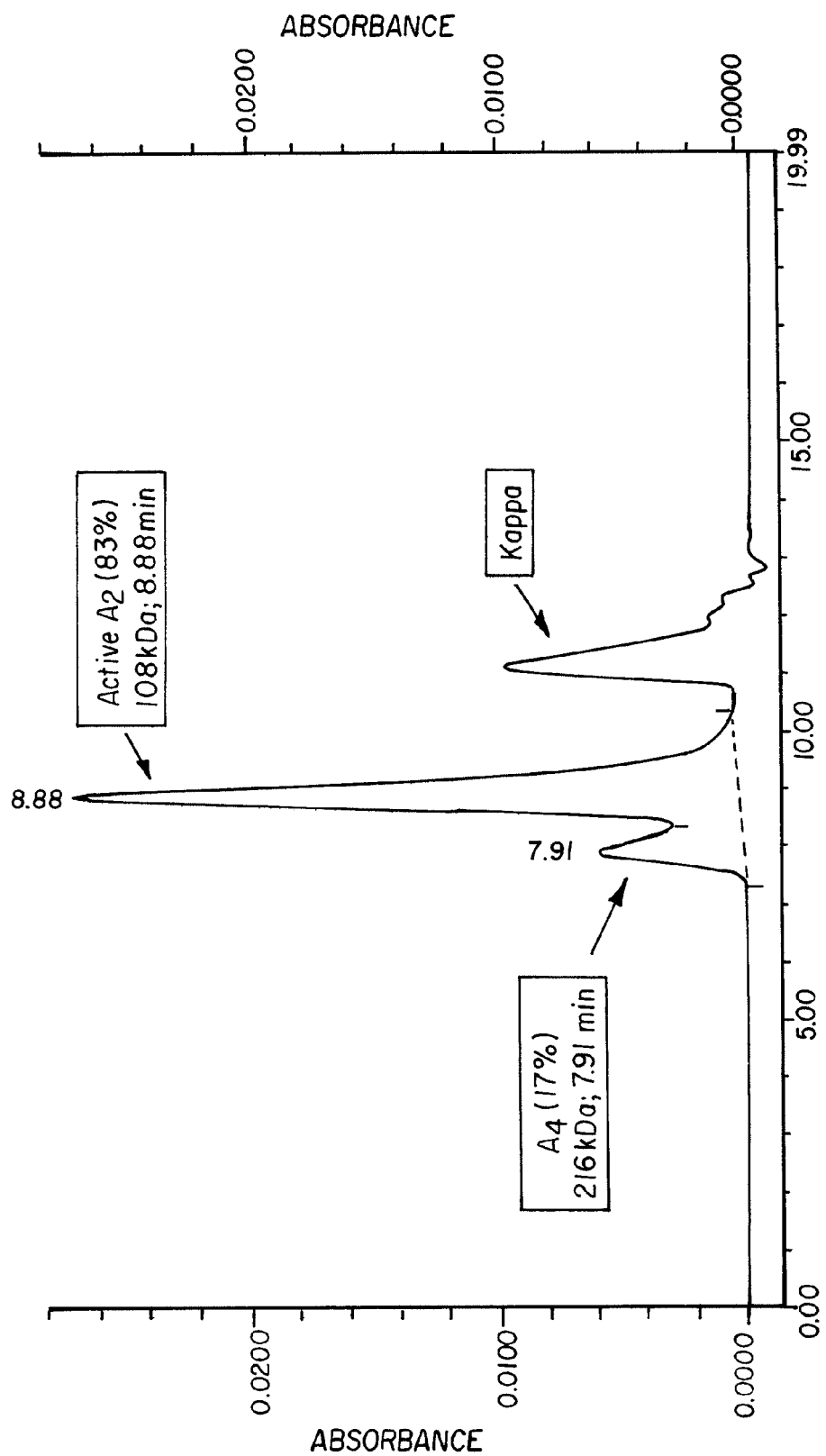
FIG. 20 shows the dissociation of the $a_4$ form present in purified N-DDD2-Fab-hMN-14 to the $a_2$ form upon reduction with 5 mM TCEP, which also converts the dimeric light chain to monomeric light chain.

Clones were screened for protein expression by ELISA using microtitre plates coated with WI2 (hMN-14 anti-Id) and detection was achieved with goat anti-human Fab-HRP. The highest producing clones had an initial productivity of approximately 10 mg/L. A total of 16 mg of N-DDD2-hMN-14 was purified by protein L affinity chromatography from 1.8 liters of roller bottle culture. Culture supernatants were concentrated approximately 10-fold by ultrafiltration before loading onto a protein L column. The column was washed to baseline with PBS and N-DDD2-Fab-hMN14 was eluted with 1 mM EDTA, 0.1 M NaAc, pH 2.5 and immediately neutralized with Tris-HCl. SE-HPLC analysis (FIG. 19) showed four protein peaks, two of which were subsequently attributed to the tetrameric $a_4$ (7.94 min) and dimeric $a_2$ (8.88 min) forms of N-DDD2-Fab-hMN-14 and the remaining two were the dimer and monomer of the kappa chain. Most of the tetrameric $a_4$ form in the mixture was converted to the dimeric $a_2$ form (FIG. 20) upon adding a thiol reducing agent such as TCEP, suggesting that the tetrameric $a_4$ form apparently is composed of two dimeric $a_2$ structures linked through intermolecular disulfide bridges formed between the cysteines present in DDD2. It is noted that approximately 15% of the total N-DDD2-Fab-hMN-14 remains in the $a_4$ form following reduction, even with high TCEP concentrations and long reaction times, suggesting that other mechanisms such as domain swapping may contribute to the formation of the $a_4$ form, in addition to disulfide bridging. The tetravalent N-DDD2-Fab-hMN-14 was separated from other molecular forms by gel filtration chromatography using a Superdex-200 column.

Example 5

Methods for Generating $a_4$ Constructs Composed of Four Identical Fab Fusion Proteins, each Containing the DDD2 Sequence Linked to the C-Terminus of the Fd Chain via a Peptide Spacer Construction of C-DDD2-Fd-hMN-14-pdHL2

C-DDD2-Fd-hMN-14-pdHL2 is an expression vector for producing an $a_4$ construct, referred to as the tetravalent C-DDD2-Fab-hMN-14 hereafter, that comprises four copies of a fusion protein in which the DDD2 sequence is appended to hMN-14 Fab at the C-terminus of the Fd chain via a flexible peptide spacer.

The expression vector was engineered as follows. Two overlapping, complimentary oligonucleotides, which comprise the coding sequence for part of the linker peptide (GGGGSGGGCG) and residues 1-13 of DDD2, were made synthetically. The oligonucleotides were annealed and phosphorylated with T4 PNK, resulting in overhangs on the 5' and 3' ends that are compatible for ligation with DNA digested with the restriction endonucleases BamHI and PstI, respectively.

```
G4S-DDD2 top
                                         (SEQ ID NO: 17)
5'GATCCGGAGGTGGCGGGTCTGGCGGAGGTTGCGGCCACATCCAGATC

CCGCCGGGGCTCACGGAGCTGCTGCA-3'

G4S-DDD2 bottom
                                         (SEQ ID NO: 18)
5'GCAGCTCCGTGAGCCCCGGCGGGATCTGGATGTGGCCGCAACCTCCGC

CAGACCCGCCACCTCCG-3'
```

The duplex DNA was ligated with the shuttle vector CH1-DDD1-pGemT, which was prepared by digestion with BamHI and PstI, to generate the shuttle vector CH1-DDD2-pGemT. A 507 bp fragment was excised from CH1-DDD2-pGemT with SacII and EagI and ligated with the IgG expression vector hMN14(I)-pdHL2, which was prepared by digestion with SacII and EagI. The final expression construct is C-DDD2-Fd-hMN-14-pdHL2.

Construction of C-DDD2-Fd-hA20-pdHL2

C-DDD2-Fd-hA20-pdHL2 is an expression vector for producing an $a_4$ construct, referred to as the tetravalent C-DDD2-Fab-hA20 hereafter, that comprises four copies of a fusion protein in which the DDD2 sequence is appended to hA20-

Fab at the C-terminus of the Fd chain via a flexible peptide spacer. hA20 is a humanized monoclonal antibody specific for CD20.

The expression vector was engineered in three steps as follows. First, the expression vector hA20-IgG-pdHL2 was digested with Sac2 and NdeI to yield the 7578-bp fragment. Next, the expression vector C-DDD2-hMN-14-Fd-pdHL2 was digested with Sac2 and NdeII and the 509-bp fragment coding for CH1-DDD2 was isolated. Third, the 7578-bp fragment was ligated with the 509-bp fragment to generate C-DDD2-Fd-hA20-phHL2.

Construction of C-DDD2-Fd-hMN-3-pdHL2

C-DDD2-Fd-hMN3-pdHL2 is an expression vector for producing an $a_4$ construct, referred to as the tetravalent C-DDD2-Fab-hMN-3 hereafter, that comprises four copies of a fusion protein in which the DDD2 sequence is appended to hMN3-Fab at the C-terminus of the Fd chain via a flexible peptide spacer. hMN-3 is a humanized monoclonal antibody specific for the N domain of CEA (CEACAM5) or NCA-90 (CEACAM6).

The expression vector was engineered in three steps as follows. First, the expression vector hMN-3-IgG-pdHL2 was digested with Sac2 and NgoM4 to yield the 8118-bp fragment. Next, the expression vector C-DDD2-hMN-14-Fd-pdHL2 was digested with Sac2 and NgoM4 and the 509-bp fragment coding for CH1-DDD2 was isolated. Third, the 8118-bp fragment was ligated with the 509-bp fragment to generate C-DDD2-Fd-hMN-3-phHL2.

Construction of C-DDD2-Fd-hLL2-pdHL2

C-DDD2-Fd-hLL2-pdHL2 is an expression vector for producing an $a_4$ construct, referred to as the tetravalent C-DDD2-Fab-hLL2 hereafter, that comprises four copies of a fusion protein in which the DDD2 sequence is appended to hLL2-Fab at the C-terminus of the Fd chain via a flexible peptide spacer. hLL2 is a humanized monoclonal antibody specific for CD22.

The expression vector was engineered in three steps as follows. First, the expression vector hLL2-IgG-pdHL2 was digested with Sac2 and NdeI to yield the 7578-bp fragment. Next, the expression vector C-DDD2-hMN-14-Fd-pdHL2 was digested with Sac2 and NdeI and the 509-bp fragment coding for CH1-DDD2 was isolated. Third, the 7578-bp fragment was ligated with the 509-bp fragment to generate C-DDD2-hLL2-phHL2.

Production, Purification and Characterization of the Tetravalent C-DDD2-Fab-hMN-14

C-DDD2-Fd-hMN-14-pdHL2 vector was transfected into Sp/EEE myeloma cells by electroporation. The di-cistronic expression vector directs the synthesis and secretion of both hMN-14 kappa light chain and C-DDD2-Fd-hMN-14, which combine to form C-DDD2-Fab-hMN14. Following electroporation, the cells were plated in 96-well tissue culture plates and transfectant clones were selected with 0.05 µM methotrexate (MTX).

Figure 21:
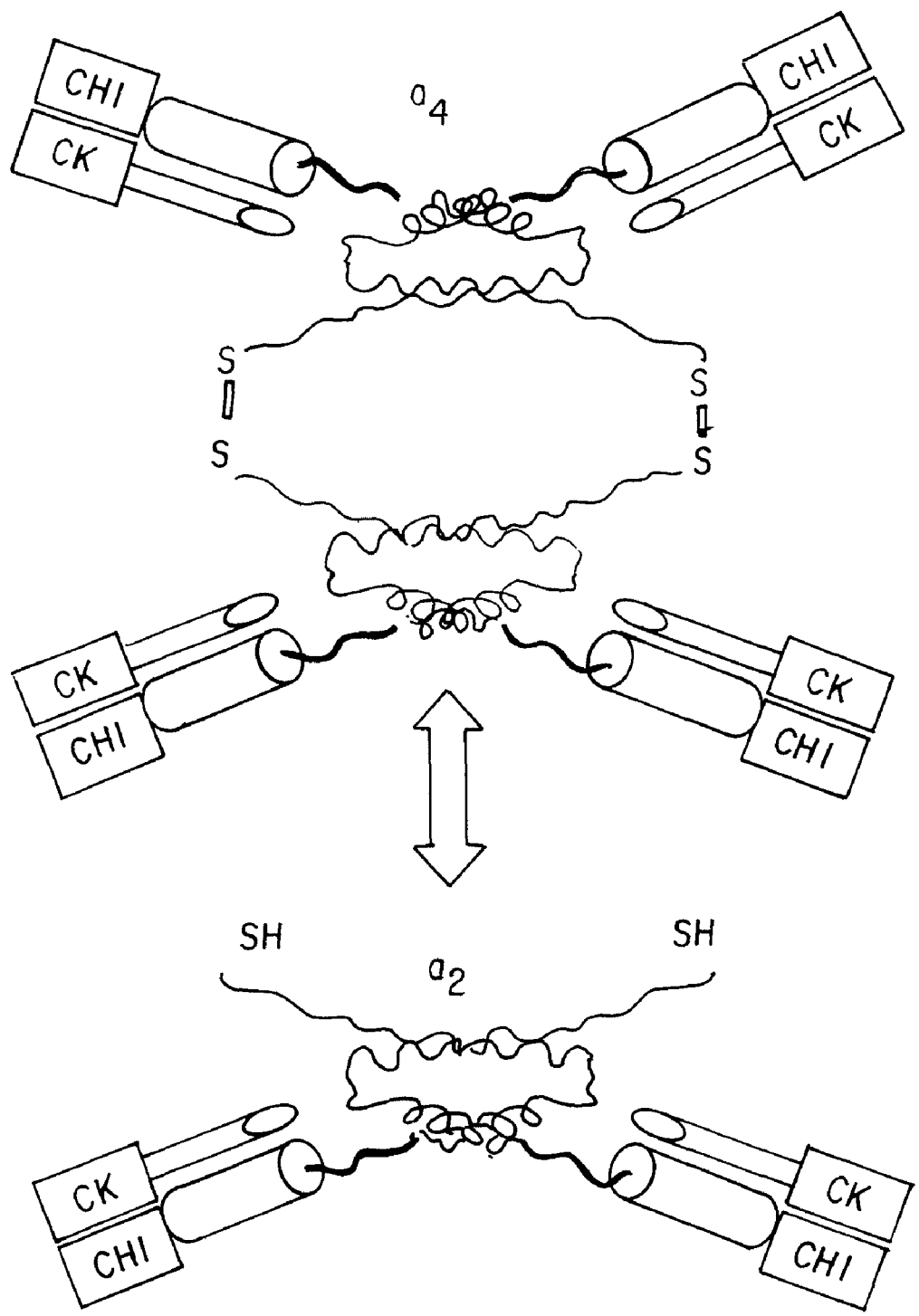
FIG. 21 shows a schematic representation of the conversion of C-DDD2-Fab-hMN-14 in the $a_4$ form to the $a_2$ form upon reduction.
Figure 22:
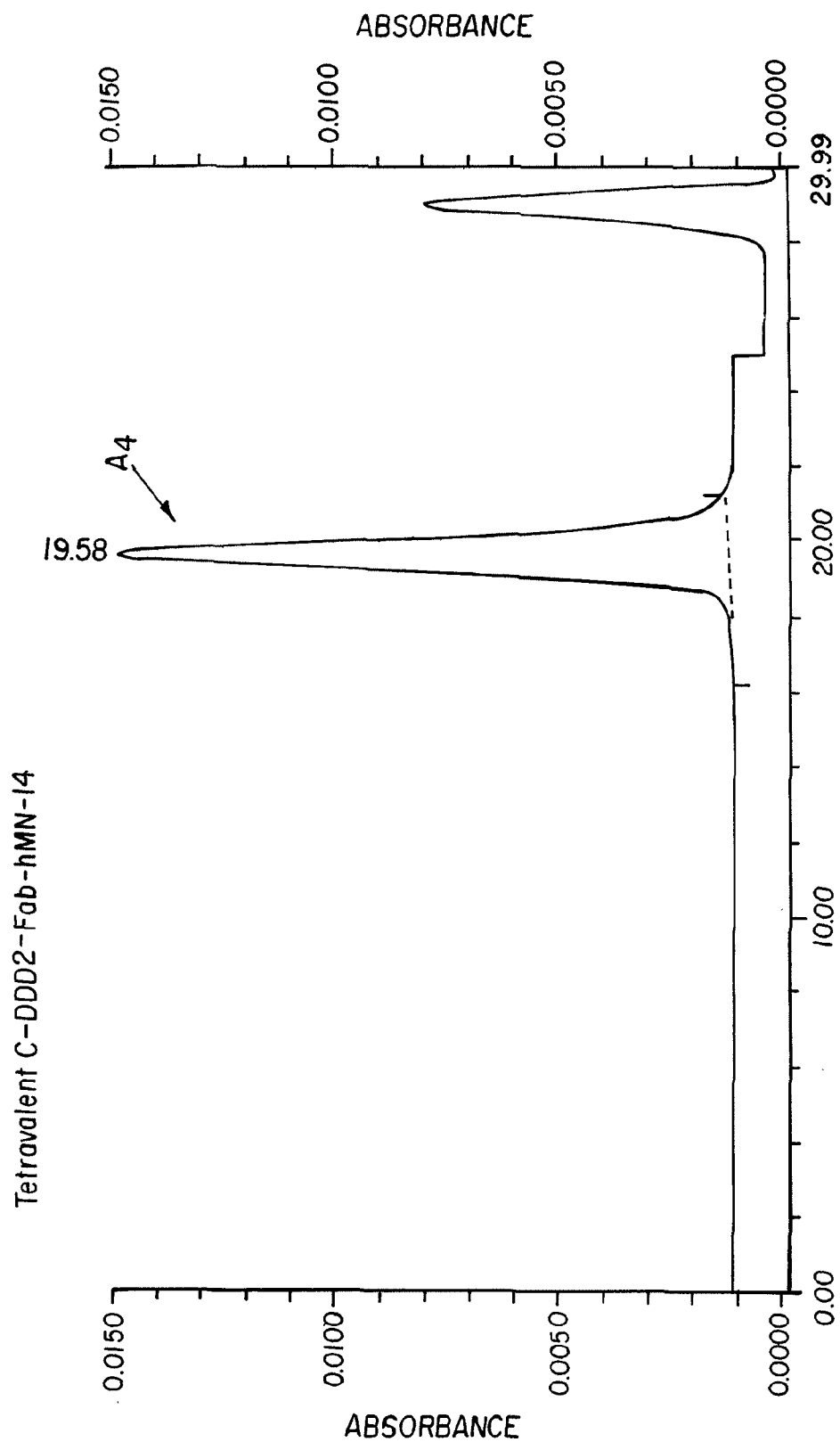
FIG. 22 shows the SE-HPLC analysis of the tetravalent C-DDD2-Fab-hMN-14 after purification by Superdex-200 gel filtration chromatography. Two columns (Biosil SEC 250) were connected in tandem for increased resolution. The tetravalent C-DDD2-Fab-hMN-14 appears as a single peak (indicated as $A_4$) with a retention time of 19.58 min.

Clones were screened for protein expression by ELISA using microtitre plates coated with WI2 (hMN-14 anti-Id) and detection was achieved with goat anti-human Fab-HRP. The highest producing clones had an initial productivity of approximately 10 mg/L, which was 10-fold higher than that of N-DDD2-Fab-hMN-14. A total of 200 mg of C-DDD2-Fab-hMN-14 was purified by protein L affinity chromatography from 1.8 liters of roller bottle culture as described above for N-DDD2-Fab-hMN-14. The SE-HPLC profile of the Protein L-purified C-DDD2-Fab-hMN-14 was similar to that of N-DDD2-Fab-hMN-14, showing four protein peaks. Two of the four protein peaks were attributed to the tetrameric $a_4$ (8.40 min) and dimeric $a_2$ (9.26 min) forms of C-DDD2-Fab-hMN-14 and the remaining two represent dimer and monomer of the kappa chain. The tetravalent C-DDD2-Fab-hMN-14 was separated from other molecular forms by gel filtration chromatography using a SUPERDEX®-200 column. Like N-DDD2-Fab-hMN-14, addition of TCEP converts most of the $a_4$ form to the $a_2$ form, as illustrated in FIG. 21. The SE-HPLC profile of the tetravalent C-DDD2-Fab-hMN-14 on a tandem column system is shown in FIG. 22, appearing as a single peak with a retention time of 19.57min. The ability of the tetravalent C-DDD2-Fab-hMN-14 to bind to four WI2 fragments is shown in FIG. 23.

Production, Purification and Characterization of the Tetravalent C-DDD2-Fab-hA20

C-DDD2-Fd-hA20-pdHL2 vector was transfected into NS0 myeloma cells by electroporation. The di-cistronic expression vector directs the synthesis and secretion of both hA20 kappa light chain and C-DDD2-Fd-hA20, which combine to form C-DDD2-Fab-hA20. Following electroporation, the cells were plated in 96-well tissue culture plates and transfectant clones were selected with 0.05 µM methotrexate (MTX).

Figure 24:
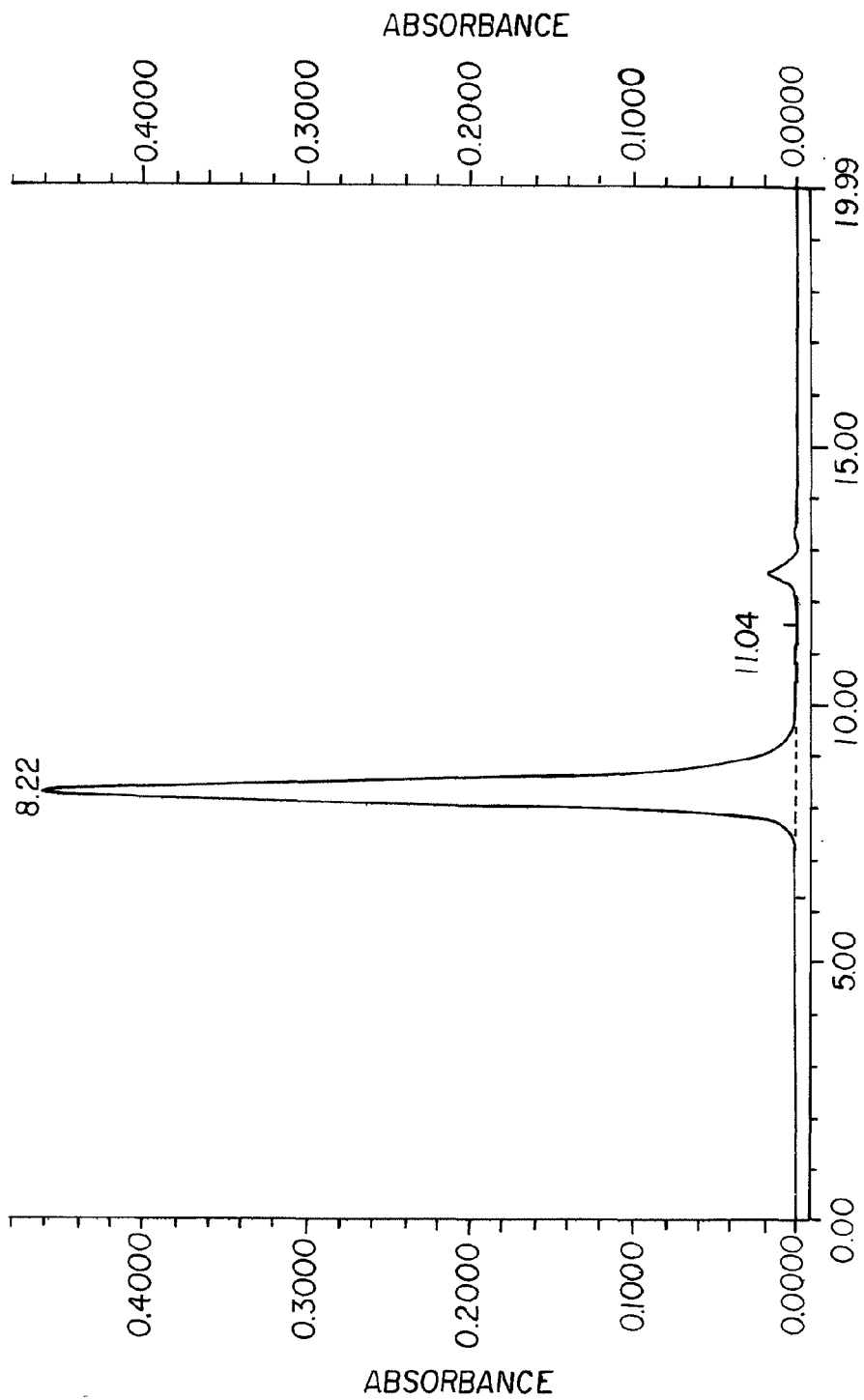
FIG. 24 shows SE-HPLC analysis of the tetravalent C-DDD2-Fab-hA20 after purification by Superdex-200 gel filtration chromatography.
Figure 25:
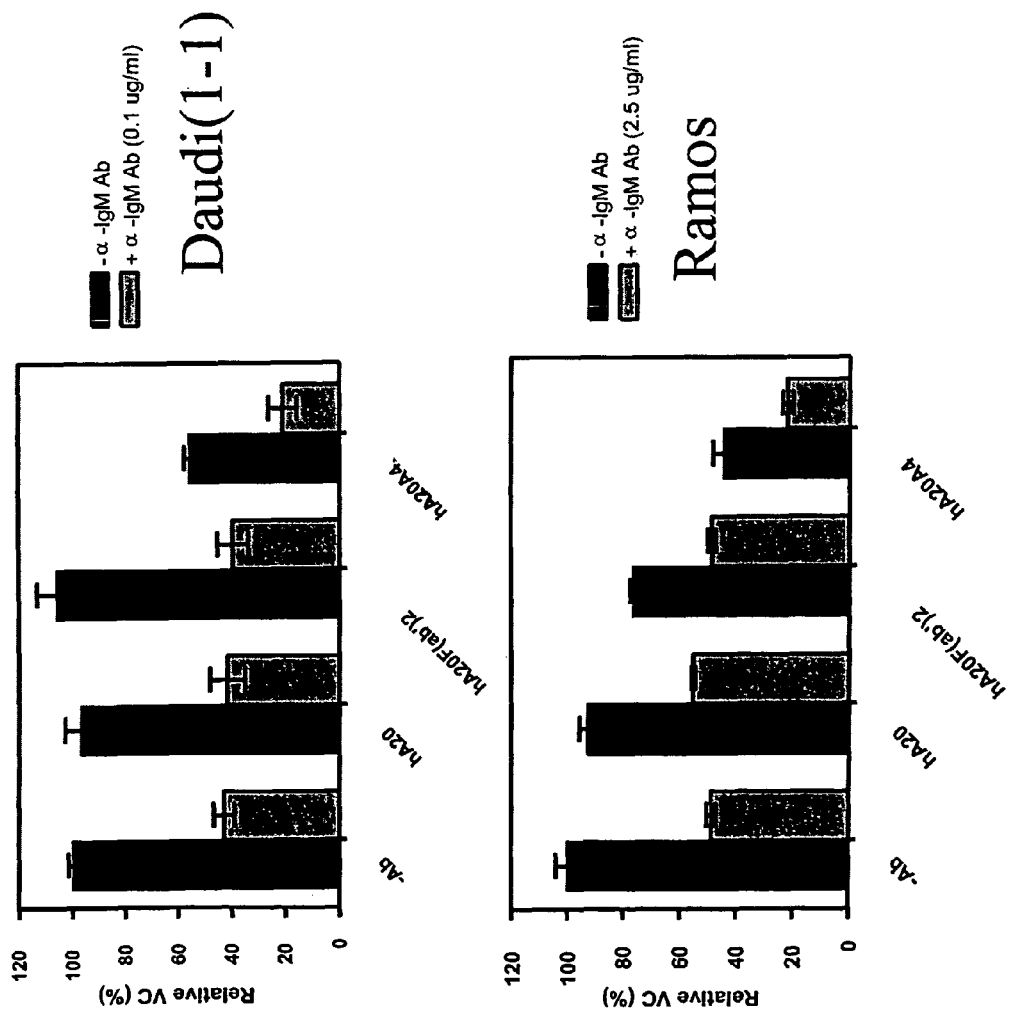
FIG. 25 shows cell growth inhibition by the tetravalent C-DDD2-Fab-hA20 (abbreviated as hA20A4). Daudi (1-1) cells (upper panel) or Ramos cells (lower panel) were resuspended in 48-well plates in duplicate at a final density of 100,000 cells/mL in the complete medium containing 10 nM of hA20, hA20 F(ab')$_2$, or hA20A4, in the absence or presence of anti-IgM (0.1 ug/mL). The cells were incubated for 3 days and MTT assay was performed to determine the viable cell populations. Only hA20A4 caused significant growth inhibition (40 to 50%) in the absence of anti-IgM.

Clones were screened for protein expression by ELISA using microtitre plates coated with WR2 (a rat anti-id to hA20) and detection was achieved with goat anti-human Fab-HRP. The highest producing clones had an initial productivity of approximately 10 mg/L. The tetravalent C-DDD2-Fab-hA20 was purified from cell culture supernatants produced in roller bottles by Protein L affinity chromatography followed by SUPERDEX®-200 gel filtration. The SE-HPLC profile of the tetravalent C-DDD2-Fab-hA20 is shown in FIG. 24. The tetravalent C-DDD2-Fab-hA20 showed potent anti-proliferative activity on Daudi and Ramos even in the absence of anti-IgM (FIG. 25). By contrast, the bivalent hA20 IgG or F(ab')2 was inactive in inhibiting the growth of Daudi or Ramos under the same conditions either in the absence or presence of anti-IgM. The observed anti-proliferative activity of hA20 IgG or F(ab')2 in the presence of anti-IgM was apparently due to that of anti-IgM.

Production and Purification of the Tetravalent C-DDD2-Fab-hMN-3

C-DDD2-Fd-hMN-3-pdHL2 vector was transfected into NS0 myeloma cells by electroporation. The di-cistronic expression vector directs the synthesis and secretion of both hMN-3 kappa light chain and C-DDD2-Fd-hMN-3, which combine to form C-DDD2-Fab-hMN-3. Following electroporation, the cells were plated in 96-well tissue culture plates and transfectant clones were selected with 0.05 µM methotrexate (MTX).

Clones were screened for protein expression by ELISA using microtitre plates coated with CEACAM5 and detection was achieved with goat anti-human Fab-HRP. The highest producing clones had an initial productivity of approximately 10 mg/L. The tetravalent C-DDD2-Fab-hMN-3 was purified from cell culture supernatants produced in roller bottles by Protein L affinity chromatography followed by Superdex-200 gel filtration.

Production and Purification of the Tetravalent C-DDD2-Fab-hLL2

C-DDD2-Fd-hLL2-pdHL2 vector was transfected into Sp2/0-derived myeloma cells by electroporation. The di-cistronic expression vector directs the synthesis and secretion of both hLL2 kappa light chain and C-DDD2-Fd-hLL2, which combine to form C-DDD2-Fab-hLL2. Following electroporation, the cells were plated in 96-well tissue culture plates and transfectant clones were selected with 0.05 µM methotrexate (MTX).

Clones were screened for protein expression by ELISA using microtitre plates coated with WN (a rat anti-id to hLL2) and detection was achieved with goat anti-human Fab-HRP. The highest producing clones had an initial productivity of approximately 15 mg/L. The tetravalent C-DDD2-Fab-hLL2 was purified from cell culture supernatants produced in roller bottles by Protein L affinity chromatography followed by SUPERDEX®-200 gel filtration.

Example 6

Methods for Generating $a_2a'_2$ Constructs from Two Distinct $a_4$ and $a'_4$ Constructs Production, Purification and Characterization of the Bispecific Tetravalent C-DDD2-Fab-hMN-3 x C-DDD2-Fab-hA20.

Figure 26:
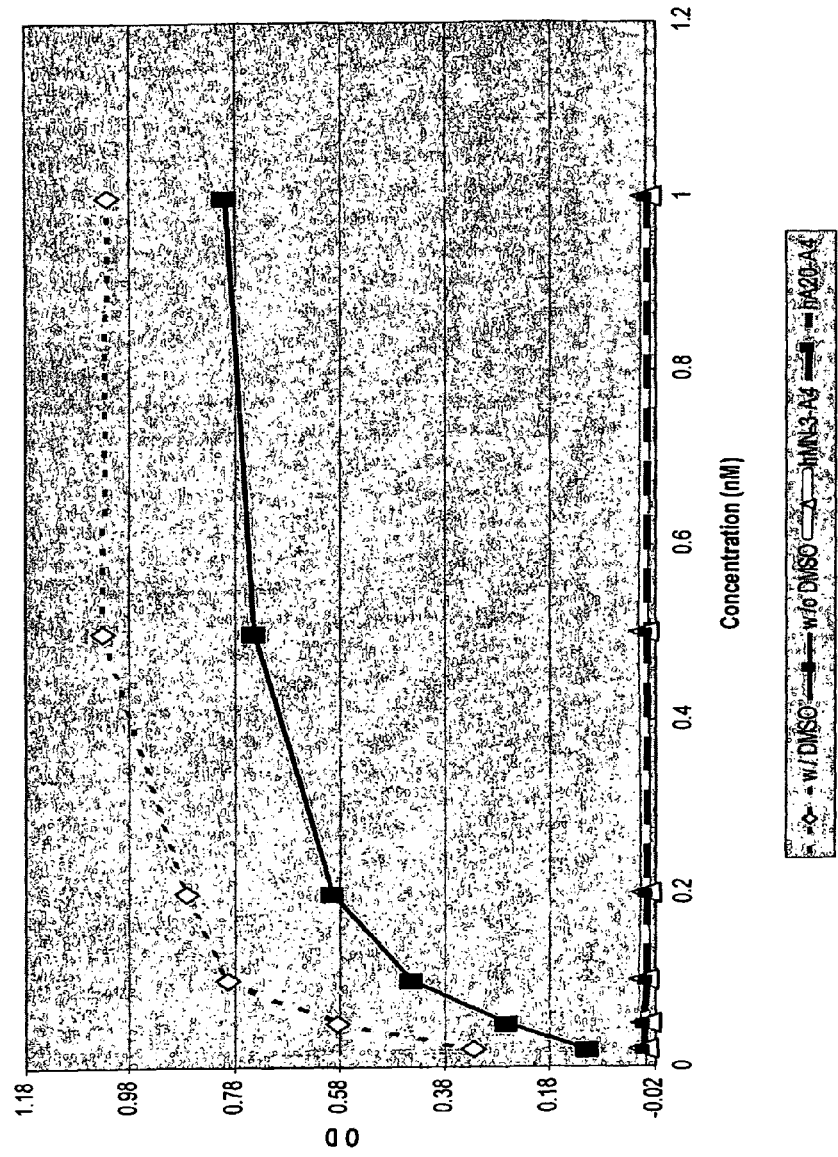
FIG. 26 shows the presence of the bispecific tetravalent hMN-3xhA20 by ELISA.

The tetravalent C-DDD2-Fab-hMN-3 and the tetravalent C-DDD2-Fab-hA20 obtained from Example 5 were combined and reduced with 1 mM glutathione at RT for 1 h followed by adding oxidized glutathione to a final concentration of 2 mM. The tetrameric fraction was purified from the other molecular forms by gel filtration on a SUPERDEX®-200 column. The formation of the bispecific tetravalent C-DDD2-Fab-hMN-3 x C-DDD2-Fab-hA20 was demonstrated by ELISA using plates coated with CEACAM5 and probed with WR2, as shown in FIG. 26.

Production, Purification and Characterization of the Bispecific Tetravalent C-DDD2-Fab-hMN-3 x C-DDD2-Fab-hMN-14

Figure 27:
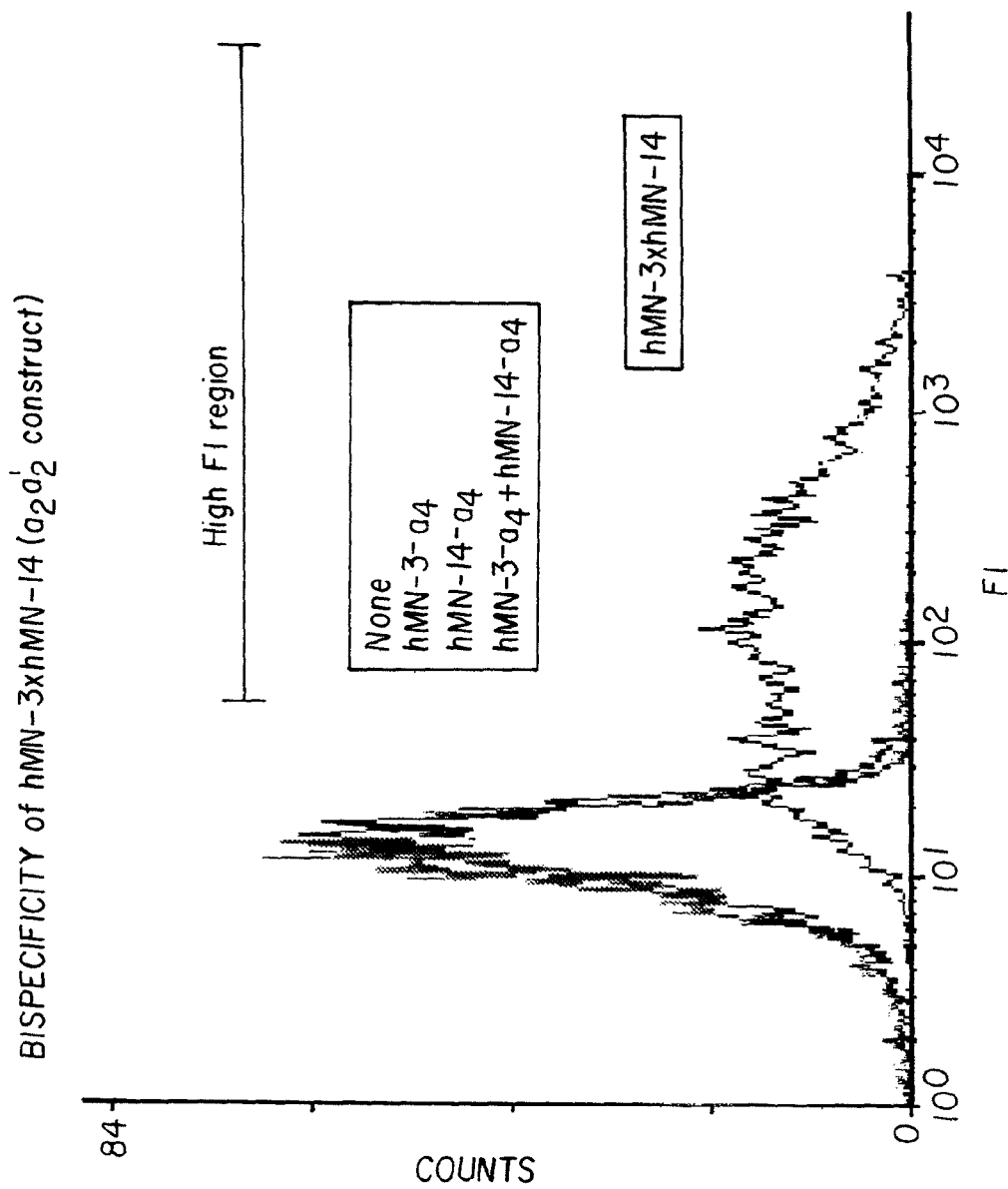
FIG. 27 shows the presence of bispecific tetravalent hMN-3xhMN-14 by flow cytometry. BXPC3 cells, which express high levels of CEACAM6 but only background levels of CEACAM5,were incubated for 1 h at RT with each of the samples (10 ug/mL) in the presence of Alexa-532-WI2, a rat anti-ideotypic mAb for hMN-14 labeled with a fluorescent tag, and analyzed by flow cytometry using Guava PCA. Only the histogram of the sample containing bispecific hMN-3xhMN-14 showed positively stained BXPC3 cells.

The tetravalent C-DDD2-Fab-hMN-3 and the tetravalent C-DDD2-Fab-hMN-14 obtained from Example 5 were combined and reduced with 1 mM glutathione at RT for 1 h followed by adding oxidized glutathione to a final concentration of 2 mM. The tetrameric fraction was purified from the other molecular forms by gel filtration on a SUPERDEX®-200 column. The formation of the bispecific tetravalent C-DDD2-Fab-hMN-3 x C-DDD2-Fab-hMN-14 was demonstrated by flow cytometry using BXPC3 cells as shown in FIG. 27.

Production and Purification of the Bispecific Tetravalent C-DDD2-Fab-hA20 x C-DDD2-Fab-hLL2

The tetravalent C-DDD2-Fab-hA20 and the tetravalent C-DDD2-Fab-hLL2 obtained from Example 5 were combined and reduced with 1 mM glutathione at RT for 1 h followed by adding oxidized glutathione to a final concentration of 2 mM. The tetrameric fraction was purified from the other molecular forms by gel filtration on a Superdex-200 column. The formation of the bispecific tetravalent C-DDD2-Fab-hA20 x C-DDD2-Fab-hLL2 was demonstrated by ELISA using plates coated with WN (a rat anti-id to hLL2) and probed with WR2 (a rat anti-id to hA20).

TABLE 1

Selected Examples of Type I Products for which the subunits of $a_2$ are based on binding domains derived from immunoglobulins

| Target | Application |
|---|---|
| X | Treating or detecting a disease bearing the X marker |
| CD14 | Treating septic shock |
| CD111/nectin-1 | Treating herpesvirus infection |
| Folate receptor α | Treating filovirus infection (e.g. Ebola and Marburg viruses) |
| gp120 | Treating HIV-1/AIDS |
| IL-6 | Treating myeloma, arthritis and other autoimmune disease |
| IL-5 | Treating asthma |
| IL-8 | Treating general infection |
| CD154 | Treating lupus, transplant rejection, AID |
| IgE | Treating asthma as indicated by Xolair ® |
| LFA-1 | Treating transplant rejection |
| CD3 | Treating transplant rejection as indicated by OKT3 ® |
| β-tryptase | Treating allergy, inflammation |
| CD105/endoglin | Anti-angiogenesis |
| GpIIb/IIa | Treating thrombosis as indicated by RepPro ™ |
| TNF-α | Treating arthritis as indicated by HUMIRA ™ or REMICADE ® |
| RSV F-protein | RSV therapy as indicated by Synagis ™ |
| A1B1 of CEA | Inhibiting adhesion/invasion/metastasis of solid cancers |
| N domain of CEA | Inhibiting adhesion/invasion/metastasis of solid cancers |
| Pgp/p-170 | Reversing multiple drug resistance |
| VEGF | Neutralizing VEGF |
| Placenta growth factor (PlGF) | Neutralizing |
| VEGFR1/Flt-1 | Treating cancers |
| Blys/CD257 | Treating lupus and arthritis |
| APRIL/CD256 | Treating lupus and arthritis |

TABLE 2

Selected Examples of Type 2 Products for which the subunits of $a_2$ are based on nonimmunoglobulin proteins

| Precursor | Application |
|---|---|
| Soluble Tumor necrosis factor receptor (sTNFR) | Treating arthritis as indicated by Enbrel ® |
| sTNFR-VL-CL | Treating arthritis as indicated by Enbrel ® |
| sTNFR-CH2-CH3 | Treating arthritis as indicated by Enbrel ® |
| Ranpirnase (Rap) | Treating cancers |
| Rap-VL-CL | Treating cancers |
| Rap-CH2-CH3 | Treating cancers |
| Tissue plasminogen activator (tPA) | Treating diseases as indicated by Activase ® |
| tPA-VL-CL | Treating diseases as indicated by Activase ® |
| tPA-CH2-CH3 | Treating diseases as indicated by Activase ® |
| Erythropoietin (EPO) | Treating anemia as indicated by Epogen ® |
| EPO-VL-CL | Treating anemia as indicated by Epogen ® |
| EPO-CH2-CH3 | Treating anemia as indicated by Epogen ® |
| Thrombopoietin (TPO) | Treating thrombocytopenia |
| TPO-VL-CL | Treating thrombocytopenia |
| TPO-CH2-CH3 | Treating thrombocytopenia |
| Interlukin (IL)-11 | Treating thrombocytopenia as indicated by Neumega ® |
| IL-11-VL-CL | Treating thrombocytopenia as indicated by Neumega ® |
| IL-11-CH2-CH3 | Treating thrombocytopenia as indicated by Neumega ® |
| Granulocyte-colony stimulating factor (G-CSF) | Treating neutropenia as indicated by Neupogen ® |
| G-CSF-VL-CL | Treating neutropenia as indicated by Neupogen ® |
| G-CSF-CH2-CH3 | Treating neutropenia as indicated by Neupogen ® |
| Interferon (IFN)-α2 | Treating hepatitis as indicated by Intron A ® |
| IFN-α2-VL-CL | Treating hepatitis as indicated by Intron A ® |
| IFN-α2-CH2-CH3 | Treating hepatitis as indicated by Intron A ® |
| IFN-β1 | Treating multiple sclerosis as indicated by Betaseron ® |
| IFN-β1-VL-CL | Treating multiple sclerosis as indicated by Betaseron ® |
| IFN-β1-CH2-CH3 | Treating multiple sclerosis as indicated by Betaseron ® |
| Coagulation factor IX | Treating hemophilia B as indicated by BeneFix ™ |
| Coagulation factor IX-VL-CL | Treating hemophilia B as indicated by BeneFix ™ |
| Coagulation factor-IX-CH2-CH3 | Treating hemophilia B as indicated by BeneFix ™ |

TABLE 2-continued

Selected Examples of Type 2 Products for which the subunits of $a_2$ are based on nonimmunoglobulin proteins

| Precursor | Application |
| --- | --- |
| GM-CSF | Treating diseases as indicated by Leukine ® |
| GM-CSF-VL-CL | Treating diseases as indicated by Leukine ® |
| GM-CSF-CH2-CH3 | Treating diseases as indicated by Leukine ® |
| PlGF antagonist peptides | Neutralizing |
| VEGF antagonist peptides | Neutralizing VEGF |
| Tyrosine kinase inhibitors | Treating cancers |
| Aβ12-28P fused to CH2-CH3 | Treating Alzheimer's disease |

TABLE 3

Selected Examples of Type 3 Products for which the subunits of $a_4$ are based on binding domains derived from immunoglobulins

| Target | Application |
| --- | --- |
| X | Treating or detecting a disease bearing the X marker |
| CD14 | Treating septic shock |
| CD111/nectin-1 | Treating herpes simplex virus infection |
| Folate receptor α | Treating Filovirus infection (e.g. Ebola and Marburg viruses) |
| gp120 | Treating HIV-1/AIDS |
| IL-6 | Treating myeloma, arthritis and other autoimmune disease |
| IL-5 | Treating asthma |
| IL-8 | Treating general infection |
| CD154 | Treating lupus, transplant rejection, AID |
| IgE | Treating asthma as indicated by Xolair ® |
| LFA-1 | Treating transplant rejection |
| β-tryptase | Treating allergy, inflammation |
| CD105/endoglin | Anti-angiogenesis |
| GpIIb/IIa | Treating thrombosis as indicated by RepPro ™ |
| TNF-α | Treating arthritis as indicated by HUMIRA ™ or REMICADE ® |
| RSV F-protein | RSV therapy as indicated by Synagis ™ |
| A1B1 of CEA | Inhibiting adhesion/invasion/metastasis of solid cancers |
| N domain of CEA | Inhibiting adhesion/invasion/metastasis of solid cancers |
| CD20 | Treating B-cell lymphomas or autoimmune diseases, as indicated by Rituxan ™ |
| CD22 | Treating B-cell lymphomas or autoimmune diseases |
| CD19 | Treating B-cell lymphoma or autoimmune diseases |
| CD80 | Lymphoma therapy |
| HLA-DR | Treating cancers or autoimmune diseases |
| CD74 | Treating cancers or autoimmune diseases |
| MUC1 | Treating cancers |
| HER2/neu | Treating cancers |
| EGFR | Treating cancers |
| Insulin-like growth factor | Treating cancers |
| MIF | Treating autoimmune diseases |
| CD83 | Treating autoimmune diseases |
| CD3 | Treating transplant rejection as indicated by OKT3 ® |
| IL-2Rα/CD25 | Preventing kidney transplant rejection as indicated by Zenapax ® or Simulect ® |
| ICAM-1 | Preventing human rhinovirus infection |
| Pgp/p-170 | Reversing multiple drug resistance |
| VEGF | Neutralizing VEGF |
| PlGF | Neutralizing |
| VEGFR1/Flt-1 | Treating cancers |
| Blys/CD257 | Treating lupus and arthritis |
| April/CD256 | Treating lupus and arthritis |

TABLE 4

Selected Examples of Type 4 Products for which the subunits of $a_4$ are based on nonimmunoglobulin proteins

| Precursor | Application |
| --- | --- |
| sTNFR | Treating arthritis as indicated by Enbrel ® |
| sTNFR-VL-CL | Treating arthritis as indicated by Enbrel ® |
| sTNFR-CH2-CH3 | Treating arthritis as indicated by Enbrel ® |
| Rap | Treating cancers |
| Rap-VL-CL | Treating cancers |
| Rap-CH2-CH3 | Treating cancers |
| tPA | Treating diseases as indicated by Activase ® |
| tPA-VL-CL | Treating diseases as indicated by Activase ® |
| tPA-CH2-CH3 | Treating diseases as indicated by Activase ® |
| EPO | Treating anemia as indicated by Epogen ® or Aranesp ® |
| EPO-VL-CL | Treating anemia as indicated by Epogen ® or Aranesp ® |
| EPO-CH2-CH3 | Treating anemia as indicated by Epogen ® or Aranesp ® |
| TPO | Treating thrombocytopenia |
| TPO-VL-CL | Treating thrombocytopenia |
| TPO-CH2-CH3 | Treating thrombocytopenia |
| IL-11 | Treating thrombocytopenia as indicated by Neumega ® |
| IL-11-VL-CL | Treating thrombocytopenia as indicated by Neumega ® |
| IL-11 -CH2-CH3 | Treating thrombocytopenia as indicated by Neumega ® |
| G-CSF | Treating neutropenia as indicated by Neupogen ® |
| G-CSF-VL-CL | Treating neutropenia as indicated by Neupogen ® |
| G-CSF-CH2-C1-13 | Treating neutropenia as indicated by Neupogen ® |
| IFN-α2 | Treating hepatitis as indicated by Intron A ® |
| IFN-α2-VL-CL | Treating hepatitis as indicated by Intron A ® |
| IFN-α2-CH2-C113 | Treating hepatitis as indicated by Intron A ® |
| IFN-β1 | Treating multiple sclerosis as indicated by Betaseron ® |
| IFN-β1-VL-CL | Treating multiple sclerosis as indicated by Betaseron ® |
| IFN-β1 -CH2-CH3 | Treating multiple sclerosis as indicated by Betaseron ® |
| Coagulation factor IX | Treating hemophilia B as indicated by BeneFix ™ |
| Coagulation factor IX-VL-CL | Treating hemophilia B as indicated by BeneFix ™ |
| Coagulation factor-IX-CH2-CH3 | Treating hemophilia B as indicated by BeneFix ™ |
| GM-CSF | Treating diseases as indicated by Leukine ® |
| GM-CSF-VL-CL | Treating diseases as indicated by Leukine ® |
| GM-CSF-CH2-CH3 | Treating diseases as indicated by Leukine ® |
| PlGF antagonist peptides | Neutralizing PlGF or Flt-1, also treating cancers |
| VEGF antagonist peptides | Neutralizing VEGF, also treating cancers |
| Tyrosine kinase inhibitors | Treating cancers |
| Aβ12-28P fused to CH2-CH3 | Treating Alzheimer's disease |

TABLE 5

Selected Examples of Type 5 products for which the subunits of $a_2a'_2$ are based on binding domains of two different immunoglobulins

| Target 1 | Target 2 | Application |
| --- | --- | --- |
| CD20 | CD22 | Treating lymphomas or autoimmune diseases |
| CD19 | CD20 | Treating lymphomas or autoimmune diseases |
| EGFR | IGFR1 | Treating solid tumors |
| VEGFR1/Flt-1 | VEGFR2/KDR | Blocking VEGF binding |
| VEGFR3/Flt-4 | VEGFR2/KDR | Blocking VEGF binding |
| CD19 | CD3/TCR | Treating cancers |
| CD19 | CD16/FcγRIIIa | Treating cancers |
| CD19 | CD64/FcγRI | Treating cancers |

TABLE 5-continued

Selected Examples of Type 5 products for which the subunits of $a_2a'_2$ are based on binding domains of two different immunoglobulins

| Target 1 | Target 2 | Application |
|---|---|---|
| HER2/neu | CD89/FcαRI | Treating cancers |
| HER2/neu | CD16 | Treating cancers |
| HER2/neu | CD64 | Treating cancers |
| HER2/neu | CD3 | Treating cancers |
| HER2 (Herceptin) | HER2 (Omnitarg) | Treating cancers |
| HER2 | HER3 | Treating cancers |
| CD30 | CD64 | Treating cancers |
| CD33 | CD64 | Treating cancers |
| EGFR | CD2 | Treating cancers |
| EGFR | CD64 | Treating cancers |
| EGFR | CD16 | Treating cancers |
| EGFR | CD89 | Treating cancers |
| PfMSP-1 | CD3 | Treating malaria |
| EpCAM/17-1A | CD3 | Treating cancers |
| hTR | CD3 | Treating cancers |
| IL-2R/Tac | CD3 | Treating cancers |
| CA19-9 | CD16 | Treating cancers |
| MUC1 | CD64 | Treating cancers |
| HLA class II | CD64 | Treating cancers |
| $G_{D2}$ | CD64 | Treating neuroblastoma |
| Carbonic anhydrase IX | CD89 | Treating renal cell carcinoma |
| TAG-72 | CD89 | Treating cancers |
| EpCAM | Adenovirus fiber knob | Retargeting viral vector to EpCAM + cancers |
| PSMA | Adenovirus fiber knob | Retargeting viral vector to prostate cancers |
| CEA | Adenovirus fiber knob | Retargeting viral vector to CEA-positive cancer |
| HMWMAA | Adenovirus fiber knob | Retargeting viral vector to melanoma |
| Carbonic anhydrase IX | Adenovirus fiber knob | Retargeting viral vector to renal cell carcinoma |
| CD40 | Adenovirus fiber knob | Retargeting viral vector to dendritic cells |
| M13 coat protein | Alkaline phosphatase | Detecting virus |
| GpIIb/IIIa | tPA | Enhancing thrombolysis |
| A1B1 of CEA | N of CEA | Inhibiting cancer invasion/metastasis |
| CD20 | CD55 | Treating B-cell lymphoma |
| CD20 | CD59 | Treating B-cell lymphoma |
| CD20 | CD46 | Treating B-cell lymphoma |
| Carbonic anhydrase IX | CD55 | Treating renal cell carcinoma |
| EpCAM | CD55 | Treating cancers |
| Migration inhibitory factor (MIF) | Lipopolysaccharide (LPS) | Treating sepsis and septic shock |
| MIF | C5a receptor (C5aR) | Treating sepsis and septic shock |
| MIF | IL-6 | Treating sepsis and septic shock |
| Toll-like receptor-2 (TLR2) | LPS | Treating sepsis and septic shock |
| High mobility group box protein 1 (HMGB-1) | TNF-α | Treating sepsis and septic shock |
| MIF | NCA-90/CEACAM6 | Treating cancer, sepsis and septic shock |
| MIF | HLA-DR | Treating sepsis and septic shock |
| MIF | Low-density lipoprotein (LDL) | Treating atherosclerosis |
| NCA90 | LDL | Treating atherosclerosis |
| CD83 | LDL | Treating atherosclerosis |
| CD74 | LDL | Treating atherosclerosis |
| TNF | CD20 | Lymphoma therapy |
| TNF | CD22 | Lymphoma therapy |
| TNF | CD74 | Treating cancers |
| TNF | MIF | Treating autoimmune diseases |
| TNF | CD83 | Treating autoimmune diseases |
| Tumor antigens | Histamine-succinly-glycine (HSG) | Pre-targeting applications for cancer diagnosis and therapy |
| Blys/CD257 | April/CD256 | Treating lupus and arthritis |

TABLE 6

Selected Examples of Type 6 products for which the subunits of $a_2a'_2$ are based on immunoglobulins and non-immunoglobulins

| Target for mAb | Precursor for nonimmunoglobulin | Application |
|---|---|---|
| CD74 | Rap-VL-CL | Treating cancers |
| CD22 | Rap-VL-CL | Treating cancers |
| MUC1 | Rap-VL-CL | Treating cancers |
| EGP-1 | Rap-VL-CL | Treating cancers |
| IGF1R | Rap-VL-CL | Treating cancers |
| Pgp/p-170 | Rap-VL-CL | Treating cancers |
| CD22 | Pseudomonas exotoxin (PE)38 | Treating cancers |
| CD30 | PE38 | Treating cancers |
| CD25/Tac | PE38 | Treating cancers |
| Le$^Y$ | PE38 | Treating cancers |
| Mesothelin | PE38 | Treating cancers |
| HER2 | PE38 | Treating cancers |
| EpCAM | PE38 | Treating cancers |
| Pgp/p-170 | PE38 | Treating cancers |
| CD25 | dgA | Treating cancers |
| CD30 | dgA | Treating cancers |
| CD19 | dgA | Treating cancers |
| CD22 | dgA | Treating cancers |
| CD25 | PLC | Treating cancers |
| Gp240 | Gelonin | Treating melanoma |
| Pgp/p-170 | IL-2 | Treating cancers |
| CD3 | DT390 | Treating graft versus host disease (GVHD) |
| GpIIb/IIIa | tPA | Enhancing thrombolysis |
| GpIIb/IIIa | urokinase | Enhancing thrombolysis |
| GpIIb/IIIa | hirudin | Enhancing thrombolysis |
| X | Carboxypeptidase G2 (CPG2) | Prodrug therapy |
| X | penicillinamidase | Prodrug therapy |
| X | β-lactamase | Prodrug therapy |
| X | Cytosine deaminase | Prodrug therapy |
| X | Nitroreductase | Prodrug therapy |
| Aβ | Tf | Treating Alzheimer's disease |

TABLE 7

Selected Examples of Type 7 products for which the subunits of $a_2a'_2$ are based on two different non-immunoglobulins

| Precursor 1 | Precursor 2 | Application |
|---|---|---|
| IL-4 | PE38 | Treating pancreatic cancer |
| IL-4 | Rap-VL-CL | Treating pancreatic cancer |
| sIL-4R | sIL-13R | Treating asthma, allergy |
| Aβ12-28P fused to CH2-CH3 | Tf | Treating Alzheimer's disease |
| Aβ12-28P | Tf | Treating Alzheimer's disease |

What is claimed is:

1. A method of delivering a diagnostic or therapeutic agent comprising: a) obtaining a homodimer, each monomer of the homodimer comprising a dimerization and docking domain (DDD) of human protein kinase A regulatory subunit wherein the DDD consists the sequence of SEQ ID NO: 1 (DDD1) or SEQ ID NO: 2 (DDD2) and, wherein the DDD peptide sequences bind together to form a homodimer and the homodimer comprises at least one diagnostic or therapeutic agent; and b) administering the homodimer to a subject.

2. The method of claim 1, wherein the two DDD peptide sequences of the homodimer are covalently attached to each other by disulfide bonds.

3. The method of claim 1, wherein each monomer further comprises an antigen-binding antibody fragment that binds to a tumor-associated antigen (TAA).

4. The method of claim 3, wherein each monomer is a fusion protein comprising said DDD peptide sequence of SEQ ID NO: 2 and an antigen-binding antibody fragment.

5. The method of claim 4, wherein the monomer further comprises a linker peptide between the antigen-binding antibody fragment and the DDD.

6. The method of claim 3, wherein the antigen-binding antibody fragment is chemically linked to the DDD peptide sequence.

7. The method of claim 3, wherein the antigen-binding antibody fragment is selected from the group consisting of a Fab fragment, a Fab' fragment, a single domain antibody (DAB) and a single chain Fv (scFv).

8. The method of claim 3, wherein the antigen-binding antibody fragment binds to a tumor-associated antigen (TAA) and the therapeutic agent is an anti-cancer therapeutic agent.

9. The method of claim 8, wherein the tumor-associated antigen is selected from the group consisting of carbonic anhydrase IX, alpha-fetoprotein, antigen specific for A33 antibody, BrE3-antigen, CA125, CD1, CD1a, CD3, CD5, CD15, CD16, CD19, CD20, CD21, CD22, CD23, CD25, CD30, CD33, CD38, CD45, CD74, CD79a, CD80, CD138, colon-specific antigen-p (CSAp), CEA (CEACAM5), CEACAM6, EGFR, EGP-1, EGP-2, Ep-CAM, Flt-1, Flt-3, folate receptor, G250 antigen, HLA-DR, human chorionic Gonadotropin (HCG) and its subunits, HER2/neu, hypoxia inducible factor (HIF-1), Ia, IL-2, IL-6, IL-8, insulin growth factor-1 (IGF-1), KC4-antigen, KS-1-antigen, KS1-4, Le-Y, macrophage migration inhibitory factor (MIF), MAGE, MUC1, MUC2, MUC3, MUC4, NCA66, NCA95, NCA90, antigen specific for PAM-4 antibody, placental growth factor, p53, prostatic acid phosphatase, PSA, PSMA, RS5, S100, TAC, TAG-72, tenascin, TRAIL receptors, Tn antigen, Thomson-Friedenreich antigens, tumor necrosis antigens, VEGF, ED-B fibronectin, and 17-1A-antigen.

10. The method of claim 8, wherein the antigen-binding antibody fragment is a fragment of an antibody selected from the group consisting of anti-CEA (hMN-14), anti-CD20 (hA20), anti-CD22 (hLL2), anti-CD74 (hLL1), anti-MUC-1 (hPAM4), anti-CD14, anti-CD111, omalizumab, muromonab, abciximab, infliximab and palivizumab.

11. The method of claim 3, wherein the antigen-binding antibody fragment comprises an immunoglobulin light chain (VL-CL) or an immunoglobulin Fc domain (CH2-CH3).

12. The method of claim 11, wherein the cysteine at the carboxyl-terminus of the CL that connects the CL to CH1 is deleted or mutated to a non-cysteine.

13. The method of claim 3, wherein the antigen-binding antibody fragment is a fragment of a human, humanized or chimeric antibody.

14. The method of claim 1, wherein the therapeutic agent is selected from the goup consisting of a chemotherapeutic agent, a cytokine, a chemokine, an anti-angiogenic agent, an apoptotic agent, a drug, a prodrug, a toxin, an enzyme, a radioisotope, an immunomodulator, an antibiotic and a hormone.

15. The method of claim 14, wherein the drug is selected from the group consisting of abrin, amantadine, amoxicillin, amphotericin B, ampicillin, aplidin, azaribine, anastrozole, azacytidine, aztreonam, azithromycin, bacitracin, trimethoprim/sulfamethoxazole, Batrafen, bifonazole, bleomycin, bortezomib, bryostatin-1, busulfan, calicheamicin, camptothecin, 10-hydroxycamptothecin, carbenicillin, caspofungin, carmustine, cefaclor, cefazolin, cephalosporins, cefepime, ceftriaxone, cefotaxime, celecoxib, chlorambucil, chloramphenicol, ciprofloxacin, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, diphtheria toxin, DNase I, doxorubicin, 2-pyrrolino-doxorubicine (2P-DOX), doxycycline, cyano-morpholino doxorubicin, doxorubicin glucuronide, epirubicin glucuronide, ethinyl estradiol, estramustine, estrogen receptor binding agents, etoposide, etoposide glucuronide, etoposide phosphate, erythrocycline, erythromycin, flagyl, farnesyl-protein transferase inhibitors, floxuridine (FUdR), 3',5'—O-dioleoyl-FudR (FUdR-dO), fludarabine, flutamide, fluorouracil, fluoxymesterone, ganciclovir, gentamycin, gelonin, gemcitabine, hydroxyprogesterone caproate, hydroxyurea, idarubicin, ifosfamide, isoniazid, itraconazole, kanamycin, ketoconazole, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, minocycline, naftifine, nalidixic acid, neomycin, navelbine, nitrosurea, nystatin, ranpirnase, oxacillin, paromomycin, penicillin, pentamidine, piperacillin-tazobactam, phenyl butyrate, prednisone, procarbazine, paclitaxel, pentostatin, pokeweed antiviral protein, PSI-341, semustine, rifabutin, rifampin, rimantadine, streptomycin, sulfamethoxazole, sulfasalazine, streptozocin, tamoxifen, taxanes, taxol, testosterone propionate, tetracycline, thalidomide, thioguanine, thiotepa, teniposide, topotecan, transplatinum, trimethoprim sulfamethoxazole, uracil mustard, valacyclovir, vancomycin, vinblastine, vinorelbine, vincristine, zanamir and zithromycin.

16. The method of claim 15, wherein the toxin is selected from the group consisting of a bacterial toxin, a plant toxin, ricin, abrin, a ribonuclease (RNase), DNase I, Staphylococcal enterotoxin-A, pokeweed antiviral protein, gelonin, diphtherin toxin, *Pseudomonas* exotoxin, *Pseudomonas* endotoxin, Ranpirnase (Rap) and Rap (N69Q).

17. The method of claim 14, wherein the immunomodulator is selected from the group consisting of a cytokine, a stem cell growth factor, a lymphotoxin an interleukin, a colony-stimulating factor, interferon-α, interferon-β, interferon-γ, and the stem cell growth factor designated "S1 factor."

18. The method of claim 14, wherein the cytokine is selected from the group consisting of human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, tumor necrosis factor-α, tumor necrosis factor-β, mullerian-inhibiting substance, mouse gonadotropin-associated peptide, inhibin, activin, vascular endothelial growth factor, integrin, thrombopoietin (TPO), NGF-β, platelet-growth factor, TGF-α, TGF-β, insulin-like growth factor-I, insulin-like growth factor-II, erythropoietin (EPO), osteoinductive factor, interferon-α, interferon-β, interferon-γ, macrophage-CSF (M-CSF), granulocyte-macrophage-CSF (GM-CSF), granulocyte-CSF (G-CSF), IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, LIF, kit-ligand, FLT-3, angiostatin, thrombospondin, endostatin and LT.

19. The method of claim 1, wherein the diagnostic or therapeutic agent is selected from the group consisting of $^{225}$Ac, $^{211}$At, $^{212}$Bi, $^{213}$Bi, $^{14}$C, $^{51}$Cr, $^{36}$Cl, $^{45}$Ti, $^{57}$Co, $^{58}$Co, $^{62}$Cu, $^{64}$Cu, $^{67}$Cu, $^{166}$Dy, $^{152}$Eu, $^{18}$F, $^{67}$Ga, $^{68}$Ga, $^{195m}$Hg, $^{166}$Ho, $^{3}$H, $^{111}$In, $^{123}$I, $^{124}$I, $^{125}$I, $^{131}$I, $^{52}$Fe, $^{59}$Fe, $^{177}$Lu, $^{191}$Os, $^{212}$Pb, $^{32}$P, $^{33}$P, $^{142}$Pr, $^{195m}$Pt, $^{223}$Ra, $^{186}$Re, $^{188}$Re, $^{189}$Re, $^{47}$Sc, $^{75}$Se, $^{111}$Ag, $^{153}$Sm, $^{89}$Sr, $^{35}$S, $^{161}$Tb, $^{94m}$Tc, $^{99m}$Tc, $^{86}$Y, $^{90}$Y, and $^{89}$Zr.

20. The method of claim 1, wherein the diagnostic agent is selected from the group consisting of a radioisotope, an imaging agent, a dye, an enzyme, a fluorescent agent, a chemiluminescent agent, a bioluminescent agent, a paramagnetic ion and an ultrasound label.

21. The method of claim 20, wherein the imaging agent is selected from the group consisting of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) erbium (III), lanthanum (III), gold (III), lead (II) and bismuth (III).

22. The method of claim 20, wherein the fluorescent agent is selected from the group consisting of Alexa 350, Alexa 430, AMCA, aminoacridine, BODIPY 630/650, BODIPY 650/665, BODIPY-FL, BODIPY-R6G, BODIPY-TMR, BODIPY-TRX, 5-carboxy-4',5'-dichloro-2',7'-dimethoxy fluorescein, 5-carboxy-2',4',5',7'-tetrachlorofluorescein, 5-carboxyfluorescein, 5-carboxyrhodamine, 6-carboxyrhodamine, 6- carboxytetramethyl amino, Cascade Blue, Cy2, Cy3, Cy5,6-FAM, dansyl chloride, Fluorescein, HEX, 6-JOE, NBD (7-nitrobenz-2-oxa-1,3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, La Jolla blue dye, allopycocyanin, allococcyanin B, phycocyanin C, phycocyanin R, thiamine, phycoerythrocyanin, phycoerythrin R, REG, Rhodamine Green, rhodamine isothiocyanate, Rhodamine Red, ROX, TAMRA, TET, TRIT (tetramethyl rhodamine isothiol), Tetramethylrhodamine, and Texas Red.

23. The method of claim 1, wherein the homodimer further comprises one or more effectors or carriers conjugated to the homodimer by either covalent or non-covalent linkage.

24. The method of claim 23, wherein the effector is selected from the group consisting of a diagnostic agent, a therapeutic agent, a chemotherapeutic agent, a radioisotope, an imaging agent, an anti-angiogenic agent, a cytokine, a chemokine, a growth factor, a drug, a prodrug, an enzyme, a ligand for a cell surface receptor, a chelator, an immunomodulator, a hormone, a photodetectable label, a dye, a toxin, a contrast agent, a paramagnetic label, an ultrasound label, a pro-apoptotic agent, a liposome and a nanoparticle.

25. The method of claim 23, wherein the effectors or carriers are chemically cross-linked to the homodimer.

26. The method of claim 23, wherein the homodimer is attached to two or more effectors or two or more carriers.

27. The method of claim 26, wherein the two or more carriers or two or more effectors are either identical or different.

28. The method of claim 23, wherein the one or more carriers comprise at least one diagnostic or therapeutic agent.

* * * * *